United States Patent [19]
Belshe et al.

[11] Patent Number: 6,110,457
[45] Date of Patent: *Aug. 29, 2000

[54] LIVE ATTENUATED VACCINES BASED ON CP45 HPIV-3 STRAIN AND METHOD TO ENSURE ATTENUATION IN SUCH VACCINES

[75] Inventors: Robert B. Belshe; Ranjit Ray, both of St. Louis, Mo.

[73] Assignee: St. Louis University, St. Louis, Mo.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/987,439

[22] Filed: Dec. 9, 1997

Related U.S. Application Data

[63] Continuation-in-part of application No. 08/569,853, Dec. 8, 1995, Pat. No. 5,869,036.
[60] Provisional application No. 60/032,943, Dec. 9, 1996.

[51] Int. Cl.[7] .............................. A01N 63/00; C12N 7/00; C12N 15/09; C12N 5/00
[52] U.S. Cl. .................. 424/93.2; 435/235.1; 435/320.1; 435/325; 435/455; 514/44
[58] Field of Search .............................. 435/235.1, 320.1, 435/4, 5, 6, 325, 455, 440; 424/93.1, 93.2; 514/44

[56] References Cited

U.S. PATENT DOCUMENTS 5,869,036  2/1999  Belshe et al. .......................... 424/93.2

OTHER PUBLICATIONS

Strayer, D. S. The Viruses Don't Always Read the Books: Engineered Vaccines and Gene Therapy using Viral Vectors. Laboratory Investigation, vol. 71, No. 3, pp. 319–323, 1994.
Cohen, J. Bumps on the Vaccine Road. Science, vol. 265, pp. 1371–1373, Sep. 2, 1994.

*Primary Examiner*—Deborah J. Clark
*Attorney, Agent, or Firm*—Senniger, Powers, Leavitt & Roedel

[57] ABSTRACT

The present invention is based upon correlation of two attenuating lesions of the cp45 strain to specific genetic defects in the viral genome of cp45. Specifically, it is now understood that a significant level of attenuation of cp45 giving rise to its temperature-sensitive and cold-adapted phenotypes is directly associated with mutation of the large, or L, gene of cp45 relative to the corresponding gene in the wild-type JS strain. Moreover, it is further understood that a second attenuating lesion exits independent of the temperature-sensitive lesion, and is directly associated with mutation of the hemagglutinin-neuraminidase gene, or HN gene, of cp45 relative to the corresponding gene in the wild-type HPIV-3 (JS) strain. The correlation of these two attenuating lesions of cp45 to specific genes enables several practical applications. It is now possible to create vaccines directed at other wild-type HPIV-3 viruses and, additionally, vaccines directed at target viruses other than HPIV-3 using genetic engineering techniques. For example, the mutated L and/or HN genes of cp45 can be incorporated into the viral genome of a target virus. Alternatively, the genes of the target virus which encode its surface antigens can be incorporated into the viral genome of cp45. Moreover, it is possible to determine whether an HPIV-3 strain or a hybrid virus strain made by the methods disclosed herein is attenuated by confirming the presence or absence of mutations in its L and/or HN genes.

66 Claims, 16 Drawing Sheets

FIG. 1 cp45

| Nucleotide | | | Amino Acid | |
|---|---|---|---|---|
| Location | Change | | Location | Change (wt -» cp45) |
| 23 | T » C | | | |
| 24 | C » T | | | |
| 28 | G » T | | | |
| 334 | TCC » TCT | | 85 | |
| 376 | AAT » AAC | | 99 | |
| 627 | CCC » ACC | | 199 | Pro -» Thr |
| 658 | AAC » AAT | | 155 | Ile -» Val |
| 1451 | ATA » GTA | | 420 | Ala -» Thr |
| 1541 | GCA » ACA | | 450 | |
| 115 | GGT » GGC | | 14 | |
| 1224 | GTT » GCT | | 384 | Val -» Ala |
| 700 | TAT » TAC | | 226 | |
| 1348 | GAA » GAG | | 442 | |
| 2698 | TCA » TCG | | 892 | |
| 2846 | TAC » CAC | | 942 | Tyr -» His |
| 2998 | TTG » TTT | | 992 | Leu -» Phe |
| 3958 | TTC » TTT | | 1312 | |
| 4695 | ACT » ATT | | 1558 | Thr -» Ile |

LEADER — NP | P | M | F | HN | L

LIVE ATTENUATED VACCINES BASED ON CP45 HPIV-3 STRAIN AND METHOD TO ENSURE ATTENUATION IN SUCH VACCINES

The present application is a continuation-in-part application of U.S. patent application Ser. No. 08/569,853 filed Dec. 8, 1995, U.S. Pat. No. 5,869,036, Feb. 9, 1999. The present application also claims priority to U.S. provisional application Ser. No. 60/032,943 filed Dec. 9, 1996.

Funding for research supporting this invention was provided, in part, by the U.S. Department of Health and Human Services. The U.S. Government may have certain rights in this invention.

BACKGROUND OF THE INVENTION

The present invention relates to enveloped, negative-sense, single-stranded RNA viruses and to the use of such viruses as live attenuated vaccines. Specifically, the invention relates to new human vaccines for enveloped viruses such as parainfluenza, respiratory syncytial virus, measles and influenza viruses, among others. The invention also relates to a method for screening such vaccines to ensure attenuation prior to their administration and to check the stability of the attenuated strain after administration.

A number of viruses may cause severe infections in humans and animals. For example, respiratory syncytial virus (RSV) and parainfluenza virus are two of the leading causes of severe upper and/or lower respiratory tract disease in neonates and young infants. Other viruses, such as influenza virus, measles virus and human immunodeficiency virus, are also of significant concern.

A variety of vaccines have been developed over the years to prevent viral infections in animals and humans. Two principle types of vaccines have been used: killed viruses and attenuated live virus. A killed virus is typically inactivated by chemical or physical treatment, but is generally less effective in stimulating a lasting immune response than an attenuated live virus. Attenuated live viruses are typically more effective, but may revert back to their virulent state while in the body. The time and cost involved in developing either killed or live vaccines is significant.

Live, attenuated vaccines may be obtained directly from progeny viruses isolated from infected animals. For example, U.S. Pat. No. 3,927,209 to Straub discloses a parainfluenza type-3 vaccine isolated as a virus strain from a bovine respiratory tract. Live attenuated vaccines may also be obtained by repeatedly cold passaging a wild-type strain through suitable cultures until the virus has lost its original pathogenic properties. For example, cp45, a cold-adapted, temperature sensitive strain was obtained by passing the wild-type virus (JS strain) of HPIV-3 45 times at reduced temperatures. (Belshe and Hissom, 1982). The temperature sensitive cp45 strain is currently under evaluation for use as a candidate vaccine in humans. (Karron et al. 1995; Hall et al. 1993; Belshe et al. 1992; Clements et al. 1991; Crookshanks-Newman and Belshe 1986). Recent evaluation in children has revealed the cp45 strain to be highly attenuated and effective in stimulating immunogenic response. (Karron et al. 1995; Belshe et al. 1992).

Attenuation in a particular vaccine strain is commonly evaluated with respect to three phenotypes of the strain: cold adaptation, temperature sensitivity and plaque size or yield in tissue culture. Cold adaptation relates to the ability of the virus to grow at 20° C. and the temperature sensitivity relates to whether such growth is inhibited at temperatures of around 40° C. Plaque titers are an assay for quantitatively evaluating the extent of virus growth, and are commonly used to evaluate the extent of cold-adaptive and/or temperature sensitive phenotypes. Other methods for determining whether an vaccine is attenuated involve administering the vaccine to primates. For example, new polio vaccine lots are typically administered to monkeys before being approved for sale by the FDA.

A continuing need exists for developing new vaccines. The prior art methods of developing live attenuated vaccines by cold passaging, while often effective, are not predictable as to their success, and are necessarily limited to application against a single virus. A need also exists for alternative methods to determine whether a virus is sufficiently attenuated. Characterization of cold adaptive and temperature sensitive phenotypes are not definitive. Administration of vaccines to test animals are likewise not definitive, and are inefficient.

SUMMARY OF THE INVENTION

It is therefore an object of the invention to develop vaccines which are suitable for use against a variety of human and animal viruses, and particularly, against viruses such as human parainfluenza viruses types 1, 2 or 3 and RSV. It is likewise an object to provide more efficient and reproducible methods for determining whether a virus strain is attenuated.

Briefly, therefore, the present invention is directed to enveloped, negative-sense, single-stranded RNA hybrid viruses, and further, to live, attenuated human and/or animal vaccines comprising the hybrid viruses in combination with a pharmaceutically acceptable carrier. Vaccines comprising the hybrid virus can be directed against a variety of target viruses, including human parainfluenza type-3 (HPIV-3) viruses and viruses other than HPIV-3.

A hybrid virus suitable for use in a vaccine directed against non-HPIV-3 target virus has a chimeric viral genome comprising the following genes operatively linked for expression in combination with any other genes necessary to form a viable virus: (i) a nucleic acid sequence which encodes one or more surface antigens of a target virus and (ii) a nucleic acid sequence which encodes a variant large protein, L. The target virus is, in this case, not a HPIV-3 virus and the target virus has surface antigens or proteins which are antigenically different from surface antigens of cp45. The variant L protein is a HPIV-3 L protein having an amino acid sequence which has at least about a 90% sequence identity with the amino acid sequence of the wild-type HPIV-3 (JS) L protein. Additionally, the variant L protein has at least one variation in amino acid sequence relative to its wild-type HPIV-3 L protein and has polymerase activity which is less than the polymerase activity normally associated with the target virus at a temperature of about 39° C.

The genome of the immediately aforementioned hybrid virus can comprise, operatively linked for expression: (i) a nucleic acid sequence which is the same as the nucleic acid sequence of the 3' leader region of cp45; (ii) a nucleic acid sequence which encodes the nucleocapsid protein, NP, of cp45; (iii) a nucleic acid sequence which encodes the phosphoprotein, P[+C], of cp45; (iv) a nucleic acid sequence which encodes the matrix protein, M, of cp45; (v) a nucleic acid sequence which encodes at least one surface antigen of a target virus selected from the group consisting of HPIV-1, HPIV-2 and RSV; and (vi) a nucleic acid sequence which encodes a variant large protein, L, having RNA-polymerase activity which is less than the polymerase activity normally associated with the target virus at a temperature of about 39° C. The variant L protein has, in this case, at least about a 99.8% sequence identity with the amino acid sequence of the wild-type HPIV-3 (JS) L protein and has at least two substitutions in amino acid sequence relative to the wild-type HPIV-3 (JS) L protein, the substitutions being His for Tyr at residue 942 SEQ ID NO.1 and Phe for Leu at residue 992 SEQ ID NO. 1.

Another hybrid virus suitable for use in a vaccine directed against non-HPIV-3 target virus has a chimeric viral genome comprising genes operatively linked for expression. These genes include, in combination with other genes necessary to form a viable virus, a nucleic acid sequence which encodes (i) at least one surface antigen of a non-HPIV-3 target virus which is antigenically different from surface antigens of cp45 and (ii) a portion of the cp45 HN protein. The encoded portion has a neuraminidase activity and includes an amino acid sequence which is the same as the amino acid sequence from residue 160 to residue 385 of the HN protein of cp45. The invention is further directed to live, attenuated vaccines suitable for use against the target virus. The vaccine comprises the immediately aforementioned hybrid virus and a pharmaceutically acceptable carrier. The invention is directed, moreover, to a plasmid vector having a genome which includes the genome of the hybrid virus and to methods for producing the hybrid virus.

The invention is further directed to an enveloped, negative-sense, single-stranded RNA hybrid virus suitable for use in a vaccine directed against HPIV-3 viruses. One such hybrid virus has a genome which comprises the following genes operatively linked for expression in combination with any other genes necessary to form a viable virus: (i) a nucleic acid sequence which is the same as the nucleic acid sequence of the 3' leader region of a wild-type HPIV-3 target virus or which encodes at least one protein selected from the group consisting of the matrix protein, M, of the target virus, the fusion protein, F, of the target virus and the hemagglutinin-neuraminidase protein, HN, of the target virus, and (ii) a nucleic acid sequence which encodes a variant HPIV-3 large protein, L. The variant L protein has an amino acid sequence which has at least one variation in amino acid sequence relative to the L protein of the target virus, and has RNA-polymerase activity which is less than the RNA-polymerase activity normally associated with the L protein of the target virus at a temperature of about 39° C.

Another hybrid virus suitable in the same regard is an enveloped, negative-sense, single-stranded RNA hybrid virus having a genome comprising the following genes operatively linked for expression in combination with any other genes necessary to form a viable virus: (i) a nucleic acid sequence which is the same as the nucleic acid sequence of the 3' leader region of a wild-type HPIV-3 target virus or which encodes at least one protein selected from the group consisting of the matrix protein, M, of the target virus, the fusion protein, F, of the target virus and the large protein, L, of the target virus, and (ii) a nucleic acid sequence which encodes a variant hemagglutinin-neuraminidase protein, HN. The variant HN protein has an amino acid sequence which has at least about a 90% sequence identity with the amino acid sequence of the HN protein described in SEQ ID NO. 2 of wild-type HPIV-3 (JS) virus and which has at least one variation in amino acid sequence relative to the HN protein of the target virus. The variant HN protein also has at least one variation in amino acid sequence relative to the HN protein of the HPIV-3 (JS) virus. The variation relative to the HN protein of HPIV-3 (JS) is at or within about five amino acid residues of residue 384 of the JS HN protein described in SEQ ID NO. 1. The variant HN protein has neuraminidase activity which is less than the neuraminidase activity normally associated with the HN protein of the target virus.

The invention is also directed to a plasmid vector comprising a positive or negative sense genome having the genes for any of the aforementioned hybrid viruses operatively linked for expression in combination with other genes necessary to form a viable plasmid. For example, the plasmid genome of one plasmid vector of the invention includes: (i) a nucleic acid sequence which encodes the surface antigens of a target virus and (ii) a nucleic acid sequence which encodes a variant large protein, L. The target virus surface antigens are antigenically different from surface antigens of cp45. The variant L protein has an amino acid sequence which has at least about a 90% sequence identity with the amino acid sequence of the wild-type HPIV-3 (JS) L protein and which has at least one variation in amino acid sequence relative to the L protein of its wild-type L protein and relative to wild-type HPIV-3 (JS). The variant L protein has an RNA-polymerase activity which is less than the polymerase activity normally associated with the target virus at a temperature of about 39° C.

The invention is, moreover, directed to a host cell transfected with a plasmid vector of the invention.

The invention is also directed to methods for producing enveloped, negative-sense, single-stranded RNA viruses. A host cell is transfected with a plasmid vector of the invention which includes the genome of one of the aforementioned hybrid viruses (e.g. such as the plasmid vector described in detail above). The host cell is then cotransfecting with plasmid vectors that express wild-type HPIV-3 NP, P and L proteins. The transfected host cell is incubated to produce a hybrid virus. The hybrid virus is then isolated in a pharmaceutically acceptable carrier or medium.

The invention is furthermore directed to a method for determining whether a HPIV-3 or a cp45-hybrid virus is attenuated. The method comprises confirming the presence of at least one variation in the genome of the virus relative to the genome of wild-type HPIV-3. The variation is in the region of the genome which encodes the L protein or the HN protein.

The present invention is also directed to a method for determining whether a virus has a temperature sensitive phenotype. A sample of HPIV-3 or a cp45-hybrid virus is obtained and a first plaque assay is performed. A host cell is transfected with a plasmid vector that expresses wild-type HPIV-3 L protein and infected with the virus. After incubating, a second plaque assay is performed and compared to the first plaque assay.

The invention offers new opportunities for producing live vaccines which can be used in conjunction with a variety of viruses. Because vaccines of the present invention incorporate, in a preferred embodiment, the cp45 genes which give rise to the attenuating lesions exhibited by cp45, the vaccines disclosed and claimed herein are expected to be attenuated during use in humans or animals. Furthermore, the invention provides a direct and efficient method for determining temperature sensitive phenotype and attenuation in HPIV-3 viruses and in cp45 hybrid viruses.

Other features and objects of the present invention will be in part apparent to those skilled in the art and in part pointed out hereinafter.

BRIEF DESCRIPTION OF THE DRAWINGS

FIG. 1 is a schematic representation of the HPIV-3 viral genome, shown vertically 5' (top) to 3'(bottom) in its cDNA sense. The geneomic regions are labeled to correspond to the leader region and the regions of the genome which encode the nucleocapsid protein, NP, the phosphoprotein, P(+C), the matrix protein, M, the fusion protein, F, the hemagglutinin-neuraminidase protein, HN and the large protein, L. The position number for nucleotide changes in the leader region correspond to their position in relation to the genome, whereas all other position numbers refer to the position of nucleotide changes within the individual gene.

FIG. 2A shows CDNA after 15 cycles of PCR amplification from wild-type HPIV-3 (lane 1), cp45 (lane 2) and plasmid DNA containing the P gene (lane 3). The size of the amplified DNA, shown by an arrow on the right, was calculated on the basis of migration of φX174/HaeIII-digested DNA marker (data not shown). FIG. 2B depicts the results of a slot blot hybridization analysis using phosphorimaging analysis using the Molecular Dynamics PhosphorImager. As indicated thereon, the left lane is for cp45 and the right lane for the wild-type HPIV-3 (JS) strain.

FIGS. 3A and 3B are photos depicting the results of a pulse-chase experiment, demonstrating the kinetics of viral protein synthesis. Cells infected with the wild-type HPIV-3 (JS) or cp45 were grown at 39.5° C. for 24 hours and pulsed with $^{35}$S-protein label for 1 hour. FIG. 3A shows cell lysates immunoprecipitated with Rabbit anti-HPIV-3 at the time points indicated under each lane (0, 1, 2, 3 and 4 hours) for both wild-type JS strain (left-most five lanes) and cp45 (right-most five lanes). FIG. 3B shows cell lysates immunoprecipitated with pooled monoclonal antibodies to HN and NP of wild-type HPIV-3 at the time points indicated under each lane (0, 1, 2 and 3 hours) for both wild-type JS strain (left-most four lanes) and cp45 (right-most four lanes).

FIGS. 4A and 4B are bar graphs showing the reactivities of cp45 and wild-type HPIV-3 with monoclonal antibodies to HN protein (FIG. 4A) and to F protein (FIG. 4B, as determined by ELISA. Results are presented as the mean optical densities (O.D.) from three different experiments at a particular dilution of the antibodies (1:1800). The monoclonal antibodies 7.12.3, 9.1.6.2, 7,14.2, 5.4.8 and 9.4.3.6 define antigenic sites of HPIV-3 (strain 47885). Monoclonal antibodies 170/7, 77/5, c/267, c/215, b/108, a/640 and a/591 were provided by Judy Beeler (World Health Organization Reagent Bank).

FIGS. 5A and 5B are photos of gels depicting the immunoprecipitation of HPIV-3 proteins expressed by the vaccinia virus T7 system with rabbit antiserum and with monoclonal antibodies. HeLa-T4 cells were transfected with plasmids containing the HPIV-3 L, P or NP gene. About 20 hours posttransfection, the cells were radiolabelled with [$^{35}$S]-methionine-[$^{35}$S]-cysteine at 37° C. for 1 hour. The HPIV-3 proteins from cell lysates were immunoprecipitated with a rabbit antiserum to HPIV-3 or a monoclonal antibody to NP and analyzed by SDS-PAGE. The labeled proteins were electrophoresed on SDS-7.5% (FIG. 5A) and SDS-10% (FIG. 5B) in the presence of the reducing agent 2-mercaptoethanol. The lanes in FIG. 5A correspond to: vector DNA-transfected cell lysates immunoprecipitated with rabbit antiserum to HPIV-3 (lane 1); P-gene-transfected cell lysates immunoprecipitated with rabbit antiserum to HPIV-3 (lane 2); and L-gene-transfected cell lysates immunoprecipitated with rabbit antiserum to HPIV-3 (lane 3). The lanes in FIG. 5B correspond to: vector DNA-transfected cell lysates immunoprecipitated with rabbit antiserum to HPIV-3 (lane 1); L-gene-transfected cell lysates immunoprecipitated with rabbit antiserum to HPIV-3 (lane 2); NP-gene-transfected cell lysates immunoprecipitated with a specific monoclonal antibody (lane 3). Positions of molecular weight markers are shown on the left in kilodaltons.

FIGS. 6A through 6D are photos depicting the indirect immunofluorescence staining of cells transiently expressing HPIV-3 NP protein (FIG. 6A), P protein (FIG. 6B) or L protein (FIG. 6C), and shows their growth relative to a negative control (FIG. 6D). Cells expressing HPIV-3 NP, P and L proteins and control cells transfected with vector DNA's were fixed and reacted with a primary anti-HPIV-3 antibody and a secondary mouse anti-rabbit immunoglobulin G-fluorescein isothiocyanate conjugate for immunofluorescence.

FIGS. 7A and 7B are graphs showing the growth characteristics of cp45 (FIG. 7A) and HPIV-3 (JS) (FIG. 7B) in a L-132 cell culture at 32° C. with or without the addition of exogenous bacterial neuraminidase to the culture medium. The bars indicate the standard errors of three independent experiments.

FIGS. 8A through 8D are photos showing the cytopathic effect developed by cells infected with cp45 (FIG. 8A) and HPIV-3 (JS) (FIG. 8B) after growth in culture without exogenous neuraminidase and of cells infected with cp45 (FIG. 8C) and HPIV-3 (JS) (FIG. 8D) after growth in the presence of exogenous neuraminidase. Cells were infected at a multiplicity of infection of 0.01 and incubated at 32° C. for 36 hours either with or without exogenous neuraminidase.

FIGS. 9A through 9D are photos based on immunofluorescent methods which show the distribution of HN glycoprotein of cp45 (FIG. 9A) and HPIV-3 (JS) (FIG. 9B) in tissue culture cells after growth without exogenous neuraminidase, and of cp45 (FIG. 9C) and HPIV-3 (JS) (FIG. 9D) in tissue culture cells after growth in the presence of exogenous neuraminidase.

FIGS. 10A and 10B are graphs showing the variation in neuraminidase activity of cp45 (FIG. 10A) and HPIV-3 (JS) (FIG. 10B) for infected cell cultures incubated at various Ph. The neuraminidase activity assays were performed using fetuin (open circle) or neuraminlactose (closed circle) as substrates.

FIGS. 11A and 11B are graphs showing the variation in neuraminidase activity with time in kinetic studies in which cp45 (open circles) and wild-type JS strains (closed circles) were assayed using a neuraminlactose substrate having either a 2→3 linkage (FIG. 11A) or a 2→6 linkage (FIG. 11B).

FIGS. 12A and 12B are bar graphs showing the results of neuraminidase activity inhibition studies in which cp45 (shaded areas) and HPIV-3 (JS) (unshaded areas) were assayed with a monospecific rabbit antiserum to affinity purified HPIV-3 HN glycoprotein and three monoclonal antibodies to the HN glycoprotein, 2-14-1, 13-9-6-2 and 170/8 using either fetuin (FIG. 12A) or neuraminlactose (FIG. 12B) as substrates.

SEQ ID NO. 1 lists the amino acid sequence of the L protein of HPIV-3 strain (JS). The cp45 strain differs from this sequence by the substitution of His for Tyr at position 942, the substitution of Phe for Leu at position 992, and the substitution of Ile for Thr at position 1558.

SEQ ID NO. 2 lists the coding strand nucleic acid sequence for the L protein of HPIV-3 strain (JS). The cp45 strain differs from this sequence by the substitution of C for T at position 9323, the substitution of G for A at position 9971, the substitution of G for A at position 11,321, the substitution of C for T at position 11,469, the substitution of T for G at position 11,621, the substitution of T for C at position 12,581, and the substitution of T for C at position 13,318.

Figure 2A:
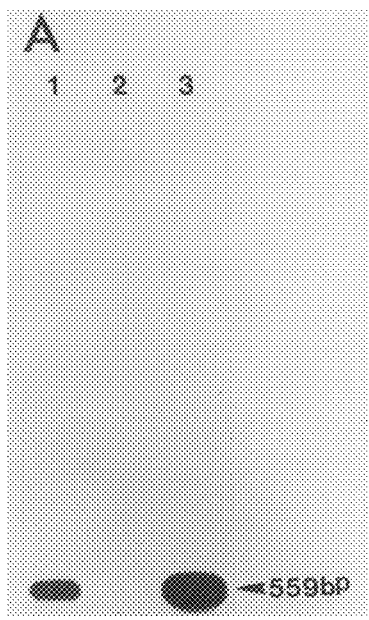
FIGS. 2A and 2B are photos depicting the results of Southern hybridization or southern blot analysis, comparing mRNA levels of P protein gene between cp45 and wild-type HPIV-3 (JS).

SEQ ID NO. 3 list the amino acid sequence for the HN protein of HPIV-3 strain (JS). The cp45 strain differs from this sequence by the substitution of Ala for Val at position 384.

SEQ ID NO. 4 lists the coding strand nucleic acid sequence for the HN protein of HPIV-3 strain (JS). The cp45 strain differs form this sequence by the substitution of C for T at position 6847, and the substitution of C for T at position 7956.

SEQ ID NO. 5 lists the nucleic acid sequence of a primer used for amplification of RNA samples in Example 1.

SEQ ID NO. 6 lists the nucleic acid sequence of a primer used for amplification of RNA samples in Example 1.

SEQ ID NO. 7 lists the nucleic acid sequence of a primer used for amplification of RNA samples in Example 1.

SEQ ID NO. 8 lists the nucleic acid sequence of a primer used for amplification of RNA samples in Example 1.

DETAILED DESCRIPTION OF THE INVENTION

As used herein, the term "HPIV-3" means human parainfluenza-type 3 and includes all HPIV-3 strains, including all wild-type HPIV-3 strains and attenuated strains such as cp45. The term "wild-type HPIV-3" refers to wild-type strains and excludes attenuated mutant strains. "HPIV-3 (JS)" or "JS strain" refers to the wild-type JS strain of HPIV-3. (Belshe and Hissom 1982). The term "cp45" refers to the attenuated, temperature-sensitive and cold-adapted cp45 strain of wild-type HPIV-3 (JS), deposited with the American Type Culture Collection (ATCC) (Rockville, Md.), Accession No. VR-2548. The contents of each of the references cited herein are hereby incorporated by reference in their entirety.

The present invention is based upon correlation of two attenuating lesions of the cp45 strain to specific genetic defects in the viral genome of cp45. Specifically, it is now understood that a significant level of attenuation of cp45 giving rise to its temperature-sensitive and cold-adapted phenotypes is directly associated with mutation of the large, or L, gene of cp45 relative to the corresponding gene in the wild-type JS strain. Moreover, it is further understood that a second attenuating lesion exists independently of the temperature-sensitive lesion, and is directly associated with mutation of the hemagglutinin-neuraminidase gene, or [HN] gene, of cp45 relative to the corresponding gene in the wild-type HPIV-3 (JS) strain. The correlation of these two attenuating lesions of cp45 to specific genes enables several practical applications. It is now possible to create vaccines directed at other wild-type HPIV-3 viruses and, additionally, vaccines directed at target viruses other than HPIV-3 using genetic engineering techniques. For example, the mutated L and/or HN genes of cp45 can be incorporated into the viral genome of a target virus. Alternatively, the genes of the target virus which encode its surface antigens can be incorporated into the viral genome of cp45. Moreover, it is possible to determine whether an HPIV-3 strain or a hybrid virus strain made by the methods disclosed herein is attenuated by confirming the presence or absence of mutations in its L and/or HN genes. A verification of attenuation is desirable before administration as a check of new vaccine lots and also after such administration to ensure the stability (i.e., non-reversion) of the vaccine virus. The hybrid viruses described herein are also useful for studying the effect of and role of mutant L and HN genes and the corresponding variant L and HN proteins on the processes of viral infection, reproduction, and spread in cells.

HPIV-3 is an enveloped, negative-sense, single-stranded RNA virus. Its viral genome encodes at least six structural proteins, including, in succession from the 3' end: [3'-NP-P(+C)-M-F-HN-L-5'], wherein 3' refers to the 3' leader region of the genome and wherein NP, P(+C), M, F, HN, and L refer to the regions of the genome which encode the nucleocapsid protein, the phosphoprotein, the matrix protein, the fusion protein, the hemagglutinin-neuraminidase protein, and the large protein, respectively. (Spriggs and Collins 1986; Storey et al 1984). Relatively short, non-coding intergenic regions separate each of the regions encoding functional proteins.

The nucleocapsid protein, NP, is the most abundant structural protein. It encapsidates the genomic RNA and is believed to maintain the structural integrity and template function of the genome. The L protein functions as the RNA-dependent RNA polymerase, and the P protein functions as an auxiliary regulatory protein which supports the function of L. The P(C+) gene also contains a (C+) reading frame. The matrix, fusion, and hemagglutinin-neuraminidase proteins, M, F and HN, respectively, collectively form the lipid envelope which surrounds the nucleocapsid core. M forms the structural internal portion of the envelope, while F and HN are surface glycoproteins. The hemagglutinin or H portion of the HN protein and the F protein are responsible for attachment onto and penetration into a host cell by HPIV-3, while the neuraminidase or N portion of the HN protein is responsible for release of the progeny viruses from the host cell after replication.

During reproduction of paramyxoviruses such as HPIV-3 in the cytoplasm of infected cells, the nucleocapsid (RNA-NP) serves as a template for transcription by the viral RNA polymerase, L. L and P proteins are both associated with the RNA-NP core, and during primary transcription, the L-P complex interacts with the nucleocapsid core to transcribe the genomic RNA into individual mRNAs which code for viral proteins. In addition, during replication in an infected cell, NP may form a soluble complex with P. This complex is thought to interact with transcribing nucleocapsid complexes to switch from primary transcription to replication of the viral RNA.

The complete nucleic acid sequences of the wild-type HPIV-3 (JS) genome and of the temperature sensitive cp45 genome are known and have been compared. (Stokes et al. 1993; Galinski et al. 1988; Galinski et al. 1986; Galinski et al. 1986'; Spriggs and Collins 1986; Spriggs and Collins 1986'; Storey et al. 1984). At least 18 nucleotide differences exist between wild-type HPIV-3 (JS) genome and the cp45 genome, as shown in FIG. 1. However, nine of these 18 nucleotide changes are found in non-attenuated strains or do not result in amino acid changes in the proteins which they encode. Two of the remaining changes are in the non-coding 3'leader region, but may be important for regulation. Hence, at least seven remaining nucleotide differences between the cp45 genome and the wild-type genome are known to result in amino acid sequence changes in four variant proteins: M, F, HN and L. The changes in amino acid sequences of the variant cp45 proteins relative to the corresponding wild-type JS proteins include: in the M gene, substituting threonine (Thr) for proline (Pro) at residue 199; in the F gene, substituting valine (Val) for isoleucine (Ile) at residue 420 and threonine (Thr) for alanine (Ala) at residue 450; in the HN gene described in SEQ ID NO. 2, substituting alanine for valine at residue 384; and in the L gene described in SEQ ID NO. 1, substituting histidine (His) for tyrosine (Tyr) at residue 942, phenylalanine (Phe) for leucine (Leu) at residue 992 and isoleucine (Ile) for threonine (Thr) at residue 1558.

The variations in the region of the wild-type HPIV-3 (JS) genome which encodes the L protein are now understood to directly correlate to the temperature sensitive phenotype of the cp45 strain. That is, the temperature sensitive phenotype of the cp45 strain of HPIV-3 (JS) is caused by a mutation in the large, or L, gene of cp45 relative to the corresponding gene in the wild-type JS strain. The L gene encodes the RNA-dependent RNA polymerase of the HPIV-3 virus. The gene product of the mutant L gene, referred to herein as a variant L protein, has a decreased polymerase activity relative to that of the wild-type JS strain at higher, non-permissive temperatures. Such decreased polymerase activity results in reduced transcription of the viral RNA and reduced synthesis of viral proteins. Some reduction in transcriptional activity is observed beginning at about 37° C., and a marked reduction occurs at or above about 38° C. Hence, the non-permissive temperatures for cp45 are considered to be temperatures greater than about 37° C., and generally ranging from about 37° C. to about 40° C. Without being bound by theory, it is believed that higher temperatures and, in addition, Ph changes developed in certain cellular compartments due to such higher temperatures cause conformational changes in the mutant RNA-dependent RNA polymerase. Specifically, the His and Phe substitutions in the L protein, at residues 942 and 992 of SEQ ID NO. 1, respectively, are believed to be important contributors to the presence of the temperature sensitive phenotype. Histidine-phenylalanine interactions are Ph dependent, and intracellular Ph changes are affected by temperature. A shift to the higher non-permissive temperatures and a corresponding change in Ph results in histidine-phenylalanine interactions which cause conformational changes in the RNA dependent RNA polymerase (L protein). Such conformational changes, in turn, result in a decreased activity of the polymerase and a corresponding decrease in transcription and replication. Because the observed decrease in polymerase activity is not observed at lower, permissive temperatures, a virus having the variant L protein will be attenuated and will exhibit the characteristic temperature sensitive phenotype, thereby making it suitable for use as a vaccine. The wild-type RNA-dependent RNA polymerase does not appear to undergo such temperature sensitive conformational changes.

The temperature-dependent replication of the cp45 strain clearly contributes to the observed attenuation in the cp45 vaccine. As shown in Table 1, replication of the temperature sensitive cp45 strain is reduced by a factor of about $10^6$ as compared to replication of the wild-type ("WT") JS strain. (Example 1). cp45 showed some replication upon shifting the incubation temperature from 39.5° C. to 32° C. after 24 hours at the higher temperature, and hence demonstrated the characteristic temperature-sensitive phenotype. The poor transcriptional activity of the cp45 virus strain results in markedly reduced MRNA synthesis at 39.5° C., and as a result, protein synthesis and virus growth are significantly affected. (Example 1).

TABLE 1

Comparison of yields of cp45 and parent wild-type (WT) viruses in a temperature-shift experiment

| Virus Strain | Incubation Temp (° C.) | Virus yield[a] |
|---|---|---|
| cp45 | 32 | $2.9 \times 10^7$ |
| WT | 32 | $1 \times 10^7$ |
| cp45 | 39.5 | $1.2 \times 10^1$ |
| WT | 39.5 | $8 \times 10^6$ |
| cp45 | 39.5 → 32[b] | $2 \times 10^3$ |
| WT | 39.5 → 32[b] | $1.5 \times 10^7$ |

[a]Virus yields in L-132 cells, infected at similar multiplicities of infection, are expressed after 48 h of incubation.
[b]Temperature shift.

The temperature dependent activity of the cp45 RNA-dependent RNA polymerase (L protein) and the corresponding reduced transcription of cp45 at non-permissive temperatures (about 40° C.) is associated with variations in the region of the viral genome which encodes the L protein. Whereas a cell infected with cp45 alone does not replicate significantly, cells which were co-transfected with cp45 and a recombinant DNA vector which expressed wild-type L protein showed significant levels of replication. (Examples 4 and 5). Table 2 reports virus replication yields of complementation plaque assays done on L-132 cells. Briefly, CV-1 cells were cotransfected with plasmid DNA (pRSV-T) encoding the SV40 large T antigen and the recombinant plasmid DNAs (L, P, and/or NP). The CV-1 cells were then infected with cp45 virus at 20 hours post-transfection and incubated at 39.5° C. for 28 hours. As shown in Table 2, when the temperature sensitive cp45 strain is complemented by non-mutant wild-type L protein in a complementation assay, the level of replication, as measured by plaque assay methods, increased by a factor of more than 100 relative to the uncomplemented cp45. In contrast, complementation of the cp45 strain with wild-type P protein or with wild-type NP protein had no effect on replication. Cells cotransfected with cp45 and with wild-type L and P proteins, or with wild-type L, P and NP proteins, showed similar increases in yield over cells cotransfected with cp45 and wild-type L protein alone, thereby indicating the key role of the L protein.

TABLE 2

Complementation assay for recovery of cp45 virus at the nonpermissive temperature (39.5° C.)

| Gene(s) used in complementation | Virus recovery titer (PFU/ml of culture medium) at 32° C. |
|---|---|
| None | <1.0 |
| L, P, and NP | $2.3 \times 10^3$ |
| L and P | $1.9 \times 10^2$ |
| L | $3.3 \times 10^2$ |
| P | <1.0 |
| NP | <1.0 |

Importantly, cp45 progeny virus produced from co-transfected cells in which wild-type L protein was used to complement the cp45 strain at non-permissive temperatures retained the temperature sensitive phenotype of the parent cp45 strain. (Example 6). Further, the L protein complementation of cp45 is heterotypically exclusive. (Example 6). Hence, the recovery of cp45 replication at higher, non-permissive temperatures by complementing the cp45 strain with wild-type L protein demonstrates that the variant L protein (RNA-dependent RNA polymerase) is responsible for the temperature sensitive phenotype of cp45. While other attenuating lesions also contribute to attenuation of cp45, the contribution of the variant L protein is particularly significant.

A second attenuating lesion of the cp45 strain has been linked to a mutation in the hemagglutinin-neuraminidase gene, or [HN] gene, of cp45 relative to the corresponding gene in the wild-type HPIV-3 (JS) strain. The HN gene encodes a protein having both hemagglutinin activity and neuraminidase activity. The gene product of the mutant HN gene, referred to herein as a variant HN protein, has decreased neuraminidase activity relative to the HN protein of the wild-type (JS) strain. There is a substitution of alanine for valine at amino acid residue 384 of the HN protein. The decreased neuraminidase activity, which may be due to a conformational change attributable to this amino acid substitution, inhibits the release of progeny virus from infected host cells, thereby slowing and reducing the extent to which the virus spreads to and replicates in other cells.

Figure 7A:
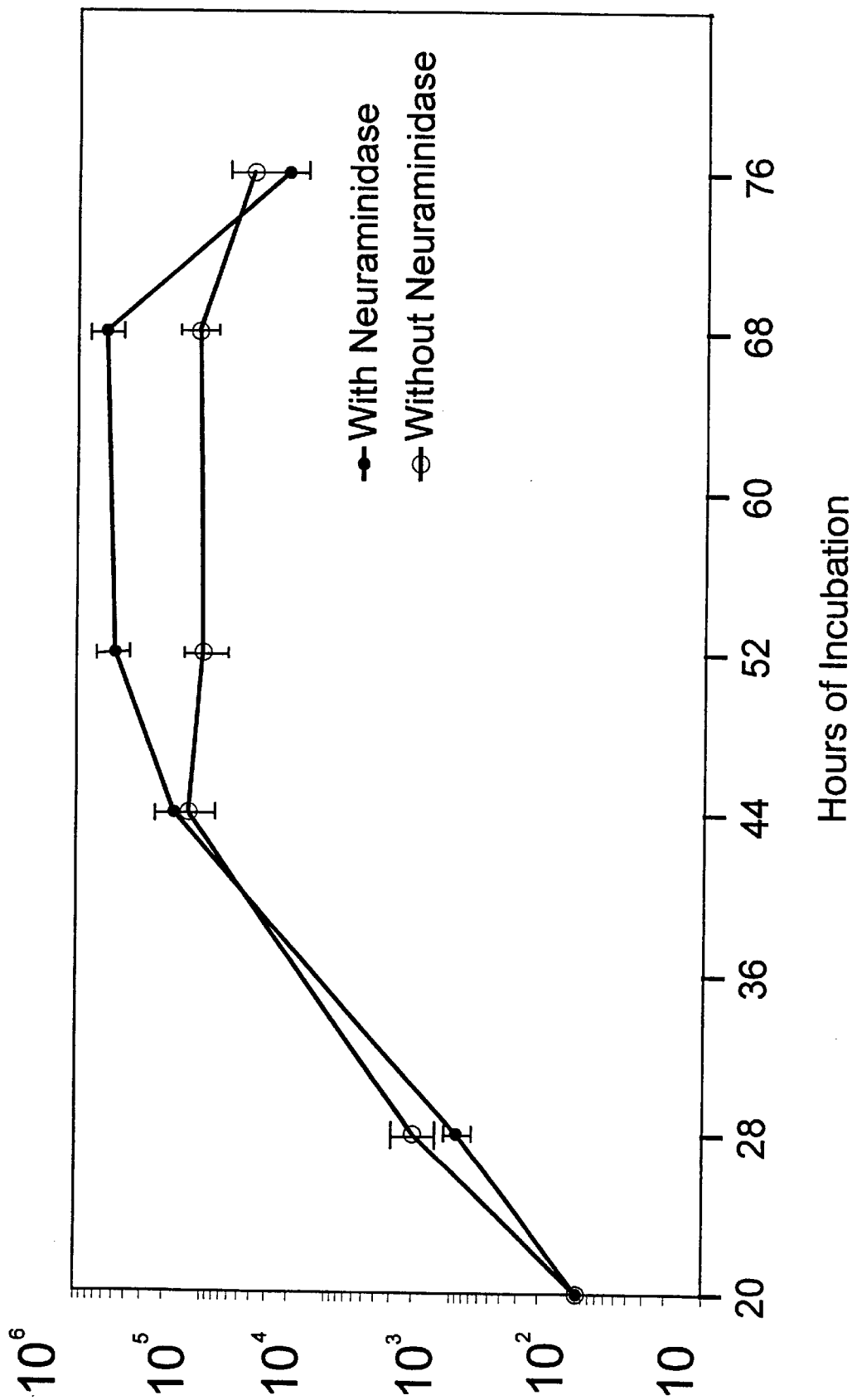
Figure 7B:
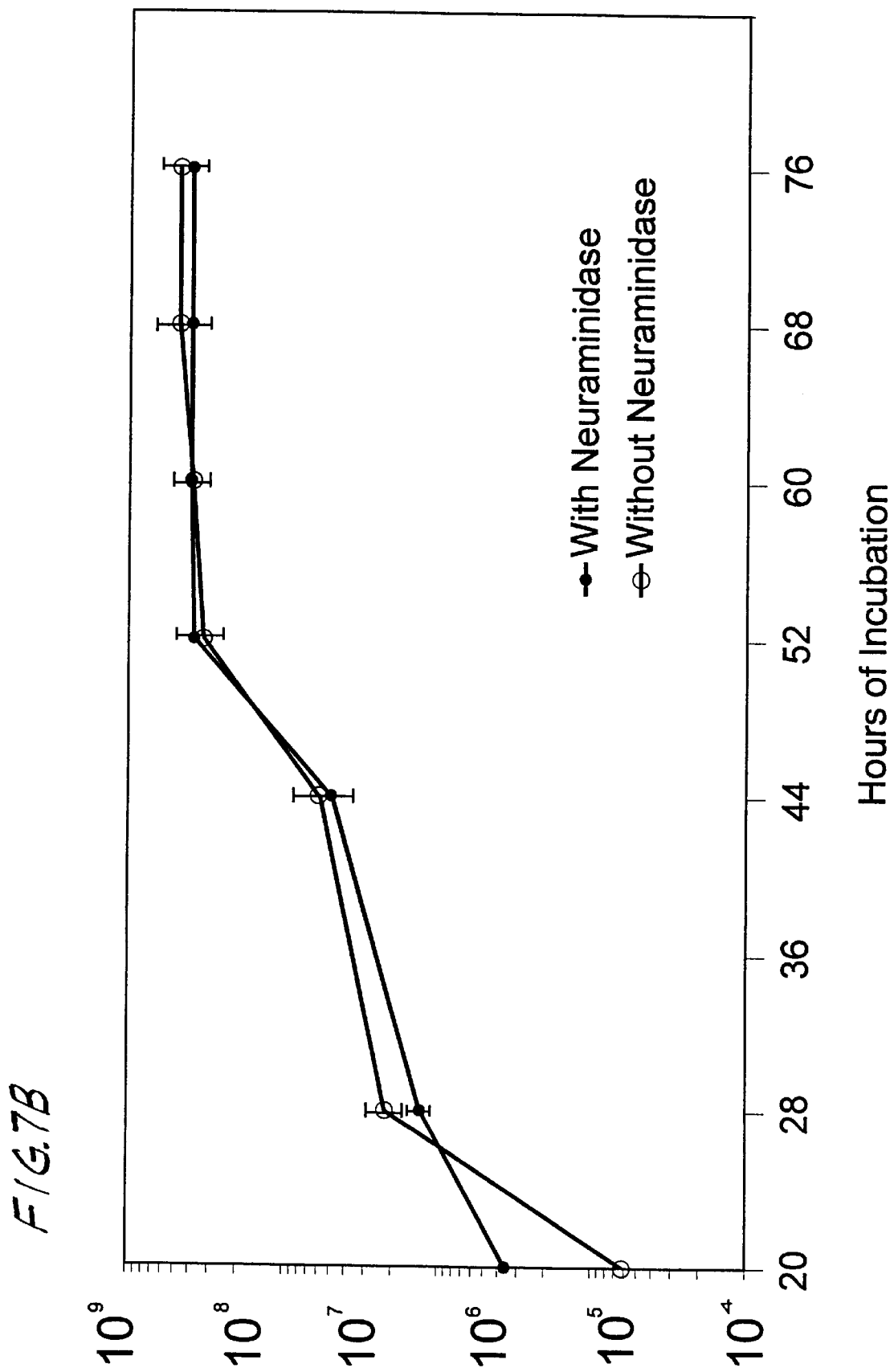

Several experiments demonstrate that reduced neuraminidase activity is directly associated with the variant HN protein and is independent of and complementary to the temperature sensitive lesion associated with the variant L protein. Growth characteristics of cp45 and wild-type (JS) virus strains at 32° C. were determined in cultures in which exogenous neuraminidase was either absent or present. (Example 7). As shown in FIG. 7A, cp45 virus titers taken after about 50 hours of incubation in a culture medium lacking exogenous neuraminidase were about five to fifteen times lower than corresponding titers taken after incubation in a culture medium containing exogenous neuraminidase. In contrast, wild-type JS virus titers were virtually identical after about 25 hours regardless of whether or not exogenous neuraminidase was present in the culture medium. (FIG. 7B).

Figure 8A:
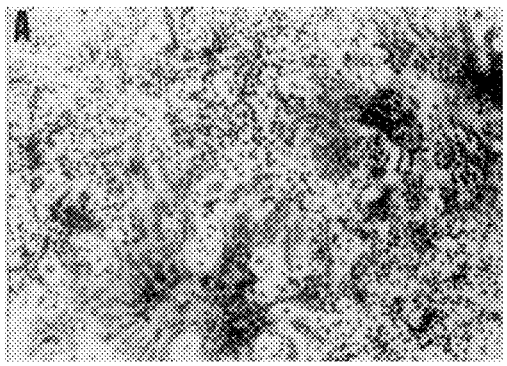
Figure 8B:
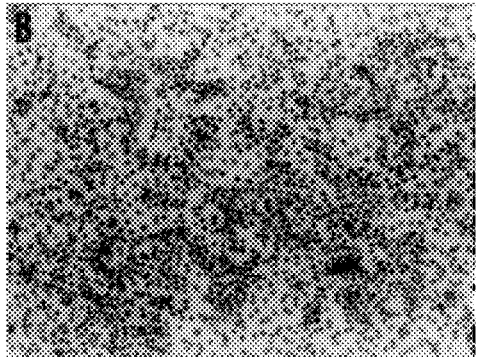
Figure 8C:
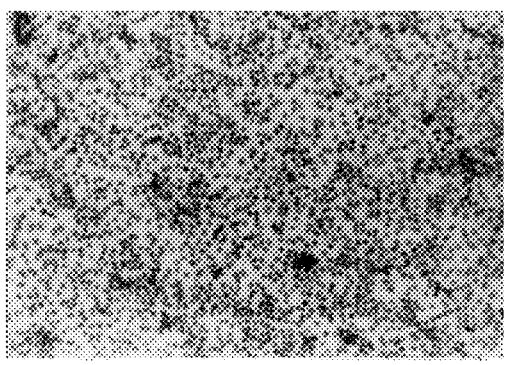
Figure 8D:
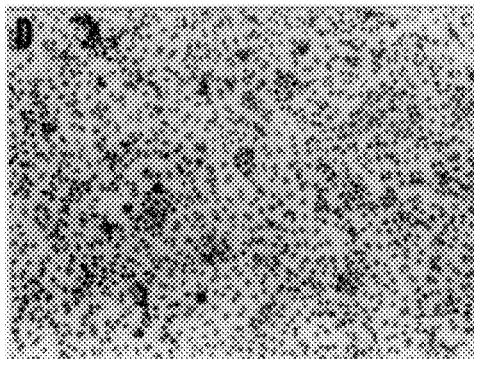
Figure 9A:
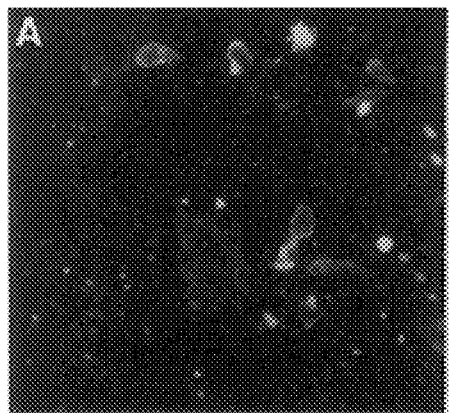
Figure 9B:
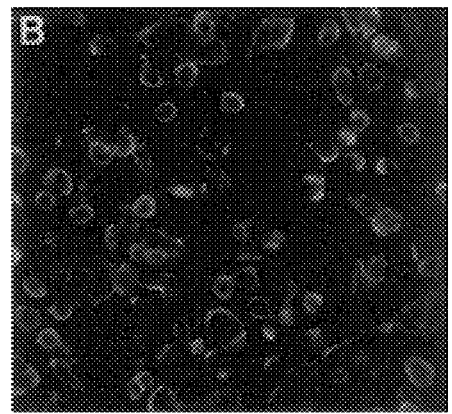
Figure 9C:
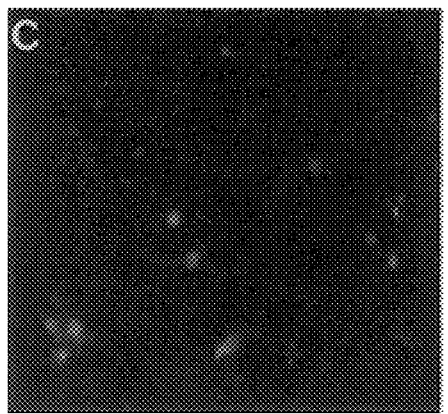
Figure 9D:
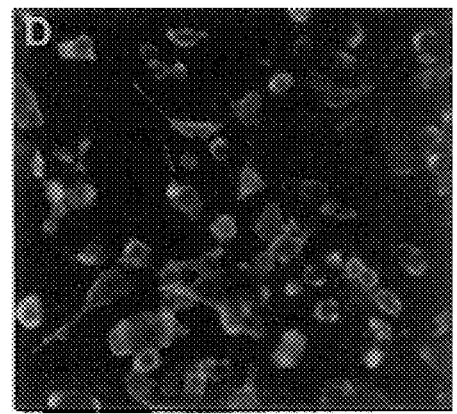

Moreover, L-132 cells infected with cp45 at a low multiplicity of infection and grown at 32° C. exhibited localized cell fusion with characteristic multinucleated giant cell or syncytia formation. (FIG. 8A; Example 8). Consistently, the distribution of the variant HN protein expressed in L-132 cells infected with cp45 at 33° C. was restricted to localized areas. (FIG. 9A; Example 9). However, the addition of exogenous neuraminidase to the culture medium in experiments which paralleled each of the two immediately aforementioned experiments resulted in a dramatic reduction in both the degree of localized cell fusion (FIG. 8C) and the extent of restricted and localized distribution of the variant HN protein (FIG. 9C). The cytopathic effect observed in cp45 infected cells incubated in the presence of exogenous neuraminidase was similar to that observed in JS infected cells, which exhibited significantly less localized cell fusion regardless of whether they were incubated in the absence of (FIG. 8B) or presence of (FIG. 8D) exogenous neuraminidase. Uniform and similar distribution of the wild-type JS HN glycoprotein was observed in the absence of (FIG. 9B) or presence of (FIG. 9D) exogenous neuraminidase. The absence of fusion promotion activity following addition of bacterial neuraminidase in the culture medium indicates that fusion of cp45 is associated with its neuraminidase activity. The restricted distribution of the variant HN protein in the culture media and the extensive localized cell fusion exhibited by the virus having the variant HN protein indicates that the release of viral progeny from the infected cell is reduced relative to cells infected with the wild-type JS strain, and that multi-cell replication of the virus is inhibited by the variant cp45 HN protein.

Neuraminidase activity studies suggest a conformational change in the cp45 variant HN protein relative to the HN protein of the wild-type JS strain. Referring to Table 3, a decrease in neuraminidase activity of the cp45 strain relative to the JS strain is exhibited at both the non-permissive (39.5° C.) and permissive (32° C.) temperatures. (Example 2). At the higher, non-permissive temperature, the cp45 neuraminidase activity differed from that of the JS strain regardless of whether fetuin or neuraminlactose was used as the assay substrate. At the lower, permissive temperature however, a difference in neuraminidase activity for the two strains was observed only in assays using fetuin as a substrate. No difference was observed at the permissive temperature between the activity of the cp45 and JS strains when the assay used the relatively smaller neuraminlactose substrate. The observed substrate dependency suggests that the tertiary structure of the neuraminidase-activity-conferring portion of the HN protein for cp45 appears to be different from that of the JS strain.

TABLE 3

Comparison of neuraminidase activities of cp45 and parent wild-type (WT) viruses

| Virus strain | Incubation temp (° C.) | HA[a] units used | Neuraminidase activity with[b]: | |
|---|---|---|---|---|
| | | | Fetuin | Neuraminlactose |
| WT | 39.5 | 512 | 0.24 | 3.60 |
| cp45 | 39.5 | 512 | 0.03 | 0.83 |
| WT | 32 | 2,048 | 1.11 | 2.30 |
| cp45 | 32 | 2,048 | 0.67 | 2.30 |

[a]HA = hemagglutinin activity.
[b]Results are presented as optical density values at 549nm.

Figure 10A:
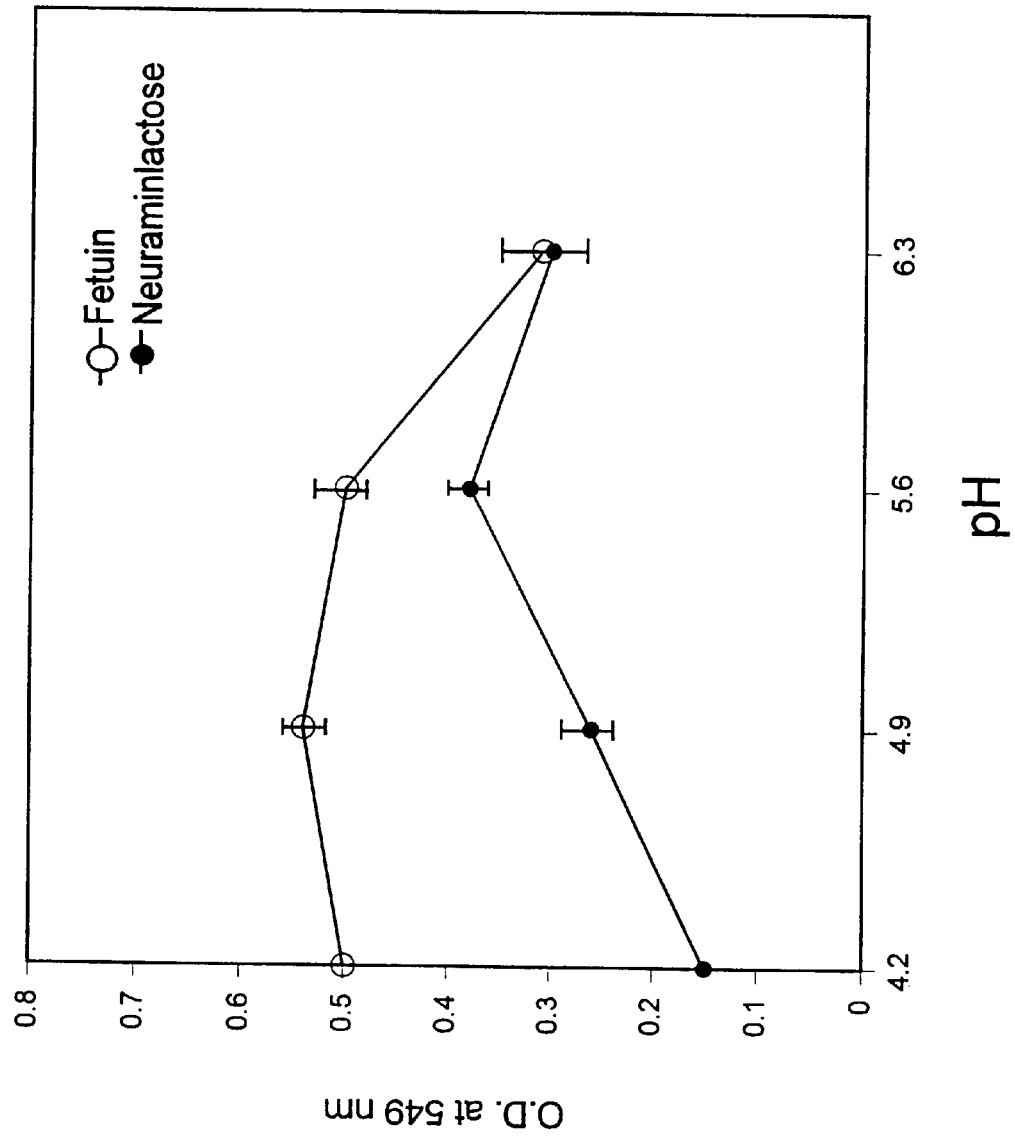
Figure 10B:
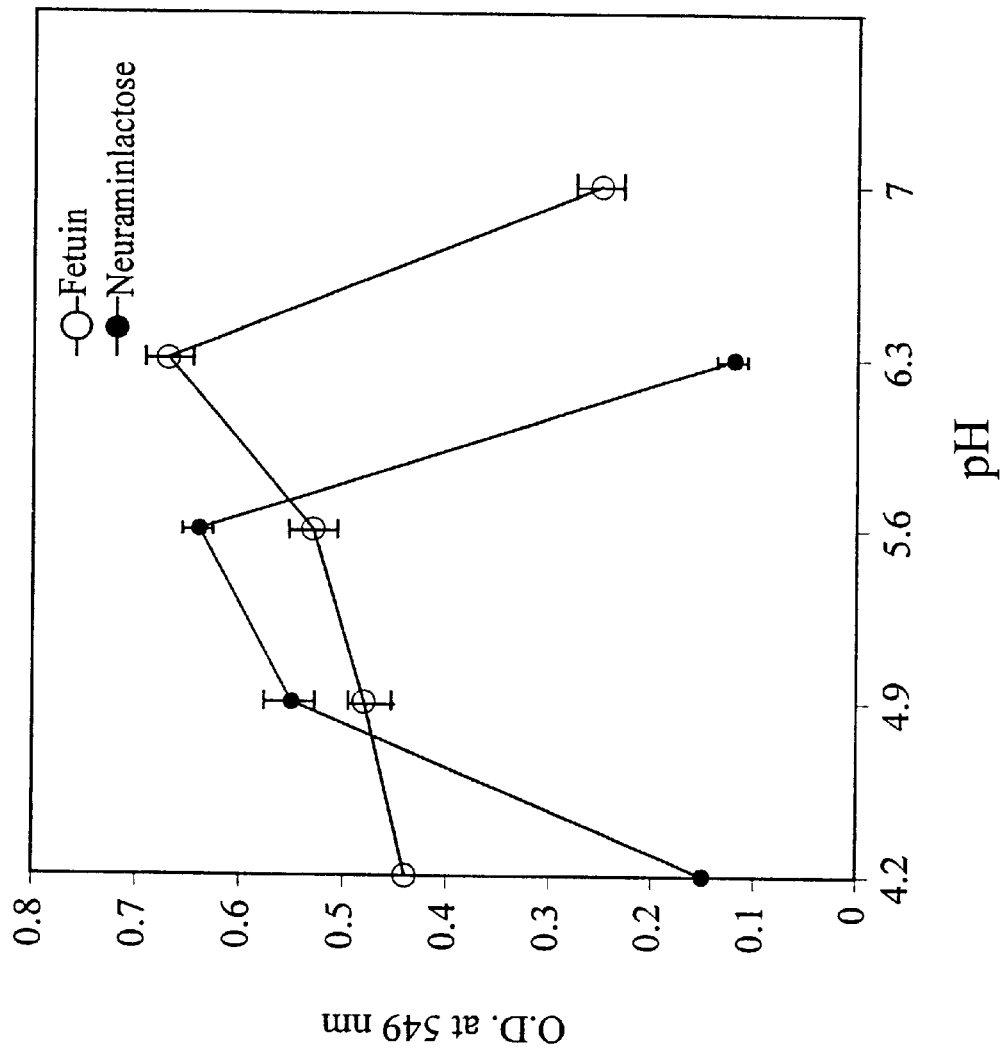
Figure 11A:
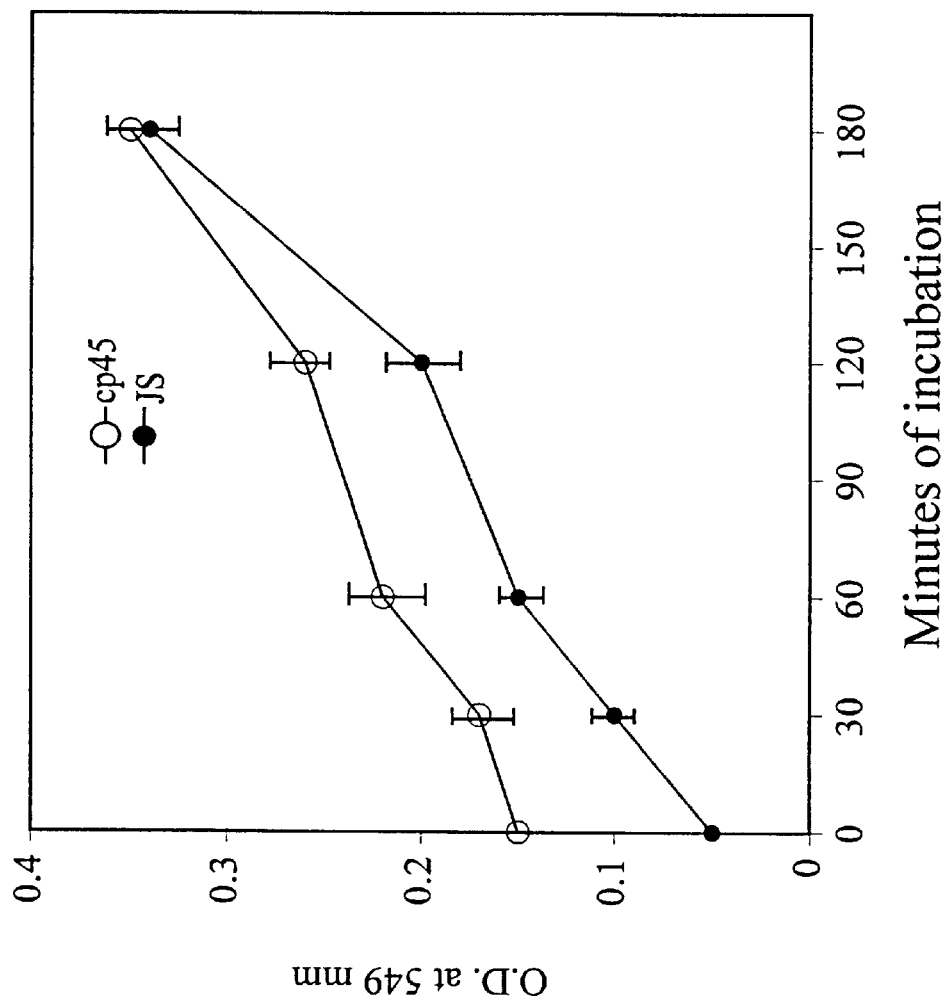
Figure 11B:
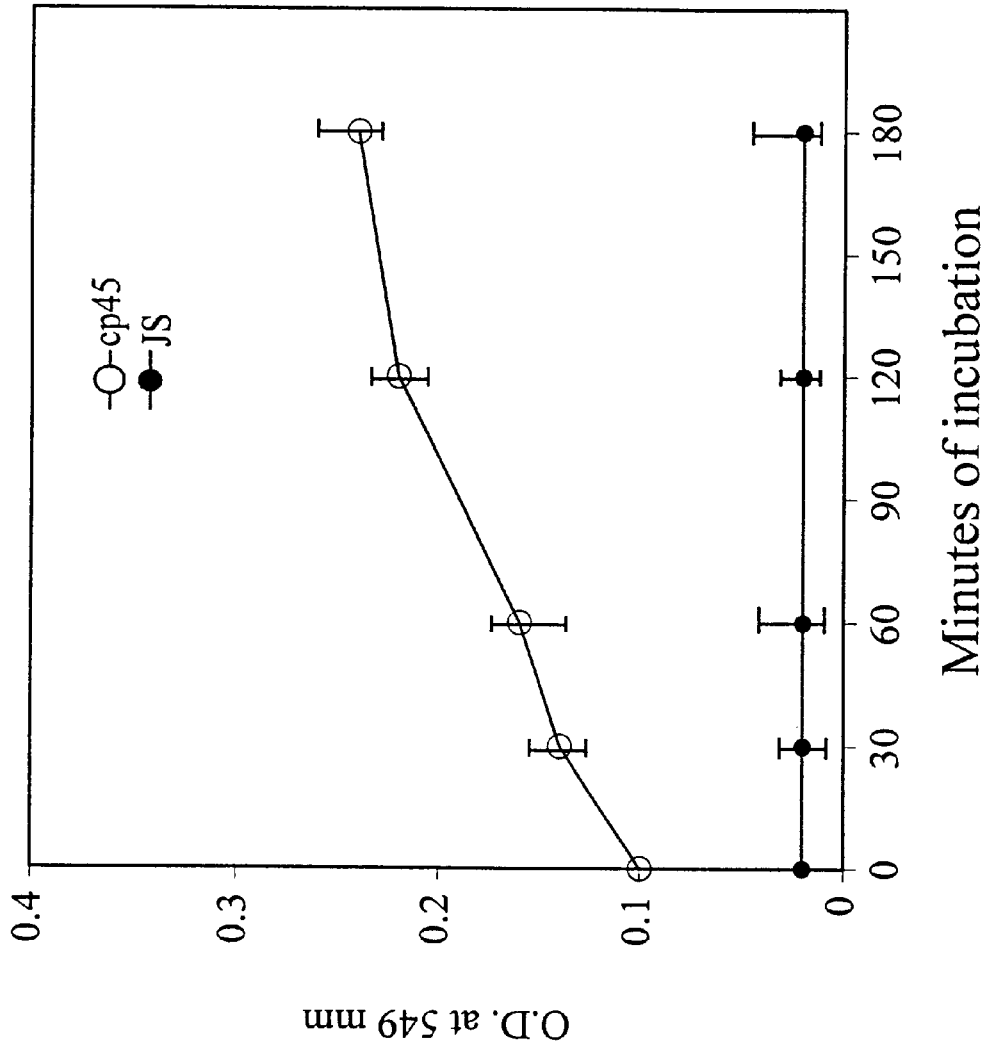

Additional differences in enzymatic properties were observed in further neuraminidase studies. The pH optima of neuraminidase activity in cp45 and JS strains were compared using neuraminidase activity assays with either fetuin or neuraminlactose as the assay substrate. (Example 10). As seen by comparing the data in FIGS. 10A and 10B, when the neuraminidase activity is assayed with the smaller substrate, neuraminlactose, the optimal pH for the cp45 and JS strains was the same—about 5.5. However, when assayed with the larger substrate, fetuin, the optimal pH for cp45 was about 4.9, whereas the optimal pH for the JS strain was about 6.3. Without being bound by theory, a lower pH optimum for neuraminidase activity of cp45 as compared to that of wild-type HPIV-3 (JS) is consistent with the variant HN protein being an attenuating lesion of cp45 where in-vivo HPIV-3 infection initiates in regions of the respiratory tract which have a pH which is closer to the optimal pH of the wild-type JS strain than the optimal pH of cp45. In an enzymatic kinetic study, the neuraminidase activities of cp45 and JS strains were determined using assays having neuraminlactose substrates with either 2→3 or 2→6 linkages. (Example 10). The kinetic studies were conducted at a pH of 5.5, shown to be optimal for neuraminlactose. Comparison of the rate of change in activity for the cp45 and JS strains indicates that both ;strains have a similar preference for the 2→3 linkage (FIG. 11A), whereas cp45 has a greater preference than the JS strain for the 2→6 linkage. (FIG. 11B). Moreover, cp45 has a greater preference for the 2→3 linkage than for the 2→6 linkage. (Compare FIG. 11A and FIG. 11B).

Without being bound by theory, the results of the experiments involving neuraminidase activity assays cumulatively indicate that the variant HN protein of cp45 has an altered tertiary structure as compared to that of HPIV-3(JS) and that activity of the variant HN protein is likely temperature, pH, substrate and/or linkage dependent. The decrease in neuraminidase activity restricts the release of the progeny virus particles from the infected cell surface. However, the decrease in activity by a factor ranging from about five to about 10 suggests that the variant HN protein is a relatively less important contributing lesion as compared to the variant L protein. Moreover, nucleotide changes in the 3' leader region of cp45 relative to the that of the wild-type strain are also suspected of affecting the cold adaptive, temperature sensitivity and/or attenuation properties of cp45.

Figure 12A:
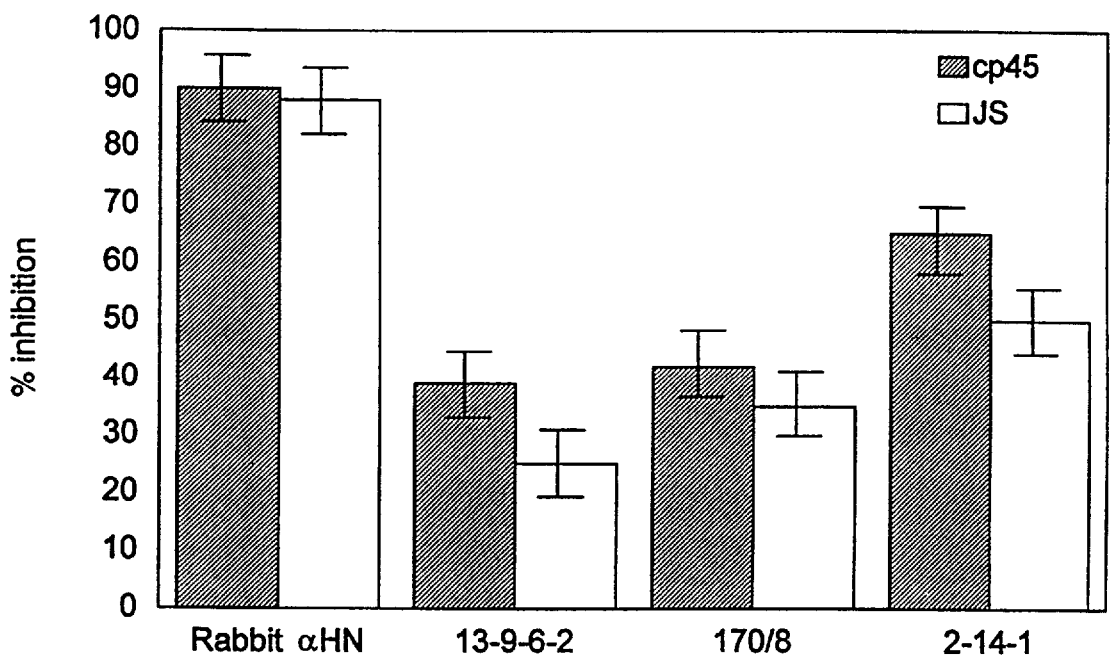
Figure 12B:
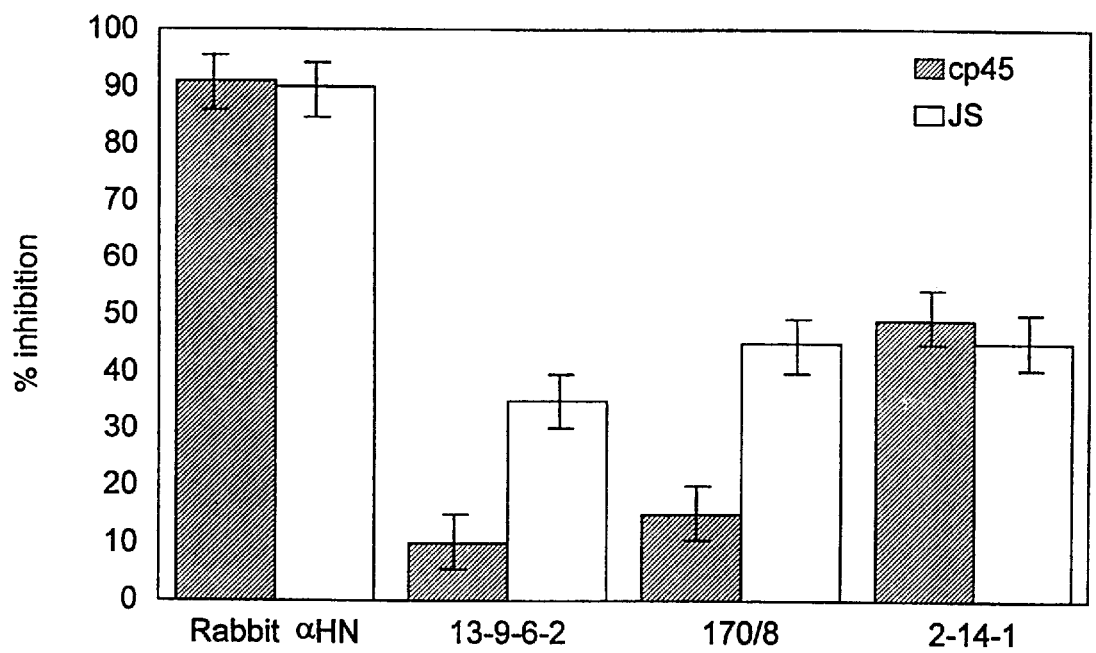

Although the transcriptional activity and neuraminidase activities of cp45 are reduced relative to those of wild-type HPIV-3, other biological properties were not significantly altered. Early studies indicated that the antigenic sites of the envelope glycoproteins, defined by reactivity to a panel of monoclonal antibodies remained unaffected in cp45 as compared to the wild-type strain. (Example 3). However, some modulation of the surface antigens of cp45 was indicated in further studies in which the antigenic relatedness of the neuraminidase active sites of cp45 and HPIV-3 (JS) was compared using antibodies and antiserum known to inhibit the neuraminidase activity of wild-type HPIV-3. Inhibition of cp45 and HPIV-3 (JS) neuraminidase activity was tested with three monoclonal antibodies (2-14-1, 13-9-6-2 and 170/8) and with a monospecific rabbit antiserum to affinity purified HN. (Example 11). When fetuin was used as the substrate for determining inhibition of neuraminidase activity, no significant difference in antigenic sites between cp45 and HPIV-3 (JS) was observed for any of the inhibiting antibodies or antisera. (FIG. 12A). When the relatively smaller neuraminlactose substrate was used however, the neuraminidase activity of the cp45 strain was less inhibited than the activity of the JS strain by the monoclonal antibodies 12-9-6-2 and 170/8. (FIG. 12B). The extent of inhibition of neuraminidase activity in the two strains was similar for the monoclonal antibody 2-14-1 and for the monospecific rabbit antisera. (FIG. 12B). Without being bound by theory, the variation in amino acid sequence of the enzymatic site of the cp45 HN protein appears to have caused minor changes to the antigenic sites recognized by monoclonal antibodies 12-9-6-2 and 170/8, but has not had a detectable effect on other antigenic sites, including for example, the antigenic site recognized by the 2-14-1 antibody. Nonetheless, the variant HN protein retains the capability to elicit an immune response specific for HPIV-3, despite the minor change in conformational epitope. Similarly, transport of HN and F glycoproteins to the cell surface, and the hemagglutinin activity of the HN protein, determined by an hemagglutinin activity assay, were not substantially different for the cp45 strain relative to the wild-type JS strain. (Example 3). Further, limited viral morphogenesis was observed at the nonpermissive temperature.

The attenuating lesions associated with mutations of the L gene and the HN gene of cp45 can be used to create vaccines directed at other wild-type HPIV-3 viruses and, additionally, vaccines directed at target viruses other than HPIV-3. In general, target viruses can include any enveloped virus that has one or more surface antigen. As used herein, the term "surface antigen" refers to a protein or a portion thereof which is capable of generating an immune response in vivo, and generally includes surface proteins, surface glycoproteins and/or other moieties which are responsible for the attachment of the viruses onto host cells, which allow the viruses to penetrate into the host cells to establish infection, and/or which facilitate release of progeny virus from the infected host cells. Surface antigens of various viruses or virus strains are considered "different" from each other if they have different antigenic sites such that they generate different in vivo immune responses. For purposes herein, differences can be demonstrated using in vitro assays showing that the surface antigens are selectively screened or selectively inhibited by different antibodies. The target virus will generally be a wild-type strain, but could also include mutant viruses against which it is desirable to use a live, attenuated vaccine.

Preferred target viruses include related enveloped, negative-sense, single-stranded RNA viruses such as human parainfluenza virus type 1 (HPIV-1), human parainfluenza virus type 2 (HPIV-2), respiratory syncytial virus (RSV), human influenza virus type A, human influenza virus type B, mumps and measles viruses. Target viruses such as HPIV-1, HPIV-2, RSV, influenza and measles each have surface proteins which are involved with the viruses' attachment to and penetration into a host cell, and which can be considered functionally analogous to the F and HN proteins of HPIV-3. The nucleic acid sequences for encoding the surface proteins for each of these viruses are known. HPIV-1 and HPIV-2, like HPIV-3, each have two surface glycoproteins, HN and F, which are functionally similar to HPIV-3's HN and F proteins. For both type 1 and type 2 parainfluenza viruses, the H portion of the HN protein and the F protein are related to attachment and penetration, respectively, while the N portion of the HN protein is responsible for release of progeny virions. The nucleic acid sequences of the F gene and HN gene for HPIV-1 have been previously determined. (Merson et al. 1988; Matsuoka et al. 1990). The nucleic acid sequences of the F gene and the HN gene for HPIV-2 have likewise been determined. (Hu et al. 1990; Precious et al. 1990; Kawano et al. 1990'; Kawano et al. 1990). RSV-A and RSV-B each have two surface glycoproteins, F and G. The G protein is functionally analogous to the hemagglutinin activity of HPIV-3's HN protein; it has activities related to attachment onto a host cell. F is related to penetration of the nucleocapsid into the host cell. The nucleic acid sequences of the F gene and G gene for RSV-A have been determined. (Lopez et al. 1988; Martin-Gallardo et al. 1991; Anderson et al. 1992; Martin-Gallardo et al. 1993; Collins et al. 1993). The nucleic acid sequences of the F gene and G gene for RSV-B have also been previously determined. (Baybutt and Pringle 1987; Sullender et al. 1990; Sullender et al. 1991). These sequences or portions thereof have also been extensively compared. (Johnson and Collins 1988; Johnson and Collins 1988'). Influenza types A and B also have two surface glycoproteins: H and N. The H protein has activities related to attachment and penetration onto and into a host cell. The N protein relates to release of progeny virions from the infected host. Although the antigenic sites for influenza viruses typically change every year or so, samples of current strains are readily available from the U.S. Center for Infectious Disease Control, and the nucleic acid sequences defining the current surface glycoproteins can be determined therefrom. Measles viruses also have two surface glycoproteins: HN and F. Like HPIV-3, the H portion of the HN protein and the F protein are related to attachment and penetration, respectively, while the N portion of the HN protein is responsible for release of progeny virions. Bovine RSV has two surface glycoproteins which are functionally analogous to the human RSV strains. The nucleic acid sequences for bovine RSV G and F glycoproteins have been determined. (Lerch et al. 1990; Walravens et al. 1990). While target viruses related to HPIV-3 by virtue of their molecularly and functionally similar surface proteins are preferred, the target viruses of the present invention can also include other enveloped viruses, such as other paramyxoviruses, other orthomyxoviruses, retroviruses (e.g. human immunodeficiency viruses, HIV, which have, for example, surface proteins with attachment functions (HIV-GP120) and penetration functions (HIV-GP41)), arenaviruses, coronaviruses, bunyaviruses, rhabdoviruses, togaviruses, herpesviruses, poxviruses and hepadnaviruses. Preferable target viruses include enveloped viruses which reproduce in the cytoplasm. The target virus of the present invention may be specific to humans, specific to animals or common to both animals and humans. Bovine RSV and cattle HPIV-3 (shipping fever virus) are typical animal viruses included within the scope of the present invention.

Vaccines directed at HPIV-3 viruses can be created by using genetic engineering techniques to create a hybrid virus which is preferably an enveloped, negative-sense, single-stranded RNA virus. Such a hybrid virus can be created, in general, by replacing the wild-type L and/or HN genes in the genome of the target virus with L and/or HN genes which are mutated relative to the target virus and which encode variant L and/or HN proteins having reduced polymerase and/or neuraminidase activity, respectively. The hybrid virus is then combined with a pharmaceutically acceptable carrier to form an attenuated vaccine.

A hybrid virus suitable for use in a vaccine against an HPIV-3 target virus has a chimeric viral genome which comprises a nucleic acid sequence which is the same as the nucleic acid sequence of the 3' leader region of the HPIV-3 target virus or which encodes one or more of the following proteins: the nucleocapsid protein [NP], the phosphoprotein [p(+C)], the matrix protein [M], and/or the fusion protein [F] of the wild-type HPIV-3 target virus. The viral genome further comprises HN and L genes. The HN gene of the viral genome can encode either the wild-type HN protein of the target virus or a variant HN protein having a neuraminidase activity which is less than the neuraminidase activity associated with the HN protein of the target virus at a temperature of about 39° C. Similarly, the L gene of the viral genome can encode either the wild-type L protein of the target virus or a variant L protein having an RNA-polymerase activity which is less than the RNA-polymerase activity associated with the L protein of the target virus at a temperature of about 39° C. In any case, either the HN gene or the L gene of the hybrid virus encodes a variant protein, such that the hybrid virus has at least one attenuating lesion (based on either the variant HN or the variant L proteins) relative to the wild-type HPIV-3 virus.

In one embodiment, the genome of the hybrid virus includes a nucleic acid sequence which encodes a variant L protein and a nucleic acid sequence which encodes a variant HN protein. Such a hybrid virus would, like cp45, have at least two attenuating lesions. Moreover, the 3' leader region of the hybrid virus can be a variant 3' leader region which has at least one nucleic acid variation relative to the 3' leader region of the wild-type HPIV-3 target virus. The cp45 3' leader region is a preferred variant 3' leader region. Similarly, the genome of the hybrid virus can include a nucleic acid sequence which encodes variant NP, P(+C), M or F proteins having at least one amino acid variation relative to their respective wild-type proteins. The cp45 NP, P(+C), M and F proteins are preferred variant proteins.

An alternative, slightly less attenuated hybrid virus has a genome which includes a nucleic acid sequence which encodes a variant L protein and a nucleic acid sequence which encodes a wild-type HN protein. The 3' leader region of this hybrid virus can be a wild-type or variant 3' leader region and the viral genome can also include nucleic acid sequences which encode either wild-type or variant NP, P(+C) M and F proteins. An exemplary hybrid virus is a modified cp45 virus where the HN gene of cp45 has been replaced with the HN gene of wild-type HPIV-3 (JS). Specifically, such a modified cp45 hybrid virus would have a viral genome which includes, in succession from its 3' end, (i) a nucleic acid sequence which is the same as the nucleic acid sequence of the 3' leader region of cp45, (ii) a nucleic acid sequence which encodes the nucleocapsid protein [NP] of cp45, (iii) a nucleic acid sequence which encodes the phosphoprotein [P(+C)] of cp45, (iv) a nucleic acid sequence which encodes the matrix protein [M] of cp45, (v) a nucleic acid sequence which encodes the fusion protein [F] of cp45 or of the target virus, (vi) a nucleic acid sequence which encodes the hemagglutinin-neuraminidase protein [HN] of the target virus, and (vii) a nucleic acid sequence which encodes the L protein of cp45. A vaccine comprising a hybrid virus having a wild-type HN protein and a variant L protein would be slightly less attenuated than a vaccine comprising a virus which included both variant HN and variant L proteins. For example, a vaccine which includes the modified cp45 virus described above (having a wild-type (JS) HN protein and a cp45 L protein), is less attenuated than cp45 relative to the wild-type JS strain. These vaccines may be of commercial significance, for example, if clinical trials with cp45 show that a slightly higher level of replication and resulting higher immune response would be desirable.

Vaccines directed at viruses other than HPIV-3 can also be created. For example, the region of the genome of the target virus that encodes one or more surface glycoproteins or surface antigens of the target virus (typically proteins responsible for attachment, penetration and release of the virus and virus progeny) may be combined, through genetic engineering techniques, with the region of the cp45 viral genome which encodes proteins responsible for replication and internal structure. The resulting hybrid virus will have the temperature sensitive attenuation properties contributed by the cp45 genome and the virus-specific antigenic properties of the target virus. As such, the hybrid virus will have a predictable level of safety and immunogenicity and be suitable for use as a vaccine in humans.

A vaccine developed from cp45 in combination with a non-HPIV-3 target virus comprises an enveloped, negative-sense, single-stranded RNA hybrid virus and an appropriate pharmaceutical carrier. The hybrid virus includes a nucleic acid sequence which encodes at least one surface antigen of a target virus. The encoded surface antigens are antigenically different from the surface antigens of HPIV-3 viruses such as cp45. The hybrid viral genome also includes a nucleic acid sequence which encodes either or both of the following: (i) a variant large protein [L] having an RNA-polymerase activity which is less than the polymerase activity associated with the target virus at a temperature of about 39° C. and/or (ii) a portion of the cp45 HN protein having neuraminidase activity which is less than the neuraminidase activity of the target virus at a temperature of about 39° C. The encoded portion of the HN protein is preferably at least about 50 amino acid residues in length, more preferably at least about 100 amino acids residues in length, even more preferably at least about 200 amino acid residues in length and most preferably at least about 220 amino acid residues in length. The encoded portion preferably includes amino acid residue 384 of the HN protein of cp45, or a functionally similar variant residue within about 5 amino acid residues of residue 384 of cp45. The encoded portion most preferably includes an amino acid sequence which is the same as the amino acid sequence from residue 160 to residue 385 of cp45.

The possibility for reversion to a non-attenuated strain is lower if the genome of the hybrid virus more closely resembles the cp45 genome in the 3' leader region and in the regions encoding the NP, P[+C] and M proteins. Hence, a preferred hybrid virus suitable for use in vaccines against target viruses other than HPIV-3 strains has a chimeric genome which comprises, in succession from its 3' end: a nucleic acid sequence which is the same as the nucleic acid sequence of the 3' leader region of a cp45 viral genome; nucleic acid sequences which encode the nucleocapsid protein, [NP], the phosphoprotein, P[+C], and the matrix protein, [M], of cp45; a nucleic acid sequence which encodes at least one surface antigen of an enveloped target virus other than an HPIV-3 virus, and a nucleic acid sequence which encodes a variant L protein.

As referred to in the aforementioned hybrid viruses directed against HPIV-3 and non-HPIV-3 target viruses, a variant L protein is a HPIV-3 L protein which has at least one variation in amino acid sequence compared to its structurally most closely associated wild-type HPIV-3 L protein (that is, relative to the wild-type protein from which the variant protein was derived or relative to the wild-type protein encoded by the gene from which a mutated gene encoding the variant protein was derived). For purposes herein, a HPIV-3 L protein is a protein having an amino acid sequence which has at least about a 90% sequence identity with the amino acid sequence of the wild-type HPIV-3 (JS) L protein. The sequence identity between the variant L protein and the wild-type HPIV-3 (JS) L protein is, in order of increasing preference, more preferably at least about 95%, at least about 97%, at least about 98%, at least about 99%, at least about 99.5%, at least about 99.7% and at least about 99.8%. Since the JS strain L protein has 2,258 amino acids and since, in general, most HPIV-3 L proteins are comprised of over 2000 amino acid residues, a 99.8% sequence identity corresponds to about 4 variations in amino acid sequence between the wild-type and variant proteins. Likewise, the variant HPIV-3 L protein cannot be the same protein as the wild-type polymerase protein of the target virus (regardless of whether the target virus is an HPIV-3 virus or a non-HPIV-3 virus). Hence, the variant L protein has at least one variation in amino acid sequence relative to the L protein (or the functionally analogous polymerase protein) of the target virus. Moreover, the variant L protein has RNA-polymerase activity which is less than the polymerase activity normally associated with the target virus at a non-permissive temperature ranging from about 37° C. to about 40° C. and preferably at a temperature of about 39° C. The polymerase activity of the variant L protein is preferably at least about 10 times less than the polymerase activity of the target virus. The polymerase activity of the variant L protein is more preferably, in order of increasing preference, at least a factor of $10^2$, $10^3$, $10^4$, $10^5$ and $10^6$ less than the polymerase activity of the target virus.

The variant L protein is most preferably a mutant HPIV-3 (JS) L protein. That is, a preferred variant L protein has at least one variation in amino acid sequence relative to the L protein of HPIV-3 (JS). While the term variation is intended to include additions, deletions or substitutions in amino acid residues, the variation is preferably a substitution which is functionally analogous to the substitutions of the cp45 L protein relative to the wild-type HPIV-3 (JS) L protein. Hence, the variation in amino acid sequence relative to HPIV-3 (JS) is preferably within about (ie, plus or minus) five amino acid residues of residues 942, 992 or 1558 of SEQ ID NO. 1. More specifically, the variation in amino acid sequence relative to HPIV-3 (JS) preferably includes one or more of the following substitutions: His for Tyr at residue 942, Phe for Leu at residue 992 and Ile for Thr at residue 1558. The variant L protein more preferably has at least two variations in amino acid sequence relative to the wild-type HPIV-3 (JS) L protein: His for Tyr at residue 942 of SEQ ID NO. 1 and Phe for Leu at residue 992 of SEQ ID NO. 1. The variant L protein has, even more preferably, all three of the variations in amino acid sequence of the cp45 L protein, and may include other variations as well. While other substitutions or other variations may, in addition to those described immediately preceding, also exist in the amino acid sequence of the variant L protein, a variant HPIV-3 (JS) L protein having only these recited substitutions and conferring reduced polymerase activity are generally sufficient. The variant L protein is most preferably the L protein of cp45.

A variant hemagglutinin-neuraminidase (HN) protein is, as referred to in the aforementioned hybrid viruses, a HN protein having at least one variation in amino acid sequence relative to its structurally most closely related wild-type HPIV-3 HN protein. The variant HN protein has an amino acid sequence which has at least about a 90% sequence identity with the amino acid sequence of the wild-type HPIV-3 (JS) HN protein. The sequence identity between the variant HN protein and the wild-type HPIV-3 (JS) HN protein is, in order of increasing preference, more preferably at least about 95%, at least about 97%, at least about 98%, at least about 99% and at least about 99.5%. Since HPIV-3 HN proteins typically comprise at least about 400 amino acid residues, a 99.5% sequence identity corresponds to about 2 variations in amino acid sequence between the wild-type and variant proteins. Likewise, the variant HPIV-3 HN protein cannot be the same protein as the wild-type neuraminidase protein of the target virus; the variant HN protein has at least one variation in amino acid sequence relative to the neuraminidase protein (or the functionally analogous release protein) of the target virus. Moreover, the variant HN protein has neuraminidase activity which is less than the neuraminidase activity normally associated with the target virus at a non-permissive temperature ranging from about 37° C. to about 40° C. and preferably at a temperature of about 39° C. The neuraminidase activity of the variant HN protein is preferably less than the polymerase activity of the target virus by a factor of at least about 3, more preferably by a factor of at least about 5, even more preferably by a factor of at least about 10 and most preferably by a factor of at least about 15.

The variant HN protein is preferably a mutant HPIV-3 (JS) HN protein which has at least one variation in amino acid sequence relative to the HN protein of HPIV-3 (JS). While the variation can be an addition, deletion or substitution, the variation is preferably a substitution which is functionally analogous to the substitutions of the cp45 HN protein described in SEQ ID NO. 2 relative to the wild-type HPIV-3 HN protein. Hence, the substitution is preferably at or within (ie, plus or minus) about five amino acid residues of amino acid residue 384 of the JS strain HN protein. The variant HN protein more preferably includes the substitution of Ala for Val at position 384 or another functionally equivalent substitution within 5 residues thereof. Other variations may, in addition to those described immediately preceding, also exist in the amino acid sequence of the variant HN protein; however, a variant HPIV-3 (JS) HN protein having only the single amino acid substitution recited and conferring reduced neuraminidase activity is generally sufficient. The variant HN protein is most preferably the HN protein of cp45.

The genes described above as being included in the genome of a hybrid virus are, in practice, operatively linked for expression. The exact sequence in which the genes are linked is not narrowly critical. Moreover, the various viral genomes may further include non-coding nucleic acid residues between the various genes.

In addition to an attenuated hybrid virus, the vaccine of the present invention also comprises a pharmaceutically appropriate or acceptable carrier for the attenuated hybrid virus. Typical carriers include the tissue culture fluid in which the virus is grown, diluents such as phosphate-buffered saline and/or stabilizers such as gelatin.

The method for producing an attenuated hybrid virus suitable for use as a human vaccine against a target wild-type virus includes genetic engineering techniques applied to insert target gene sequences encoding target surface glycoproteins into the cp45 genome in place of the corresponding surface glycoprotein genes in the cp45 genome or replacement of naturally-occurring genes encoding neuraminidase proteins or polymerase proteins in target viruses with variant proteins having reduced activities. The method detailed below is an exemplary method. Those skilled in the art will appreciate that variations in this method and other methods are also suitable to produce a hybrid virus. The standard methods in molecular biology useful for these purposes can be found in a variety of well-known references, including for example Sambrook et al., *Molecular Cloning,* Cold Spring Harbor Laboratory Press, 2nd Ed. 1989. The methods can be used, in particular, to produce attenuated hybrid viruses for use in vaccines against HPIV-1, HPIV-2, RSV, influenza and measles target viruses.

To produce a cp45 hybrid virus in which cp45 is used as a backbone and combined with surface antigens from a target virus, the viral genome of cp45 is first converted into full-length cDNA clone. Typically, several different portions of the genome are amplified using PCR and ligated in successive steps into a full length cDNA clone. The regions of the target virus genome encoding the target's surface glycoproteins are also converted into a cDNA clone. Genomic regions of target viruses having negative-sense or positive-sense, single-stranded RNA genomes, such as HPIV-1, HPIV-2, RSV, measles and influenza viruses, are converted in the same manner as cp45. DNA from viruses having DNA genomes can be directly ligated into the DNA plasmid vector.

The cDNA clone of the cp45 genome is then incorporated into a plasmid vector. Plasmid vectors such as pBluescriptII (Stratagene) or other commercially available vectors which are suitable for subsequent transfection and expression in a mammalian host cell may be used. Briefly, the cDNA clone and plasmid vector are combined using restriction enzyme digestion and ligation reactions. The recombinant plasmid is then cloned and purified.

Genetic manipulations are conducted to replace the regions of the cp45 cDNA genome which encode the F and HN proteins with the cDNA or DNA copy of the target virus' genes which encode the target's one or more surface glycoproteins.

Negative-sense, single-stranded RNA hybrid viruses are then produced from the recombinant viral genome by transfecting the hybrid cDNA plasmid vector into cells such as mammalian cells for synthesis of progeny viral genomes, viral proteins and viral particles using reverse genetic techniques. (Palese 1995; Lawson et al. 1995; Schnell et al. 1994). Briefly, the plasmid vector containing the cDNA copies are transfected into a host cell which has been previously infected with a recombinant vaccinia virus expressing bacteriophage T7 RNA polymerase. Plasmid vectors that express HPIV-3 NP, P and L proteins, produced according to the method described in Example 4, are cotransfected into the host cell. The cDNA is transcribed to produce full-length, negative-sense (genomic) RNA. Expression of the NP, L and P proteins facilitates synthesis of progeny hybrid virus. The hybrid virions are then isolated, grown in appropriate mammalian cells and tested to verify temperature sensitive phenotype and associated attenuation.

Another practical application of the invention relating to the observation that attenuating lesions of cp45 correlate to defects in the L and HN genes of cp45 is a method for determining whether a HPIV-3 virus or a cp45-hybrid virus is attenuated. As used herein, the term "cp45-hybrid" virus refers to a chimeric virus having genes which encode a variant L protein and/or a variant HN protein, as such variant proteins are described above. Such a determination is made by confirming the presence of at least one variation in the region of the HPIV-3 genome which encodes the L protein relative to the corresponding region of the genome of wild-type HPIV-3. Alternatively, defects in the region encoding the HN protein, and particularly at or within about 5 residues of residue 384 can be indicative of decreased neuraminidase activity. A determination can, in the same manner, also be made as to whether a cp45-hybrid virus is attenuated. Verification of attenuation is necessary in a variety of situations. For example, verification is useful in research laboratories, as quality control checks in commercial production of vaccines, as verification by regulatory agencies, and as final checks on new vaccine lots before administration to a patient. Verification of attenuation is likewise useful to check the stability of a vaccine after it has been administered to a patient. Isolates from the patient may be checked to verify that the progeny virus have retained the temperature sensitive attenuated phenotype.

A variety of methods for confirming the presence of nucleotide variations are known in the art. For example, the nucleic acid region which encodes the L protein could be sequenced in its entirety and compared to the wild-type gene for L. Alternatively, where the viral strain being tested is cp45 or a cp45 hybrid virus, the L gene could be cut with restriction enzymes near the expected variations at residues 942, 992 and 1558, and the smaller fragments could be sequenced for comparison with the L gene of wild-type HPIV-3 or of cp45. A more preferred method would include isolating nucleic acid from the viral strain being tested in single-stranded form, hybridizing the viral nucleic acid to probes which flank the variations, amplifying the region between the probes using PCR and sequencing the amplified regions of the L gene for comparison to wild-type HPIV-3 or to cp45. Other alternatives for determining point variations in gene sequences, such as single nucleotide extension reactions (Kuppuswamy et al. 1991) are also known in the art.

Figure 2B:
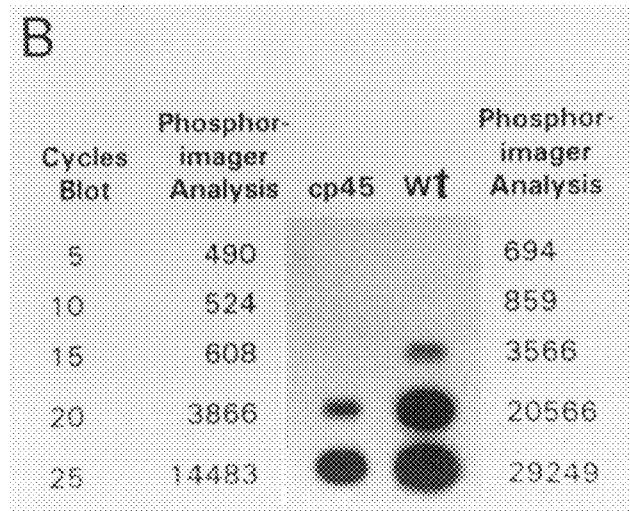

The complementation assay of the present invention, described in detail in Examples 3 and 4, may also be used to confirm the presence of at least one variation in the L gene. This method not only verifies gene sequence variation, but also simultaneously verifies the functional effect of such variations in the L gene. The dual nature of such a test is advantageous over sequencing information alone, due to the possibility of suppressor mutations. Briefly, a viral strain sample is obtained from a new vaccine lot or as a purified patient isolate. If necessary, the sample is amplified by growing in a cell culture medium. A standard, first plaque assay is performed, as a control, by incubating at a nonpermissive temperature (about 40° C.), and measuring replication. A complementation assay is then performed in which host cells are transfected with a plasmid vector that expresses wild-type HPIV-3 L protein and are also infected with the viral sample. (See Examples 3 and 4). Plasmid vectors which express wild-type NP and/or P proteins may be cotransfected into the host cells. A second plaque assay is performed on the complemented viral sample, and the results are compared to the results of the first plaque assay. A variation in the sample virus's L gene will be indicated by a significant increase, preferably at least a 10 fold increase, and most preferably a 100 fold increase, in replication of the complemented viral sample as compared to the non-complemented sample, as measured by plaque assays. In a similar manner, neuraminidase growth experiments and activity assays can be conducted in the absence of and presence of exogenous neuraminidase to verify the presence of a defect in the HN gene.

The following non-limiting examples illustrate the principles and advantages of the invention.

EXAMPLES

As used in the following examples, cp45 was derived from wild-type HPIV-3 (JS strain), an isolate originally cultured from a child with febrile respiratory disease. A cold-adapted mutant was selected after serial passage of the virus 45 times at 20° C. and isolated by plaque purification (Belshe and Hissom 1982). The cp45 virus was subsequently grown at 32° C. in continuous cell lines. In each of the experiments discussed below in which comparative assays were used, the amount of initial virus present in the assay was determined using hemagglutinin assay analysis. Briefly, L-132 cells infected with cp45 virus and grown at 32° C. for 72 h were removed from cell culture dishes using a cell scraper. Pelleted cells were washed with PBS, sonicated and used for analysis of hemagglutination. Serial two fold dilutions of the sonicated virus-infected cell homogenate were made in 100 ul PBS (without $Ca^{+2}$ and $Mg^{+2}$) in a 96 well V bottom microtiter plate. Then 100 ul of a 0.5% suspension of guinea pig erythrocytes in PBS (without $Ca^{+2}$ and $Mg^{+2}$) was added to each well, and the plate was incubated at 4° C. for ~2 h until a clear button or HA was observed with the negative and positive controls, respectively.

Example 1

Temperature-Dependent Replication, Protein Synthesis and mRNA Synthesis of cp45

Unlike the wild-type HPIV-3 strain, the cp45 strain loses its replication ability at non-permissive higher temperatures (above about 37° C.). This loss of replication activity contributes to the observed attenuation in the cp45 vaccine. Moreover, a related decrease in virus-specific mRNA synthesis and in protein synthesis exists in the cp45 strain relative to the wild-type strain.

cp45 virus was absorbed into a cellular culture medium at 32° C. for 1 hour and grown at 39.5° C. for 24 hours. Infected cells were then shifted to 32° C. for growth for an additional 24 hours. The virus titer in the culture supernatant was determined by plaque assay in L-132 cells. Infected cell monolayers were either stained with hematoxylin-eosin Y or overlaid with 0.9% agar and 0.005% neutral red for visualization of viral plaques. The results from at least three independent experiments showed consistent virus recovery (less than fivefold variation).

Comparison of cp45 and wild-type (JS) virus replication in L-132 cells at permissive (32° C.) and nonpermissive (39.5° C.) temperatures in a temperature-shift assay is shown in Table 1. Normal growth of both viruses was observed at the permissive temperature. However, poor replication (reduction of ~$10^6$-fold) of cp45 was observed when the virus was absorbed on L-132 cells at 39.5° C. and incubated at the same temperature. However, the virus showed some replication upon changing the incubation temperature from 39.5 to 32° C. after 24 h. On the other hand, the wild-type virus exhibited similar replication at 39.5 and 32° C. cp45 virus replicated upon temperature shift from 39.5 to 32° C., thereby demonstrating the characteristic temperature-sensitive phenotype and indicating an absence of revertant virus at 39.5 or 32° C.

The virus-specific RNA synthesis occurring in the cp45 strain is likewise significantly lower than such synthesis in the wild-type strain. Hence, only low levels of messenger RNA (mRNA) are produced at the non-permissive temperature. In order to determine the overall viral transcriptional activity at the nonpermissive temperature, mRNA synthesis from the P protein gene of cp45 virus was studied by reverse transcription-PCR for comparison with that of the wild-type virus.

Briefly, L-132 cells were infected with cp45 or wild-type virus at a similar multiplicity of infection. After virus adsorption at 32° C., cells were grown at 39.5° C. for 24 h. Infected cells were treated with actinomycin D (10 $\mu$g/ml) for 14 h, and RNA was prepared by acid guanidinium thiocyanate-phenol-chloroform extraction. Amplification of the P mRNA was conducted by reverse transcription-PCR from the same quantities of total RNA (10 $\mu$g) and virus-specific sense (CCAACAACAACTCCCAGATC, nucleotide positions 2740 to 2759) and anti-sense (TGCCTCCATAAGTGGGTCAA, nucleotide positions 3280 to 3299) synthetic oligonucleotide primers. The amplification reaction was performed by using an automatic thermocycler (Perkin-Elmer Cetus), with cycling parameters of denaturation at 94° C. for 1 min, primer annealing at 50° C. for 1.5 min, and primer extension at 72° C. for 2 min. As an internal standard, amplification of the actin mRNA was similarly carried out by reverse transcription-PCR by using the same RNA preparations and β-actin gene-specific sense (SEQ ID NO. 7 nucleotide positions 2563 to 2586) and anti-sense SEQ ID NO. 8, nucleotide positions 2977 to 3000) primers. A plasmid DNA containing the P protein gene of HPIV-3, kindly provided by Mark S. Galinski (The Cleveland Clinic Foundation, Cleveland, Ohio), was also used as a positive control in the PCR amplification. A PCR-amplified ~559 bp fragment from the P protein gene plasmid DNA was isolated by electrophoresis in a 0.8% agarose gel. The DNA band was excised, eluted by using an ultrafree MC column (Millipore Corporation, Bedford, Mass.), and radiolabeled with [$\alpha$-$^{32}$P]dCTP by the random primed oligonucleotide labeling method by using a commercially available kit (Boehringer Mannheim Biochemicals, Indianapolis, Ind.), for use as a probe. An actin probe was similarly prepared for use in Southern hybridization.

mRNA synthesis was tested by comparing the levels of message between the two RNA preparations in a parallel experiment. The reaction products from different cycles of PCR amplification were analyzed by agarose gel electrophoresis followed by ethidium bromide staining and showed a significant difference in the levels of message generated from cp45 and wild-type virus. On the other hand, similar message levels of the actin gene, studied as an internal control, were observed for the RNA isolated from cp45 and wild-type virus-infected cells. A similar observation was noted following Southern hybridization of the electrophoresed DNA. The typical amplification profile of the PCR products from viral mRNA is shown in FIG. 2A. A semi-quantitative approach was taken for the estimation of the differences between these messages by slot blot hybridization with fourfold dilutions of a single cDNA sample. A representative example of the results, shown in FIG. 2B, further indicates differences in the message of the P gene from cp45 and wild-type virus-infected cells at 15 and 20 cycles of PCR amplification. Message from the P protein gene of cp45 virus was estimated to be approximately 17% of that of wild-type virus by PhosphorImaging analysis.

Protein synthesis at the higher non-permissive temperature was also significantly lower in the cp45 strain as compared to the wild-type strain. cp45 virus polypeptide synthesis was analyzed by a pulse-chase experiment followed by immunoprecipitation with a hyperimmune rabbit antiserum to HPIV-3 or monoclonal antibodies to HN and NP.

Briefly, virus-infected cells were grown at 39.5 or 32° C. for 24 h and pulsed with $^{35}$S-protein label (Amersham Corporation, Arlington Heights, Ill.) for 1 h. Labeled cell lysates were immunoprecipitated after a chase of 0, 1, 2, 3, and 4 h with hyperimmune rabbit antiserum to HPIV-3 or with a pool of anti-HN and anti-NP monoclonal antibodies. Immunoprecipitates were analyzed by sodium dodecyl sulfate-polyacrylamide gel electrophoresis, followed by autoradiography.

Figure 3A:
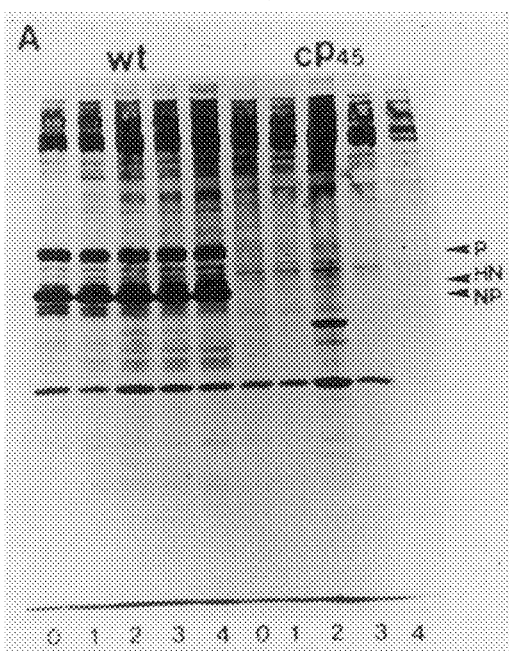
Figure 3B:
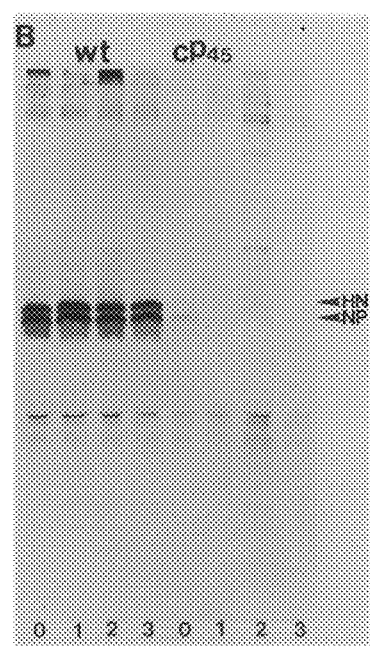
Figure 4A:
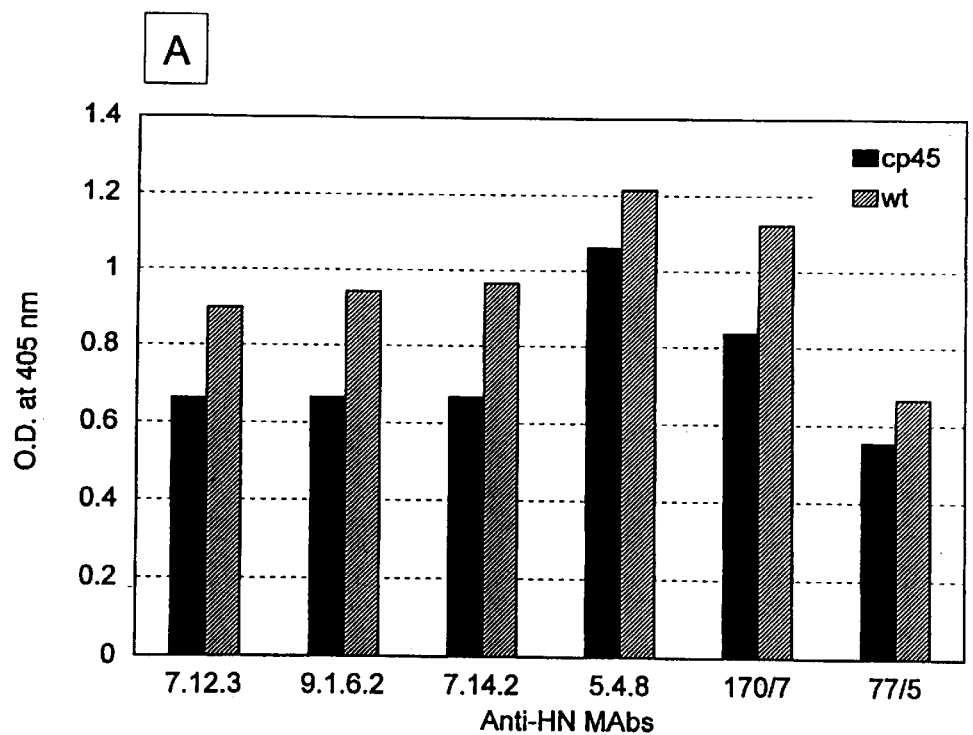
Figure 4B:
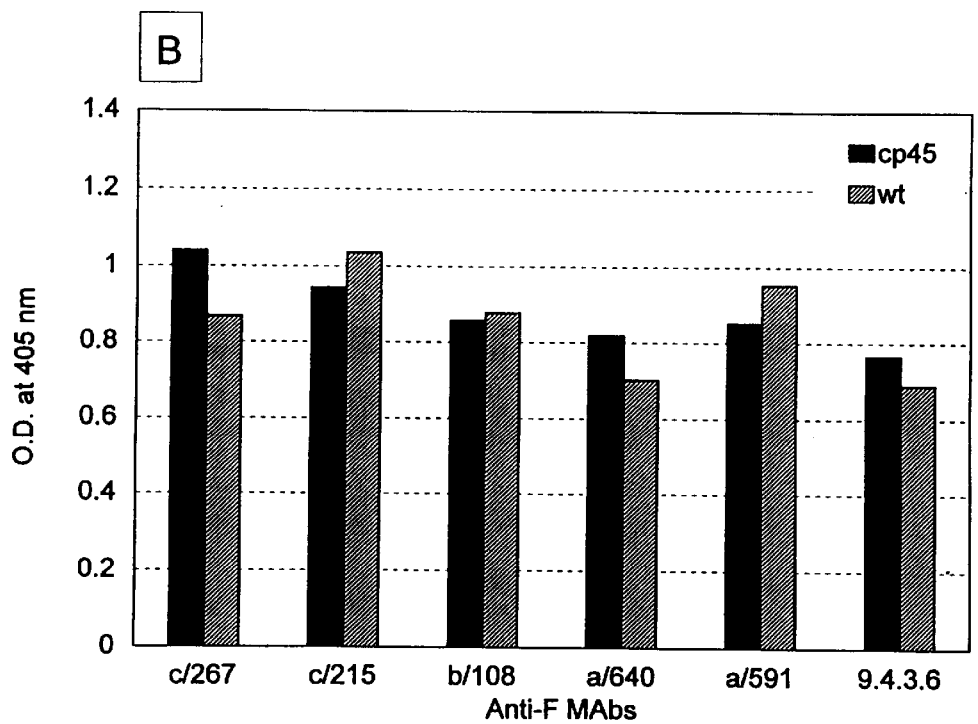
Figure 5A:
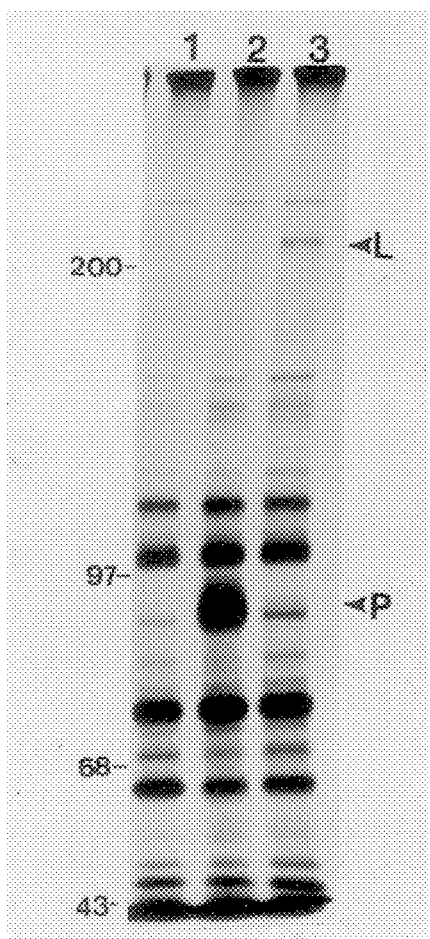
Figure 5B:
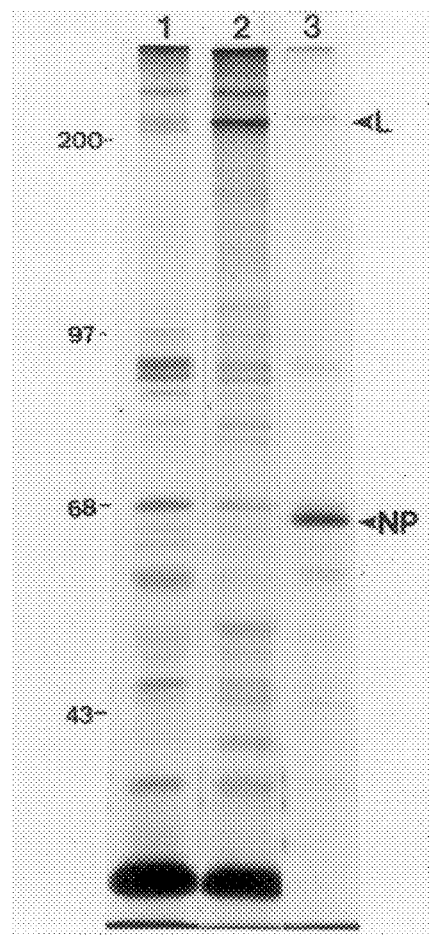
Figure 6A:
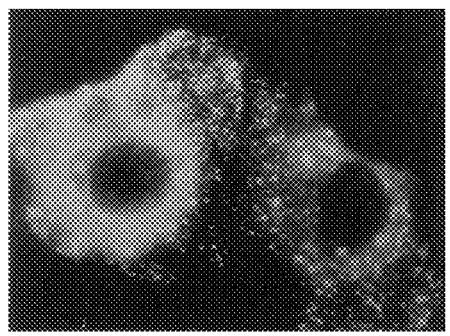
Figure 6B:
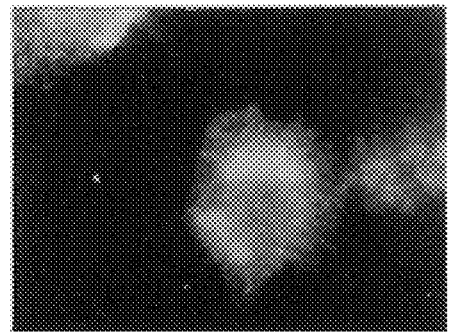
Figure 6C:
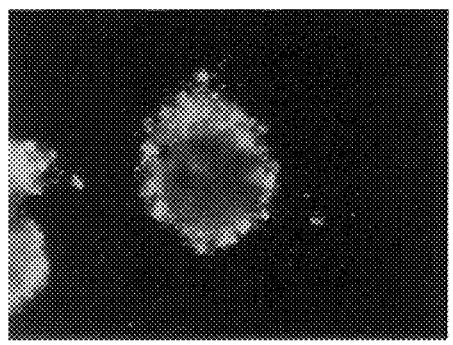
Figure 6D:
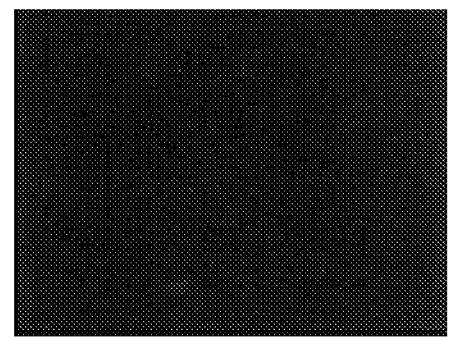

The results show a major difference in the synthesis of viral proteins between the wild-type and cp45 virus. Synthesis of wild-type virus polypeptides during the pulse period was not processed or modified further during the 4-h chase period (FIG. 3). On the other hand, cp45 virus polypeptide synthesis appeared to be extremely weak or almost undetectable. However, synthesis of cp45 and wild-type virus polypeptides was found to be similar when cells were grown at 32° C.

Example 2

Temperature-Dependent Neuraminidase Activity of cp45 cp45 virus was grown on L-132 cells at 32 or 39.5° C., and the virus-infected cell homogenate was analyzed for neuraminidase activity. The cp45 strain exhibited a reduced neuraminidase activity at the nonpermissive, higher temperature. Such a decrease in activity inhibits the release of progeny virus particles from an infected cell surface.

Briefly, 100 µl of 0.2 M sodium acetate buffer (pH 5.5) was mixed with an equal volume of infected cell homogenate with a known number of hemagglutinin activity units. Then, 0.1 ml of bovine fetuin (15 mg/ml, type IV; Sigma Chemical Company, St. Louis, Mo.) dissolved in the same buffer was added to the reaction mixture, and the mixture was incubated at 37° C. overnight. The amount of released neuraminic acid in the reaction mixture was determined. Wild-type parent virus was also included in this study for comparison.

When tested with two different molecular-size substrates, the neuraminidase property of the cp45 virus incubated at the nonpermissive temperature showed lower activity, by a factor ranging from about 4 to about 10, than cells infected with the wild-type virus (Table 3).

Example 3

Evaluation of Other Biological Properties of cp45

Antigenic relatedness of cp45 and the wild-type parent virus strain was initially compared by hemagglutination (HA) inhibition and neutralization assays using a monospecific rabbit antiserum to affinity-purified HPIV-3 HN glycoprotein. Rabbit anti-HN showed similar HA inhibition activities and neutralization titers (within twofold variation) with both the virus strains.

Subsequently, representative anti-HN and anti-F monoclonal antibodies recognizing distinct antigenic sites of the HN and F glycoprotein molecules were tested by enzyme-linked immunosorbent assay (ELISA). Dynatech polyvinyl plates (Immulon I) were coated with 1 μg of freeze-thaw disrupted virions per well. Monoclonal antibodies were tested at twofold serial dilutions for each virus strain (cp45 and the wild type), and the results were compared with the linear slopes of the reactivity pattern.

The results are presented (FIG. 4) as the mean optical densities from three independent experiments, showing variations within 0.05 to 0.08. The antibodies recognized the HN and F glycoproteins of cp45 virus and by ELISA showed titers similar to that of the wild-type virus. This suggests that the antigenic sites of cp45 virus were not altered as a result of its adaptation for growth at 20° C.

Moreover, the cp45 virus glycoproteins are processed and transported to the cell surface even at the nonpermissive temperature. Infected L-132 cells were tested 24 h after infection by immunofluorescence with specific monoclonal antibodies to HN and F. Confluent monolayers of L-132 cells were grown on coverslips, infected with the virus, and incubated at 32 or 39.5° C. At 24 h postinfection, cells were washed with phosphate-buffered saline and tested with monoclonal antibodies. At both incubation temperatures (32 and 39.5° C.), cp45-infected cells showed immunofluorescence on the cell surface.

HA and fusion activity was also investigated. cp45 virus grown at 32° C. was pelleted by ultracentrifugation and used for an HA assay to test the functional property of the HN glycoprotein. As the cp45 virus showed extremely poor growth at 39.5° C., we tested the HA activity of infected cell homogenates following incubation at the nonpermissive temperature. Results showed detectable HA activity of the cp45 virus grown at the permissive or nonpermissive temperature. cp45 virus-infected LLC-$MK_2$, Vero, and L-132 cells also showed formation of multinucleated giant cells or syncytium formation, a characteristic of virus fusion activity, when grown at 32° C. However, fusion activity was significantly reduced upon incubation of cp45 virus-infected cells at 39.5° C., probably because of poor replication of the virus at the nonpermissive temperature.

Example 4

Expression of HPIV-3 NP, P and L Wild-Type Proteins

Wild-type NP, P and L proteins of HPIV-3 (JS) strain were expressed for use in co-expression assays. The molecular cloning and sequence analysis of the HPIV-3 NP, P, and L genes have been previously described. (Galinski et al. 1988; Galinski et al. 1986; Galinski et al. 1986'). Briefly, all genes were removed from their recombinant vectors by restriction endonuclease digestion and ligated into the appropriate sites of pcDL-SR beta 8.2 vector DNA. This vector is derived from pcDL-SR alpha-296 and contains a polyvalent restriction site with flanking T7 and SP6 promoter sequences downstream from the SR alpha promoter. pcDL-SR beta 8.2 is a multifunctional vector, and gene expression can be driven by using a simian virus 40 (SV40) early promoter or alternatively by using a vaccinia virus expressing T7 RNA polymerase.

Plasmids containing nucleic acid regions which encode the NP, P and L proteins were incorporated into DNA vectors. Plasmid pSP18-NP, which contains the NP gene, was first digested with SphI, and the resulting cohesive end was repaired with T7 DNA polymerase. The gene was then released from the vector with BAMHI and ligated into pcDL-SR beta 8.2 which had been digested with EcoRI, subsequently repaired with Klenow fragment, and then further treated with BAMHI. Plasmid pSP19-P, which contains the P gene, was digested with BAMRI and PvuII to release the P gene. The gene was subsequently ligated into pcDL-SR beta 8.2 which had been digested with XbaI, subsequently repaired with Klenow fragment, and then further treated with BAMHI. Plasmid pGEM3-L, containing the L gene, was first digested with HindIII, and the resulting cohesive end was repaired with Klenow fragment. The L gene was then released from the vector with SacI and cloned into pcDL-SR beta 8.2 which has been digested with EcoRI, subsequently repaired with Klenow fragment, and then further treated with SacI.

All ligation reactions consisted of vector and gene fragments with compatible ends which would force ligation of the inserts in the desired orientation relative to the SR alpha and T7 promoters. Recombinant clones were randomly picked and further analyzed by restriction endonuclease digestion to confirm the orientation and efficacy of the subcloning. The gene termini were confirmed by dideoxy sequence analysis (U.S. Biochemical, Cleveland, Ohio) to ensure that the initiating methionine and termination codons were maintained.

To examine the biological properties of the various nucleocapsid-associated proteins, we initially tested for the protein expression of L (L-11), P (P-1), and NP (NP-1) in a transient expression system, using a recombinant vaccinia virus containing the bacteriophage T7 RNA polymerase gene (vTF7-3). HeLa-T4 cells, which are relatively resistant to the cytopathic effect of vaccinia virus, were infected with vTF7-3 and transfected with plasmids containing the HPIV-3 L, P, or NP gene, using Lipofectamine (Bethesda Research Laboratories, Gaithersburg, Md.).

Expression of the viral L, P and NP proteins was detected after 20h in [$^{35}$S]methionine-[$^{35}$S]cysteine-labeled transfected cell lysates by immunoprecipitation with a hyperimmune rabbit antiserum to HPIV-3 or a monoclonal antibody to NP (FIG. 5A). Immunoprecipitates were analyzed by sodium dodecyl sulfate (SDS)-polyacrylamide gel electrophoresis (PAGE) and autoradiography. To obtain better resolution of the large-molecular-size L protein, immunoprecipitates were also separated in a lower-percentage polyacrylamide gel (FIG. 5B). Immunoprecipitated L, P, and NP polypeptides from the corresponding DNA-transfected cells were indistinguishable in size from the authentic viral proteins. The amount of the L protein appeared to be lower than that of the P or NP protein immunoprecipitated by the antiserum from transfected cell lysates.

Example 5

Complementation of cp45 with Wild-Type Proteins

This example considers whether CV-1 cells which were transiently expressing the L, P or NP proteins could rescue (that is, increase the replication of the virus, as measured by plaque assay) cp45 at the nonpermissive temperature. Briefly, CV-1 cells were cotransfected with the plasmid vector pRSV-T (encoding the SV40 large T antigen driven by a Rous sarcoma virus long terminal repeat) and one or more recombinant plasmids containing the NP, P, or L gene and incubated at 37° C. Twenty hours posttransfection, the expressing cells were infected with cp45 or wild-type virus at a multiplicity of infection of 1, and infected cells were incubated for an additional 28 h at 39.5° C. Following incubation, cell culture medium was harvested and HPIV-3 titers were determined by plaque assay in L-132 cells at permissive (32° C.) and nonpermissive (39.5° C.) temperatures. Infected cell monolayers were stained with hematoxylin and eosin-Y or, alternatively, overlaid with 0.9% agar and 0.005% neutral red for visualization of viral plaques.

Although the vaccinia virus system provided excellent levels of expression, because of the concern regarding the use of a viral vector which causes extensive cytopathic effect in the cell monolayer and the difficulties inherent to measuring HPIV-3 replication in vaccinia virus coinfection experiments, we used an expression system which did not require the use of vaccinia virus to drive transcription of our plasmid vectors.

The vector pcDL-SR beta 8.2 contains a promoter, designated SR alpha, consisting of the SV40 early promoter and the R segment and part of the US sequence (R-U5') of the long terminal repeat of human T-cell leukemia virus type 1. The vector also contained the SV40 origin of replication and gives significant levels of protein expression in COS-1 or COS-7 cells, in which the plasmids are amplified by the endogenous levels of T antigen. The utility of this expression system was extended to CV-1 cells by coexpression in trans of the large T antigen from another plasmid vector, PRSV-T (35), kindly provided by James Pipas, University of Pittsburgh.

The transfected CV-1 cells were tested initially for intracellular expression of the viral proteins by immunofluorescence. Briefly, cells were fixed with acetone-methanol (1:1) for 10 min at −20° C. A hyperimmune rabbit antiserum to HPIV-3 (thoroughly preadsorbed with mock-transfected cells) was used as the primary antibody, and a fluorescein isothiocyanate tagged mouse anti-rabbit immunoglobulin G was used as the second antibody. Cells were examined at a magnification of ×600 on a Nikon microscope equipped for epifluorescence, and digital photographs were captured by using a computer imaging system (Oncor Image Systems, Inc.).

As shown in FIG. 6, L and P appeared to form small inclusions, whereas NP seemed to give a more homogeneous, punctate staining pattern. Negative control cells did not show any detectable immunofluorescence.

The results of a typical complementation experiment are shown in Table 2; similar results were achieved in assays performed in triplicate. Virus yield at 39.5° C. showed significant levels of cp45 replication at the nonpermissive temperature. These results indicate that the wild-type L protein was biologically functional and could complement the temperature sensitive mutation of the cp45 L protein, whereas expression of P and NP in the absence of L was nonfunctional. The virus titer represents a complementation efficiency of approximately 950 and 11,500 PFU of virus per 3×10° cells. Cells transfected with L, P, and NP show a 10-fold increase in cp45 virus yield compared with cells transfected with L alone or with L and P. This may be due to interactions among these proteins for the formation of the nucleocapsid complex for efficient virus replication. However, their specific interactions during virus replication remain to be determined. The results of this example further support the role of the L protein as an RNA-dependent RNA polymerase activity essential for transcription and the life cycle of HPIV-3. Other cell lines, not transfected with the L gene, failed to produce detectable virus titers.

Example 6

Ability of HPIV-1 L Protein to Complement cp45 and Retention of Temperature Sensitive Phenotype in cP45 Progeny cp45 virus produced from L-gene-transfected CV-1 cells at the nonpermissive temperature should remain temperature sensitive for growth despite their ability to replicate in L-expressing cells. At least 10 plaque-purified virus stocks of the rescued progeny virus were examined, and all virus stocks were found to have maintained their temperature sensitive property.

Further, L-protein complementation of cp45 is heterotypic exclusive. L-132 or primary rhesus monkey kidney cells, when coinfected with HPIV-1 and cp45, did not rescue growth of cp45 at the nonpermissive temperature.

Example 7

Plaque Assays for cp45 and HPIV-3 (JS) With or Without Exogenous Neuraminidase

Growth characteristics of cp45 and wild-type (JS) virus strains were determined without and with exogenous neuraminidase. The cp45 and, in separate experiments, the JS virus were adsorbed on L-132 cells at 32° C. for 1 h and grown in culture medium with or without the addition of bacterial neuraminidase isolated from *C. perfringens* for the indicated time frame. Virus titer in the culture supernatant was determined by plaque assay on L-132 cells as described previously. (Belshe and Hissom, 1982). Infected cell monolayers were stained with hematoxylin-eosin-Y or overlaid with 0.9% agar and 0.005% neutral red for the visualization of viral plaques. Each assay was repeated three times.

The results are shown in FIG. 7A for cp45 and in FIG. 7B for the JS strain, with the error bars indicating standard deviations of the three independent assays. FIG. 7A shows that cp45 virus titers taken after about 50 hours of incubation in a culture medium lacking exogenous neuraminidase were about five to fifteen times lower than a corresponding titer taken after incubation in a culture medium containing exogenous neuraminidase. FIG. 7B shows, in contrast, that wild-type JS virus titers were virtually identical after about 25 hours regardless of whether or not exogenous neuraminidase was present in the culture medium.

Example 8

Localized Fusion Activity of cp45 and Inhibition Thereof with Exogenous Neuraminidase L-132 cells were infected with cp45 at a low multiplicity of infection and grown with or without exogenous neuraminidase to evaluate the cytopathic effect of the virus. Analogous experiments using the HPIV-3 (JS) strain were conducted for comparison. Cells were infected at a multiplicity of infection (moi) of 0.1. A low multiplicity of virus infection was used so that only a small number of cells were infected early, thereby allowing for monitoring the nature of the cytopathic effect in the cell monolayer while the cells were incubated at 32° C. for 36 hours in a culture in which exogenous neuraminidase was absent. In separate experiments, infected cells were incubated in culture medium which included 50 ug (0.5 U) bacterial neuraminidase/ml.

The results are shown in FIGS. 8A through 8D. FIGS. 8A and 8B are photos of cells infected with cp45 and HPIV-3 (JS), respectively, after growth in culture without exogenous neuraminidase. cp45 infected cells exhibited significant localized fusion, as indicated by the presence of multinucleated giant cell or syncytia formation (FIG. 8A). Such localized fusion was not observed for JS-strain infected cells (FIG. 8B). FIGS. 8C and 8D are photos of cells infected with cp45 and HPIV-3 (JS), respectively, after growth in the presence of exogenous neuraminidase. The degree of localized cell fusion for cp45 infected cells was significantly reduced (FIG. 8C) and indicated a cytopathic effect similar to that observed for JS-strain infected cells (FIG. 8D).

Example 9

Immunofluorescence Staining Showing Restricted Distribution of Neuraminidase in cp45 Infected Cells The distribution of the variant HN protein in L-132 cells infected with cp45 at 33° C. was investigated using surface immunofluorescence techniques. Briefly, L-132 cells grown on cover slips were infected with cp45 or JS virus at multiplicity of infection of 0.01. After adsorption of the virus, cells were incubated with or without exogenous neuraminidase in the culture medium at 33° C. for 36 h. Infected cells were washed and reacted with a monoclonal antibody (13-9-6-2) to the HN glycoprotein of HPIV-3 for surface immunofluorescence.

The results are shown in FIGS. 9A through 9D. FIGS. 9A and 9B are photos of cells infected with cp45 and HPIV-3 (JS), respectively, after growth in culture without exogenous neuraminidase. The distribution of the variant HN protein was substantially localized (FIG. 9A) compared to distribution of the wild-type JS HN protein (FIG. 9B). FIGS. 9C and 9D are photos of cells infected with cp45 and HPIV-3 (JS), respectively, after growth in the presence of exogenous neuraminidase. Under these conditions, the distribution of variant HN protein cp45 infected cells (FIG. 9C) was similar to the distribution of wild-type HN protein in JS-strain infected cells (FIG. 9D).

Example 10

Neuraminidase Activity Assays: pH Optima and Kinetic Studies

L-132 cells infected with cp45 virus and grown at 32° C. for 72 h were removed from cell culture dishes using a cell scraper. Pelleted cells were washed with PBS, sonicated and used for analysis of neuraminidase activity. Neuraminidase activity was determined by mixing 50 ul of 0.5 M phosphate buffer of known pH with an equal volume of infected cell homogenate of known hemagglutination units. Different size substrates, Fetuin (type IV) (15 mg/ml), 3'-N-acetylneuramin-lactose (1 mg/ml) or 6'-N-acetyl-neuramin-lactose (1 mg/ml) (Sigma Chemical Company, St. Louis, Mo.) dissolved in water were added to the reaction mixture and incubated at 37° C. overnight. pH was controlled during incubation at various values during separate experiments. Released neuraminic acid in the reaction mixture was determined using spectrophotometric techniques. HPIV-3 (JS) infected cells were processed in a similar manner to the cp45 infected cells and analogous activity analyses were conducted for comparison.

In one set of experiments, the pH optima of cp45 neuraminidase activity was analyzed and compared to that of the parent JS strain. FIG. 10A shows the variation in neuraminidase activity of the cp45 virus with pH when tested using fetuin or neuraminlactose assays at the nonpermissive temperature (39.5° C.). For cp45, the optimal pH was about 5.5 when the neuraminlactose assay was used (FIG. 10A—closed circles), but was lower (about 4.9) when the fetuin assay was used (FIG. 10A—open circles). FIG. 10B shows the variation in neuraminidase activity of the HPIV-3 (JS) virus with pH in analogous experiments. For the JS-strain, the optimal pH using the neuraminidase assay was, like cp45, about 5.5 (FIG. 10B—closed circles). However, when the fetuin assay was used to determine the optimal pH for the JS strain (FIG. 10B—open circles), the optimal pH was higher (about 6.3). Referring to either FIG. 10A or 10B, a comparison of the absolute values of neuraminidase activity determined by the different assay substrates is not particularly instructive, as the absolute activity reported for each of the two substrates appears to have been influenced by the initial amount of virus present in the respective assays. The bars on FIGS. 10A and 10B indicate standard deviations from three separate experimental runs.

In another set of experiments, enzyme kinetic studies were done at the initial stage of incubation with the two different linkages of the low molecular weight neuraminlactose substrates: 2→3 and 2→6 linkages. The pH was maintained at 5.5—the enzymatic optimum for the neuraminlactose substrate for both cp45 and wild-type JS strains. FIG. 11A shows that both cp45 and JS strains have a similar preference for the 2→3 linkage. FIG. 11B shows that cp45 has a preference for the 2→6 linkage relative to the JS strains. Comparison of FIGS. 11A and 11B shows that cp45 has a greater preference for the 2→3 linkage than for the 2→6 linkage.

Example 11

Neuraminidase Inhibition Assays for Comparison of cp45 and HPIV-3 (JS) Antigenic Sites The antigenic relatedness of the neuraminidase active site of cp45 and the parent JS strain of the virus was compared using neuraminidase inhibitory antibodies. A monospecific rabbit antiserum to affinity purified HPIV-3 HN glycoprotein and three monoclonal antibodies to the HN glycoprotein, 2-14-1, 13-9-6-2 and 170/8, were used in the neuraminidase inhibition assay. These antibodies are known to recognize neuraminidase active sites of the prototype HPIV-3 (47885) strain. The antibodies were tested at two-fold serial dilutions for each virus strain and the results were compared with the linear slopes of the reactivity pattern. A Mab 3-8-1 exclusively inhibiting the HA of the virus was used as a negative control, but did not show an inhibitory role of the neuraminidase activity (data not shown). FIG. 12A shows that no significant difference in antigenic sites between cp45 and HPIV-3 (JS) was observed for any of the inhibiting antibodies or antisera between cp45 and JS strains when fetuin was used as the assay substrate. FIG. 12B shows that the neuraminidase activity of the cp45 strain was less inhibited than the activity of the JS strain by the monoclonal antibodies 12-9-6-2 and 170/8 when the relatively smaller neuraminlactose substrate was used as the assay substrate. However, the extent of inhibition of the two strains was similar for the monoclonal antibody 2-14-1 and for the monospecific rabbit antisera.

In light of the detailed description of the invention and the examples presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

BIBLIOGRAPHY

Anderson, et al. 1992. Intracellular processing of the human respiratory syncytial virus fusion glycoprotein: Amino acid substitutions affecting folding, transport and cleavage. J. Gen. Virol. 73(Pt. 5):1177–88.

Belshe and Hissom 1982. Cold adaptation of parainfluenza virus type induction of three phenotypic markers. J. Med. Virol. 10:235–242.

Belshe, et al. 1992. Evaluation of a live attenuated, cold-adapted parainfluenza virus type 3 vaccine in children. J. Clin. Microbiol. 30:2064–2070

Baybutt and Pringle 1987. Molecular cloning and sequencing of the F and 22K membrane protein genes of the RSS-2 strain of respiratory syncytial virus. J. Gen. Virol. 68 (Pt 11):2789–96.

Clements, et al. 1991. Evaluation of bovine, cold-adapted human, and wild-type human parainfluenza type 3 viruses in adult volunteers and in chimpanzees. J. Clin. Microbiol. 29:1175–1182.

Collins, et al. 1993. Rescue of a 7502-nucleotide (49.3% of full-length) synthetic analog of respiratory syncytial virus genomic RNA. Virol. 195(1):252–6.

Crookshanks-Newman and Belshe. 1986. Protection of weanling hamsters from experimental infection with wild-type parainfluenza virus type 3 (para 3) by cold-adapted mutants of para 3. J. Med. Virol. 18:131–137.

Galinski et al. 1986. Molecular cloning and sequence analysis of the human parainfluenza 3 virus RNA encoding the nucleocapsid protein. Virol. 149:139–151.

Galinski et al. 1986'. Molecular cloning and sequence analysis of the human parainfluenza 3 virus mRNA encoding the P and C proteins. Virol. 154:46–60.

Galinski et al. 1988. Molecular cloning and sequence analysis of the human parainfluenza 3 virus gene encoding the L protein. Virol. 165:499–510.

Hall et al. 1993. A cold-adapted mutant of parainfluenza virus type 3 is attenuated and protective in chimpanzees. J. Infect. Dis. 167:958–962.

Hu, et al. 1990. Molecular cloning and sequence analysis of the fusion glycoprotein gene of human parainfluenza virus type 2. Virol. 179(2):915–20.

Johnson and Collins 1988. The A and B subgroups of human respiratory syncytial virus: Comparison of intergenic and gene-overlap sequences. J. Gen. Virol. 69(Pt 11):2901–6.

Johnson and Collins 1988'. The fusion glycoproteins of human respiratory syncytial virus of subgroups A and B: Sequence conservation provides a structural basis for antigenic relatedness. J. Gen. Virol. 69(Pt 10):2623–8.

Karron et al. 1995. A Live Human Parainfluenza Type 3 Virus Vaccine is Attenuated and Immunogenic in Healthy Infants and Children. The Journal of Infectious Diseases 172:1445–1450.

Kawano, et al. 1990. Sequence determination of the hemagglutinin-neuraminidase (HN) gene of human parainfluenza type 2 virus and the construction of a phylogenetic tree for HN proteins of all the paramyxoviruses that are infectious to humans. Virol. 174(1):303–13.

Kawano, et al. 1990'. Sequence of the fusion protein gene of human parainfluenza type 2 virus and its 3' intergenic region: Lack of small hydrophobic (SH) gene. Virol. 178(1):289–92.

Kuppuswamy, et al. 1991. Single nucleotide primer extension to detect genetic diseases: Experimental application to hemophilia B (factor IX) and cystic fibrosis genes. Proc. Natl. Acad. Sci. USA. 88:1143–1147

Lawson et al. 1995. Recombinant vesicular stomatitis viruses from DNA. Proc. Natl. Acad. Sci. USA 92:4477–4481.

Lerch, et al. 1990. Nucleotide sequence analysis and expression from recombinant vectors demonstrates that the attachment protein G of bovine respiratory syncytial virus is distinct from that of human respiratory syncytial virus. J. Virol. 64(11):5559–69.

Lopez, et al. 1988. Nucleotide sequence of the fusion and phosphoprotein genes of human respiratory syncytial (RS) virus long strain: Evidence of subtype genetic heterogeneity. Virus Research. 10(2–3):249–61.

Martin-Gallardo, et al. 1991. Expression of the F glycoprotein gene from human respiratory syncytial virus in *Escherichia coli*: Mapping of a fusion inhibiting epitope. Virol. 184(1):428–32.

Martin-Gallardo, et al. 1993. Expression of the G glycoprotein gene of human respiratory syncytial virus in *Salmonella typhimurium*. J. Gen. Virol. 74(Pt.3):453–8.

Matsuoka, et al. 1990. Sequence of the hemagglutinin-neuraminidase gene of human parainfluenza virus type 1. Virus Research. 16(1):107–13.

Merson, et al. 1988. Molecular cloning and sequence determination of the fusion protein gene of human parainfluenza virus type 1. Virol. 167(1):97–105

Palese, P. 1995. Genetic engineering of infectious negative-strand RNA viruses. [Review]. Trends in Microbiology. 3(4):123–5.

Precious, et al. 1990. Sequence analysis of the HN gene of parainfluenza virus type 2. J. Gen. Virol. 71(Pt 5):1163–8.

Schnell et al. 1994. Infectious rabies viruses from clone cDNA. EMBO J. 13:4195–4203.

Spriggs and Collins 1986. Human parainfluenza virus type 3: messenger RNAs, polypeptide coding assignments, intergenic sequences, and genetic map. J. Virol. 59:646–654.

Spriggs and Collins 1986.' Sequence analysis of the P and C protein genes of human parainfluenza virus type 3: Patterns of amino acid sequence homology among paramyxovirus proteins. J. Gen. Virol. 67:2705–2719.

Stokes, et al. 1993. The complete nucleotide sequence of two-cold adapted, temperature-sensitive attenuated mutant vaccine viruses (cp12 and cp45) derived from the JS strain of human parainfluenza virus type 3 (PIV3). Virus Res. 30:43–52.

Storey, et al. 1984. Structural characterization of viron proteins and genomic RNA of human parainfluenza virus 3. J. Virol. 52:761–766.

Sullender, et al. 1990. The respiratory syncytial virus subgroup B attachment glycoprotein: Analysis of sequence, expression from a recombinant vector, and evaluation as an immunogen against homologous and heterologous subgroup virus challenge. Virol. 178(1):195–203.

Sullender, et al. 1991. Genetic diversity of the attachment protein of subgroup B respiratory syncytial viruses. J. Virol. 65(10):5425–34.

Walravens, et al. 1990. Sequence comparison between the fusion protein of human and bovine respiratory syncytial viruses. J. Gen. Virol. 71 (Pt 12):3009–14.

What is claimed is:

1. An enveloped, negative-sense, single-stranded RNA hybrid virus, the hybrid virus having a genome comprising, operatively linked for expression, (i) a nucleic acid sequence which encodes at least one surface antigen of an enveloped target virus of the family Paramyxoviridae, the surface antigen being different from surface antigens of cp45 and (ii) a nucleic acid sequence which encodes a variant HPIV-3 large protein, L, the variant L protein having at least one variation in amino acid sequence relative to the L protein of wild-type HPIV-3 (JS), the variation being a substitution selected from the group consisting of His for Tyr at residue 942 of SEQ ID NO. 1, Phe for Leu at residue 992 of SEQ ID NO. 1, and Ile for Thr at residue 1558 of SEQ ID NO. 1, the variant L protein having polymerase activity.

2. A live vaccine suitable for use against an enveloped target virus of the family Paramyxoviridae, the vaccine comprising the hybrid virus of claim 1 and a pharmaceutically appropriate carrier.

3. The hybrid virus of claim 1 wherein the variant L protein has an amino acid sequence having at least a 90% sequence identity with the amino acid sequence of the wild type HPIV-3 (JS) L protein, and the variant L protein has an RNA-polymerase activity which is at least about 10 times less than the polymerase activity normally associated with the target virus at a temperature of about 39° C.

4. The hybrid virus of claim 3 wherein the hybrid virus has a genome further comprising (i) a nucleic acid sequence which is the same as the nucleic acid sequence of the 3' leader region of cp45; (ii) a nucleic acid sequence which encodes the nucleocapsid protein, NP, of cp45; (iii) a nucleic acid sequence which encodes the phosphoprotein, P(+C), of cp45; (iv) a nucleic acid sequence which encodes the matrix protein, M, of cp45; and (v) wherein the variant large protein, L, has at least two substitutions in amino acid sequence relative to the wild-type HPIV-3 (JS) L protein, the substitutions being His for Thr at residue 942 of SEQ ID NO. 1 and Phe for Leu at residue 992 of SEQ ID NO. 1.

5. A live vaccine suitable for use against an enveloped target virus of the family Paramyxoviridae, the vaccine comprising the hybrid virus of claim 3 and a pharmaceutically appropriate carrier.

6. The vaccine of claim 5 wherein the amino acid sequence of the variant L protein has at least a 99% sequence identity with the amino acid sequence of the wild-type HPIV-3 (JS) L protein.

7. The vaccine of claim 5 wherein the amino acid sequence of the variant L protein has at least a 99.5% sequence identity with the amino acid sequence of the wild-type HPIV-3 (JS) L protein.

8. The vaccine of claim 5 wherein the variant L protein has an amino acid sequence having a substitution in one, two or three amino acids relative to the sequence of the L protein of wild-type HPIV-3 (JS), the substitution being selected from the group consisting of His for Tyr at residue 942 of SEQ ID NO. 1, Phe for Leu at residue 992 of SEQ ID NO. 1, and Ile for Thr at residue 1558 of SEQ ID NO. 1.

9. The vaccine of claim 5 wherein the variant L protein has an amino acid sequence having at least two substitutions in amino acid sequence relative to the wild-type HPIV-3 (JS) L protein, the substitutions being His for Tyr at residue 942 of SEQ ID NO. 1 and Phe for Leu at residue 992 of SEQ ID NO. 1.

10. The vaccine of claim 5 wherein the variant L protein is the cp45 L protein.

11. The vaccine of claim 5 wherein the target virus is selected from the group consisting of HPIV-1, HPIV-2, RSV, and Morbillivirus viruses.

12. The vaccine of claim 5 wherein the target virus is selected from the group consisting of HPIV-1, HPIV-2 and RSV.

13. The vaccine of claim 5 wherein the variant L protein is an RNA-dependent RNA polymerase having an activity which is at least about 10 times less than the activity of the wild-type HPIV-3 (JS) polymerase.

14. The vaccine of claim 5 wherein the genome of the virus further comprises: (i) a nucleic acid sequence which encodes the nucleocapsid protein, NP, of a HPIV-3 virus and (ii) a nucleic acid sequence which encodes the phosphoprotein, P(+C), of a HPIV-3 virus.

15. The vaccine of claim 5 wherein the genome of the virus further comprises: (i) a nucleic acid sequence which is the same as the nucleic acid sequence of the 3' leader region of a HPIV-3 virus; (ii) a nucleic acid sequence which encodes the nucleocapsid protein, NP, of a HPIV-3 virus; (iii) a nucleic acid sequence which encodes the phosphoprotein, P(+C), of a HPIV-3 virus; and (iv) a nucleic acid sequence which encodes the matrix protein, M, of a HPIV-3 virus.

16. The vaccine of claim 15 wherein the 3' leader region of the HPIV-3 genome is the 3' leader region of the cp45 genome.

17. The vaccine of claim 15 wherein the HPIV-3 phosphoprotein is the phosphoprotein of cp45.

18. The vaccine of claim 15 wherein the HPIV-3 matrix protein is the matrix protein of cp45.

19. The vaccine of claim 15 wherein the 3' leader region of the HPIV-3 genome is the 3' leader region of the cp45 genome and the HPIV-3 NP, P(+C), and M proteins are cp45 NP, P(+C) and M proteins.

20. The vaccine of claim 5 wherein the genome of the hybrid virus further comprises (i) a nucleic acid sequence which is the same as the nucleic acid sequence of the 3' leader region of cp45; (ii) a nucleic acid sequence which encodes the nucleocapsid protein, NP, of cp45; (iii) a nucleic acid sequence which encodes the phosphoprotein, P(+C), of cp45; (iv) a nucleic acid sequence which encodes the matrix protein, M, of cp45; (v) wherein the surface antigen encoding nucleic acid sequence encodes a surface antigen of a target virus selected from the group consisting of HPIV-1, HPIV-2 and RSV; and (vi) wherein the L protein encoding nucleic acid sequence encodes a variant large protein, L, having RNA-polymerase activity which is at least ten times less than the polymerase activity normally associated with the target virus at a temperature of about 39° C., having at least a 99.8% sequence identity with the amino acid sequence of the wild-type HPIV-3 (JS) L protein and having at least two substitutions in amino acid sequence relative to the wild-type HPIV-3 (JS) L protein, the substitutions being His for Tyr at residue 942 of SEQ ID NO. 1 and Phe for Leu at residue 992 of SEQ ID NO. 1.

21. The enveloped, negative-sense, single-stranded RNA hybrid virus of claim 1, wherein the genome comprises, operatively linked for expression, a nucleic acid sequence which is the same as the nucleic acid sequence of the 3' leader region of a wild-type HPIV-3 target virus or which encodes at least one protein selected from the group consisting of the matrix protein, M, of said target virus, and the fusion protein, F, of said target virus and the hemagglutinin-neuraminidase protein, HN, of the target virus.

22. A live vaccine suitable for use against a HPIV-3 target virus, the vaccine comprising the hybrid virus of claim 21 and a pharmaceutically appropriate carrier.

23. The vaccine of claim 22 wherein the amino acid sequence of the variant L protein has at least a 90% sequence identity with the amino acid sequence of the wild-type HPIV-3 (JS) L protein.

24. The vaccine of claim 22 wherein the amino acid sequence of the variant L protein has at least a 99% sequence identity with the amino acid sequence of the wild-type HPIV-3 (JS) L protein.

25. The vaccine of claim 22 wherein the amino acid sequence of the variant L protein has at least a 99.5% sequence identity with the amino acid sequence of the wild-type HPIV-3 (JS) L protein.

26. The vaccine of claim 22 wherein the amino acid sequence of the variant L protein has a substitution in one, two or three amino acids relative to the sequence of the L protein of wild-type HPIV-3 (JS), the substitution being selected from the group consisting of His for Tyr at residue 942 of SEQ ID NO. 1, Phe for Leu at residue 992 of SEQ ID NO. 1 and Ile for Thr at residue 1558 of SEQ ID NO. 1.

27. The vaccine of claim 22 wherein the amino acid sequence of the variant L protein has at least a 99% sequence identity with the amino acid sequence of the wild-type HPIV-3 (JS) L protein and has at least two substitutions in amino acid sequence relative to the wild-type HPIV-3 (JS) L protein, the substitutions being His for Tyr at residue 942 of SEQ ID NO. 1 and Phe for Leu at residue 992 of SEQ ID NO. 1.

28. The vaccine of claim 22 wherein the variant L protein is the L protein of the HPIV-3 strain designated as cp45.

29. The vaccine of claim 27 wherein the viral genome comprises a nucleic acid sequence which encodes a variant hemagglutinin-neuraminidase protein, HN, having an amino acid sequence which has at least a 90% sequence identity with the amino acid sequence of the HN protein of wild-type HPIV-3 (JS) virus, which has at least one variation in amino acid sequence relative to the HN protein of the target virus and which has at least one variation in amino acid sequence relative to the HN protein of the HPIV-3 (JS) virus, the variation relative to the HN protein of HPIV-3 (JS) being at residue 384 of SEQ ID NO. 3, the variant HN protein having neuraminidase activity which is less than the neuraminidase activity normally associated with the HN protein of the target virus.

30. The vaccine of claim 29 wherein the amino acid sequence of the variant HN protein has a 99% sequence identity with the amino acid sequence of the wild-type HPIV-3 (JS) HN protein.

31. The vaccine of claim 29 wherein the amino acid sequence of the variant HN protein has a 99.5% sequence identity with the amino acid sequence of the wild-type PIV-3 (JS) HN protein.

32. The vaccine of claim 29 wherein the variant HN protein has at least one substitution in amino acid sequence relative to the wild-type HPIV-3 (JS) HN protein, the substitution being Val for Ala at residue 384 of SEQ ID NO. 3.

33. The vaccine of claim 29 wherein the viral genome comprises a nucleic acid sequence which encodes the hemagglutinin-neuraminidase protein, HN, of the HPIV-3 strain designated as cp45.

34. The vaccine of claim 29 wherein the viral genome comprises a nucleic acid sequence which is the same as the nucleic acid sequence of the 3' leader region of the HPIV-3 strain designated as cp45 or which encodes a protein selected from the group consisting of the nucleocapsid protein, NP, of cp45, the phosphoprotein, P(+C), of cp45, the matrix protein, M, of cp45, and the fusion protein, F, of cp45.

35. The vaccine of claim 29 wherein the viral genome comprises a nucleic acid sequence which encodes the hemagglutinin-neuraminidase protein, HN, of the HPIV-3 target virus.

36. The vaccine of claim 29 wherein the viral genome comprises (i) a nucleic acid sequence which is the same as the nucleic acid sequence of the 3' leader region of cp45, (ii) a nucleic acid sequence which encodes the nucleocapsid protein, NP, of cp45, (iii) a nucleic acid sequence which encodes the phosphoprotein, P(+C), of cp45, (iv) a nucleic acid sequence which encodes the matrix protein, M, of cp45, (v) a nucleic acid sequence which encodes the fusion protein, F, of cp45, (vi) a nucleic acid sequence which encodes the hemagglutinin-neuraminidase protein, HN, of the wild-type HPIV-3 target virus, and (vii) a nucleic acid sequence which encodes the L protein of cp45.

37. The vaccine of claim 29 wherein the hemagglutinin-neuraminidase protein encoded by the viral genome is the hemagglutinin-neuraminidase protein, HN, of wild-type HPIV-3 (JS).

38. The vaccine of claim 29 wherein the viral genome comprises (i) a nucleic acid sequence which is the same as the nucleic acid sequence of the 3' leader region of the target virus, (ii) a nucleic acid sequence which encodes the nucleocapsid protein, NP, of the target virus, (iii) a nucleic acid sequence which encodes the phosphoprotein, P(+C), of the target virus, (iv) a nucleic acid sequence which encodes the matrix protein, M, of the target virus, (v) a nucleic acid sequence which encodes the fusion protein, F, of the target virus, (vi) a nucleic acid sequence which encodes the hemagglutinin-neuraminidase protein, HN, of the target virus, and (vii) a nucleic acid sequence which encodes the variant L protein.

39. A plasmid vector comprising a positive or negative sense genome which includes, operatively linked for expression, (i) a nucleic acid sequence which encodes the surface antigens of a target virus of the family Paramyxoviridae, the surface antigens being different from surface antigens of the HPIV-3 strain designated as cp45, and (ii) a nucleic acid sequence which encodes a variant large protein, L, having an amino acid sequence which has at least a 90% sequence identity with the amino acid sequence of the wild-type HPIV-3 (JS) L protein and which has at least one variation in amino acid sequence relative to the L protein of wild-type HPIV-3 (JS), the variation being a substitution selected from the group consisting of His for Tyr at residue 942 of SEQ ID NO. 1, Phe for Leu at residue 992 of SEQ ID NO. 1, and Ile for Thr at residue 1558 of SEQ ID NO. 1, the variant L protein having an RNA-polymerase activity which is less than the polymerase activity normally associated with the target virus at a temperature of about 39° C.

40. A host cell transfected with the plasmid vector set forth in claim 34, wherein said host cell is cultured or isolated.

41. A method for producing an enveloped, negative-sense, single-stranded RNA hybrid virus suitable for use as a live vaccine, the method comprising:

preparing the chimeric plasmid vector of claim 39, transfecting a host cell with the chimeric plasmid vector, cotransfecting the host cell with plasmid vectors that express wild-type HPIV-3 NP, P and L proteins;

incubating the transfected host cell to produce a hybrid virus; and isolating the hybrid virus in a pharmaceutically acceptable medium.

42. The method as set forth in claim 41 wherein the chimeric plasmid vector is prepared by preparing a cDNA clone of the genome of the HPIV-3 strain designated as cp45, the genome comprising a nucleic acid sequence which encodes the HN protein of cp45 and the L protein of cp45, incorporating the cDNA clone of the cp45 genome into a plasmid vector, preparing a cDNA clone of or obtaining DNA of the genome of a target virus, the genome comprising a nucleic acid sequence which encodes the surface antigens of the target virus, and replacing the region of the plasmid vector's genome which encodes the HN protein of cp45 with the nucleic acid sequence which encodes the surface antigens of the target virus.

43. The method as set forth in claim 41 wherein the amino acid sequence of the variant L protein has at least a 99% sequence identity with the amino acid sequence of the wild-type HPIV-3 (JS) L protein and has at least two substitutions in amino acid sequence relative to the wild-type HPIV-3 (JS) L protein, the substitutions being selected from the group consisting of His for Tyr at residue 942 of SEQ ID NO. 1 and Phe for Leu at residue 992 of SEQ ID NO. 1.

44. The method as set forth in claim 41 wherein the genome further includes (i) a nucleic acid sequence which is the same as the nucleic acid sequence of the 3' leader region of cp45, (ii) a nucleic acid sequence which encodes the nucleocapsid protein, NP, of cp45, (iii) a nucleic acid sequence which encodes the phosphoprotein, P(+C), of cp45, (iv) a nucleic acid sequence which encodes the matrix protein, M, of cp45.

45. An enveloped, negative-sense, single-stranded RNA hybrid virus, the hybrid virus having a genome comprising, operatively linked for expression, a nucleic acid sequence which encodes (i) at least one surface antigen of a target virus of the family Paramyxoviridae, said target virus being one which depends upon a protein exhibiting neuraminidase activity to complete its replication cycle, the surface antigen being different from surface antigens of the HPIV-3 strain designated as cp45; and (ii) one protein which exhibits neuraminidase activity, said protein comprising a portion of the cp45 HN protein, the encoded portion having a neuraminidase activity and including an amino acid sequence which is the same as the amino acid sequence from residue 160 to residue 385 of SEQ. ID. NO. 3.

46. A live vaccine suitable for use against a target virus of the family Paramyxoviridae, the vaccine comprising the hybrid virus of claim 45 and a pharmaceutically appropriate carrier.

47. The vaccine as set forth in claim 46 wherein the viral genome further comprises a nucleic acid sequence which encodes a variant large protein, L, having an amino acid sequence which has at least a 90% sequence identity with the amino acid sequence of the wild-type HPIV-3 (JS) L protein and which has at least one variation in amino acid sequence relative to the L protein of wild-type HPIV-3 (JS), the variation being a substitution being selected from the group consisting of His for Tyr at residue 942 of SEQ ID NO. 1, Phe for Leu at residue 992 of SEQ ID NO. 1 and Ile for Thr at residue 1558 of SEQ ID NO. 1, the variant L protein having an RNA-polymerase activity which is less than the polymerase activity normally associated with the target virus at a temperature of about 39° C.

48. The vaccine as set forth in claim 47 wherein the amino acid sequence of the variant L protein has at least a 99% sequence identity with the amino acid sequence of the wild-type HPIV-3 (JS) L protein.

49. The vaccine as set forth in claim 47 wherein the amino acid sequence of the variant L protein has at least a 99% sequence identity with the amino acid sequence of the wild-type HPIV-3 (JS) L protein and has at least two substitutions in amino acid sequence relative to the wild-type HPIV-3 (JS) L protein, the substitutions being His for Tyr at residue 942 of SEQ ID NO. 1 and Phe for Leu at residue 992 of SEQ ID NO. 1.

50. The vaccine as set forth in claim 46 wherein the viral genome further comprises a nucleic acid sequence which encodes the large protein, L, of cp45.

51. An enveloped, negative-sense, single-stranded RNA hybrid virus having a genome comprising, operatively linked for expression, (i) a nucleic acid sequence which is the same as the nucleic acid sequence of the 3' leader region of a wild-type HPIV-3 target virus or which encodes at least one protein selected from the group consisting of the matrix protein, M, of the target virus, the fusion protein, F, of the target virus and the large protein, L, of the target virus, and (ii) a nucleic acid sequence which encodes a variant hemagglutinin-neuraminidase protein, HN, having an amino acid sequence which has at least a 90% sequence identity with the amino acid sequence of the HN protein of wild-type HPIV-3 (JS) virus, which has at least one variation in amino acid sequence relative to the HN protein of the target virus and which has at least one variation in amino acid sequence relative to the HN protein of the HPIV-3 (JS) virus, the variation relative to the HN protein of HPIV-3 (JS) being at residue 384 of SEQ ID NO. 3, the variant HN protein having neuraminidase activity which is less than the neuraminidase activity normally associated with the HN protein of the target virus.

52. A live vaccine suitable for use against a HPIV-3 target virus, the vaccine comprising the hybrid virus of claim 51 and a pharmaceutically appropriate carrier.

53. The vaccine of claim 52 wherein the amino acid sequence of the variant HN protein has a 99% sequence identity with the amino acid sequence of the wild-type HPIV-3 (JS) HN protein.

54. The vaccine of claim 52 wherein the amino acid sequence of the variant HN protein has a 99.5% sequence identity with the amino acid sequence of the wild-type HPIV-3 (JS) HN protein.

55. The vaccine of claim 52 wherein the variant HN protein has at least one substitution in amino acid sequence relative to the wild-type HPIV-3 (JS) HN protein, the substitution being Val for Ala at residue 384 of SEQ ID NO. 3.

56. The vaccine of claim 52 wherein the variant HN protein is the HN protein of the HPIV-3 strain designated as cp45.

57. The vaccine of claim 52 wherein the selection from group (i) is not the large protein, L, of the target virus, and wherein the viral genome further comprises a nucleic acid sequence which encodes a variant large protein, L, having an amino acid sequence which has at least a 90% sequence identity with the amino acid sequence of the wild-type HPIV-3 (JS) L protein and which has at least one substitution in amino acid sequence relative to the wild-type HPIV-3 (JS) L protein, the substitution being selected from the group consisting of His for Tyr at residue 942 of SEQ ID NO. 1, Phe for Leu at residue 992 of SEQ ID NO. 1 and Ile for Thr at residue 1558 of SEQ ID NO. 1, the variant L protein having an RNA-polymerase activity which is less than the RNA-polymerase activity normally associated with the L protein of the target virus at a temperature of about 39° C.

58. The vaccine of claim 52 wherein the viral genome comprises a nucleic acid sequence which encodes a variant large protein, L, having an amino acid sequence which has at least a 90% sequence identity with the amino acid sequence of the wild-type HPIV-3 (JS) L protein and which has at least two substitutions in amino acid sequence relative to the wild-type HPIV-3 (JS) L protein, the substitutions being His for Tyr at residue 942 of SEQ ID NO. 1 and Phe for Ile at residue 992 of SEQ ID NO. 1, the variant L protein having an RNA-polymerase activity which is less than the RNA-polymerase activity normally associated with the L protein of the target virus at a temperature of about 39° C.

59. The vaccine of claim 52 wherein the viral genome comprises a nucleic acid sequence which encodes the large protein, L, of cp45.

60. The vaccine of claim 52 wherein the viral genome comprises a nucleic acid sequence which is the same as the nucleic acid sequence of the 3' leader region of cp45 or which encodes a protein selected from the group consisting of the nucleocapsid protein, NP, of cp45, the phosphoprotein, P(+C), of cp45, the matrix protein, M, of cp45, and the fusion protein, F, of cp45.

61. A method for determining whether a HPIV-3 virus or a cp45-hybrid virus is attenuated, the method comprising confirming the presence of at least one variation in the genome of the virus relative to the genome of wild-type HPIV-3, the variation being selected from the group consisting of those which would cause a variation in the amino acid corresponding to position 942, 992, or 1558 of SEQ ID NO. 1 or position 384 of SEQ ID NO. 3.

62. The method of claim 61 wherein the presence of at least one variation in the gene encoding the L protein of the virus is confirmed by performing a complementation assay, wherein the virus is complemented in a host cell with L protein of the wild-type HPIV-3 virus.

63. A method for determining whether a HPIV-3 or a cp45-hybrid virus has a temperature sensitive phenotype, the method comprising obtaining a sample of a HPIV-3 virus or a cp45-hybrid virus, performing a first plaque assay at a non-permissive temperature on the virus as a control assay;

transfecting a mammalian host cell with a plasmid vector that expresses L protein of wild-type HPIV-3 (JS);

infecting the host cell with the virus;

incubating to yield a complemented virus;

performing a second plaque assay at a non-permissive temperature on the complemented viral sample; and comparing the second plaque assay to the control assay to confirm the presence of the temperature sensitive phenotype.

64. The method of claim 63 further comprising cotransfecting the host cell with a plasmid vector that expresses P protein of wild-type HPIV-3 (JS).

65. The method of claim 63 further comprising cotransfecting the host cell with a plasmid vector that expresses NP protein of wild-type HPIV-3 (JS).

66. A non-human host cell transfected with the plasmid vector set forth in claim 39, wherein said host cell is contained within an organism.

* * * * *

SEQUENCE LISTING

```
<160> NUMBER OF SEQ ID NOS: 8

<210> SEQ ID NO 1
<211> LENGTH: 2233
<212> TYPE: PRT
<213> ORGANISM: Human parainfluenza virus 3

<400> SEQUENCE: 1

Met Asp Thr Glu Ser Asn Asn Gly Thr Val Ser Asp Ile Leu Tyr Pro
  1               5                  10                  15

Glu Cys His Leu Asn Ser Pro Ile Val Lys Gly Lys Ile Ala Gln Leu
             20                  25                  30

His Thr Ile Met Ser Leu Pro Gln Pro Tyr Asp Met Asp Asp Asp Ser
         35                  40                  45

Ile Leu Val Ile Thr Arg Gln Lys Ile Lys Leu Asn Lys Leu Asp Lys
     50                  55                  60

Arg Gln Arg Ser Ile Arg Arg Leu Lys Leu Ile Leu Thr Glu Lys Val
 65                  70                  75                  80

Asn Asp Leu Gly Lys Tyr Thr Phe Ile Arg Tyr Pro Glu Met Ser Lys
                 85                  90                  95

Glu Met Phe Lys Leu Tyr Ile Pro Gly Ile Asn Ser Lys Val Thr Glu
            100                 105                 110

Leu Leu Leu Lys Ala Asp Arg Thr Tyr Ser Gln Met Thr Asp Gly Leu
        115                 120                 125
```

-continued

```
Arg Asp Leu Trp Ile Asn Val Leu Ser Lys Leu Ala Ser Lys Asn Asp
    130                 135                 140

Gly Ser Asn Tyr Asp Leu Asn Glu Glu Ile Asn Asn Ile Ser Lys Val
145                 150                 155                 160

His Thr Thr Tyr Lys Ser Asp Lys Trp Tyr Asn Pro Phe Lys Thr Trp
                165                 170                 175

Phe Thr Ile Lys Tyr Asp Met Arg Arg Leu Gln Lys Ala Arg Asn Glu
            180                 185                 190

Ile Thr Phe Asn Val Gly Lys Asp Tyr Asn Leu Leu Glu Asp Gln Lys
        195                 200                 205

Asn Phe Leu Leu Ile His Pro Glu Leu Val Leu Ile Leu Asp Lys Gln
    210                 215                 220

Asn Tyr Asn Gly Tyr Leu Ile Thr Pro Glu Leu Val Leu Met Tyr Cys
225                 230                 235                 240

Asp Val Val Glu Gly Arg Trp Asn Ile Ser Ala Cys Ala Lys Leu Asp
                245                 250                 255

Pro Lys Leu Gln Ser Met Tyr Gln Lys Gly Asn Asn Leu Trp Glu Val
            260                 265                 270

Ile Asp Lys Leu Phe Pro Ile Met Gly Glu Lys Thr Phe Asp Val Ile
        275                 280                 285

Ser Leu Leu Glu Pro Leu Ala Leu Ser Leu Ile Gln Thr His Asp Pro
    290                 295                 300

Val Lys Gln Leu Arg Gly Ala Phe Leu Asn His Val Leu Ser Glu Met
305                 310                 315                 320

Glu Leu Ile Phe Glu Ser Arg Glu Ser Ile Lys Glu Phe Leu Ser Val
                325                 330                 335

Asp Tyr Ile Asp Lys Ile Leu Asp Ile Phe Asn Lys Ser Thr Ile Asp
            340                 345                 350

Glu Ile Ala Glu Ile Phe Ser Phe Phe Arg Thr Phe Gly His Pro Pro
        355                 360                 365

Leu Glu Ala Ser Ile Ala Ala Glu Lys Val Arg Lys Tyr Met Tyr Ile
    370                 375                 380

Gly Lys Gln Leu Lys Phe Asp Thr Ile Asn Lys Cys His Ala Ile Phe
385                 390                 395                 400

Cys Thr Ile Ile Ile Asn Gly Tyr Arg Glu Arg His Gly Gly Gln Trp
                405                 410                 415

Pro Pro Val Thr Leu Pro Asp His Ala His Glu Phe Ile Ile Asn Ala
            420                 425                 430

Tyr Gly Ser Asn Ser Ala Ile Ser Tyr Glu Asn Ala Val Asp Tyr Tyr
        435                 440                 445

Gln Ser Phe Ile Gly Ile Lys Phe Asn Lys Phe Ile Glu Pro Gln Leu
    450                 455                 460

Asp Glu Asp Leu Thr Ile Tyr Met Lys Asp Lys Ala Leu Ser Pro Lys
465                 470                 475                 480

Lys Ser Asn Trp Asp Thr Val Tyr Pro Ala Ser Asn Leu Leu Tyr Arg
                485                 490                 495

Thr Asn Ala Ser Asn Glu Ser Arg Arg Leu Val Glu Val Phe Ile Ala
            500                 505                 510

Asp Ser Lys Phe Asp Pro His Gln Ile Leu Asp Tyr Val Glu Ser Gly
        515                 520                 525

Asp Trp Leu Asp Asp Pro Glu Phe Asn Ile Ser Tyr Ser Leu Lys Glu
    530                 535                 540
```

-continued

```
Lys Glu Ile Lys Gln Glu Gly Arg Leu Phe Ala Lys Met Thr Tyr Lys
545                 550                 555                 560

Met Arg Ala Thr Gln Val Leu Ser Glu Thr Leu Leu Ala Asn Asn Ile
                565                 570                 575

Gly Lys Phe Phe Gln Glu Asn Gly Met Val Lys Gly Glu Ile Glu Leu
            580                 585                 590

Leu Lys Arg Leu Thr Thr Ile Ser Ile Ser Gly Val Pro Arg Tyr Asn
        595                 600                 605

Glu Val Tyr Asn Asn Ser Lys Ser His Thr Asp Asp Leu Lys Thr Tyr
    610                 615                 620

Asn Lys Ile Ser Asn Leu Asn Leu Ser Ser Asn Gln Lys Ser Lys Lys
625                 630                 635                 640

Phe Glu Phe Lys Ser Thr Asp Ile Tyr Asn Asp Gly Tyr Glu Thr Val
                645                 650                 655

Ser Cys Phe Leu Thr Thr Asp Leu Lys Lys Tyr Cys Leu Asn Trp Arg
            660                 665                 670

Tyr Glu Ser Thr Ala Leu Phe Gly Glu Thr Cys Asn Gln Ile Phe Gly
        675                 680                 685

Leu Asn Lys Leu Phe Asn Trp Leu His Pro Arg Leu Glu Gly Ser Thr
    690                 695                 700

Ile Tyr Val Gly Asp Pro Tyr Cys Pro Pro Ser Asp Lys Glu His Ile
705                 710                 715                 720

Ser Leu Glu Asp His Pro Asp Ser Gly Phe Tyr Val His Asn Pro Arg
                725                 730                 735

Gly Gly Ile Glu Gly Phe Cys Gln Lys Leu Trp Thr Leu Ile Ser Ile
            740                 745                 750

Ser Ala Ile His Leu Ala Ala Val Arg Ile Gly Val Arg Val Thr Ala
        755                 760                 765

Met Val Gln Gly Asp Asn Gln Ala Ile Ala Val Thr Thr Arg Val Pro
    770                 775                 780

Asn Asn Tyr Asp Tyr Arg Val Lys Lys Glu Ile Val Tyr Lys Asp Val
785                 790                 795                 800

Val Arg Phe Phe Asp Ser Leu Arg Glu Val Met Asp Asp Leu Gly His
                805                 810                 815

Glu Leu Lys Leu Asn Glu Thr Ile Ile Ser Ser Lys Met Phe Ile Tyr
            820                 825                 830

Ser Lys Arg Ile Tyr Tyr Asp Gly Arg Ile Leu Pro Gln Ala Leu Lys
        835                 840                 845

Ala Leu Ser Arg Cys Val Phe Trp Ser Glu Thr Val Ile Asp Glu Thr
    850                 855                 860

Arg Ser Ala Ser Ser Asn Leu Ala Thr Ser Phe Ala Lys Ala Ile Glu
865                 870                 875                 880

Asn Gly Tyr Ser Pro Val Leu Gly Tyr Ala Cys Ser Ile Phe Lys Asn
                885                 890                 895

Ile Gln Gln Leu Tyr Ile Ala Leu Gly Met Asn Ile Asn Pro Thr Ile
            900                 905                 910

Thr Gln Asn Ile Arg Asp Gln Tyr Phe Arg Asn Pro Asn Trp Met Gln
        915                 920                 925

Tyr Ala Ser Leu Ile Pro Ala Ser Val Gly Gly Phe Asn Tyr Met Ala
    930                 935                 940

Met Ser Arg Cys Phe Val Arg Asn Ile Gly Asp Pro Ser Val Ala Ala
945                 950                 955                 960

Leu Ala Asp Ile Lys Arg Phe Ile Lys Ala Asn Leu Leu Asp Arg Ser
```

-continued

```
                965                 970                 975
Val Leu Tyr Arg Ile Met Asn Gln Glu Pro Gly Glu Ser Ser Phe Leu
            980                 985                 990

Asp Trp Ala Ser Asp Pro Tyr Ser Cys Asn Leu Pro Gln Ser Gln Asn
        995                1000                1005

Ile Thr Thr Met Ile Lys Asn Ile Thr Ala Arg Asn Val Leu Gln Asp
   1010                1015                1020

Ser Pro Asn Pro Leu Leu Ser Gly Leu Phe Thr Asn Thr Met Ile Glu
1025                1030                1035                1040

Glu Asp Glu Glu Leu Ala Glu Phe Leu Met Asp Arg Lys Val Ile Leu
            1045                1050                1055

Pro Arg Val Ala His Asp Ile Leu Asp Asn Ser Leu Thr Gly Ile Arg
        1060                1065                1070

Asn Ala Ile Ala Gly Met Leu Asp Thr Thr Lys Ser Leu Ile Arg Val
   1075                1080                1085

Gly Ile Asn Arg Gly Gly Leu Thr Tyr Ser Leu Leu Arg Lys Ile Ser
   1090                1095                1100

Asn Tyr Asp Leu Val Gln Tyr Glu Thr Leu Ser Arg Thr Leu Arg Leu
1105                1110                1115                1120

Ile Val Ser Asp Lys Ile Lys Tyr Glu Asp Met Cys Ser Val Asp Leu
            1125                1130                1135

Ala Ile Ala Leu Arg Gln Lys Met Trp Ile His Leu Ser Gly Gly Arg
        1140                1145                1150

Met Ile Ser Gly Leu Glu Thr Pro Asp Pro Leu Glu Leu Leu Ser Gly
        1155                1160                1165

Val Val Ile Thr Gly Ser Glu His Cys Lys Ile Cys Tyr Ser Ser Asp
    1170                1175                1180

Gly Thr Asn Pro Tyr Thr Trp Met Tyr Leu Pro Gly Asn Ile Lys Ile
1185                1190                1195                1200

Gly Ser Ala Glu Thr Gly Ile Ser Ser Leu Arg Val Pro Tyr Phe Gly
            1205                1210                1215

Ser Val Thr Asp Glu Arg Ser Glu Ala Gln Leu Gly Tyr Ile Lys Asn
            1220                1225                1230

Leu Ser Lys Pro Ala Lys Ala Ala Ile Arg Ile Ala Met Ile Tyr Thr
   1235                1240                1245

Trp Ala Phe Gly Asn Asp Glu Ile Ser Trp Met Glu Ala Ser Gln Ile
   1250                1255                1260

Ala Gln Thr Arg Ala Asn Phe Thr Leu Asp Ser Leu Lys Ile Leu Thr
1265                1270                1275                1280

Pro Val Ala Thr Ser Thr Asn Leu Ser His Arg Leu Lys Asp Thr Ala
            1285                1290                1295

Thr Gln Met Lys Phe Ser Ser Thr Ser Leu Ile Arg Val Ser Arg Phe
        1300                1305                1310

Ile Thr Met Ser Asn Asp Asn Met Ser Ile Lys Glu Ala Asn Glu Thr
   1315                1320                1325

Lys Asp Thr Asn Leu Ile Tyr Gln Gln Ile Met Leu Thr Gly Leu Ser
   1330                1335                1340

Val Phe Glu Tyr Leu Phe Arg Leu Lys Glu Thr Thr Gly His Asn Pro
1345                1350                1355                1360

Ile Val Met His Leu His Ile Glu Asp Glu Cys Cys Ile Lys Glu Ser
            1365                1370                1375

Phe Asn Asp Glu His Ile Asn Pro Glu Ser Thr Leu Glu Leu Ile Arg
        1380                1385                1390
```

```
Tyr Pro Glu Ser Asn Glu Phe Ile Tyr Asp Lys Asp Pro Leu Lys Asp
        1395                1400                1405

Val Asp Leu Ser Lys Leu Met Val Ile Lys Asp His Ser Tyr Thr Ile
        1410                1415                1420

Asp Met Asn Tyr Trp Asp Asp Thr Asp Ile Ile His Ala Ile Ser Ile
1425                1430                1435                1440

Cys Thr Ala Ile Thr Ile Ala Asp Thr Met Ser Gln Leu Asp Arg Asp
            1445                1450                1455

Asn Leu Lys Glu Ile Ile Val Ile Ala Asn Asp Asp Ile Asn Ser
            1460                1465                1470

Leu Ile Thr Glu Phe Leu Thr Leu Asp Ile Leu Val Phe Leu Lys Thr
        1475                1480                1485

Phe Gly Gly Leu Leu Val Asn Gln Phe Ala Tyr Thr Leu Tyr Ser Leu
        1490                1495                1500

Lys Ile Glu Gly Arg Asp Leu Ile Trp Asp Tyr Ile Met Arg Thr Leu
1505                1510                1515                1520

Arg Asp Thr Ser His Ser Ile Leu Lys Val Leu Ser Asn Ala Leu Ser
            1525                1530                1535

His Pro Lys Val Phe Lys Arg Phe Trp Asp Cys Gly Val Leu Asn Pro
        1540                1545                1550

Ile Tyr Gly Pro Asn Thr Ala Ser Gln Asp Gln Ile Lys Leu Ala Leu
        1555                1560                1565

Ser Ile Cys Glu Tyr Ser Leu Asp Leu Phe Met Arg Glu Trp Leu Asn
        1570                1575                1580

Gly Val Ser Leu Glu Ile Tyr Ile Cys Asp Ser Asp Met Glu Val Ala
1585                1590                1595                1600

Asn Asp Arg Lys Gln Ala Phe Ile Ser Arg His Leu Ser Phe Val Cys
            1605                1610                1615

Cys Leu Ala Glu Ile Ala Ser Phe Gly Pro Asn Leu Leu Asn Leu Thr
            1620                1625                1630

Tyr Leu Glu Arg Leu Asp Leu Leu Lys Gln Tyr Leu Glu Leu Asn Ile
            1635                1640                1645

Lys Glu Asp Pro Thr Leu Lys Tyr Val Gln Ile Ser Gly Leu Leu Ile
        1650                1655                1660

Lys Ser Phe Pro Ser Thr Val Thr Tyr Val Arg Lys Thr Ala Ile Lys
1665                1670                1675                1680

Tyr Leu Arg Ile Arg Gly Ile Ser Pro Pro Glu Val Ile Asp Asp Trp
            1685                1690                1695

Asp Pro Val Glu Asp Glu Asn Met Leu Asp Asn Ile Val Lys Thr Ile
            1700                1705                1710

Asn Asp Asn Cys Asn Lys Asp Asn Lys Gly Asn Lys Ile Asn Asn Phe
            1715                1720                1725

Trp Gly Leu Ala Leu Lys Asn Tyr Gln Val Leu Lys Ile Arg Ser Ile
        1730                1735                1740

Thr Ser Asp Ser Asp Asp Asn Asp Arg Leu Asp Ala Asn Thr Ser Gly
1745                1750                1755                1760

Leu Thr Leu Pro Gln Gly Gly Asn Tyr Leu Ser His Gln Leu Arg Leu
            1765                1770                1775

Phe Gly Ile Asn Ser Thr Ser Cys Leu Lys Ala Leu Glu Leu Ser Gln
            1780                1785                1790

Ile Leu Met Lys Glu Val Asn Lys Asp Lys Asp Arg Leu Phe Leu Gly
            1795                1800                1805
```

-continued

```
Glu Gly Ala Gly Ala Met Leu Ala Cys Tyr Asp Ala Thr Leu Gly Pro
        1810                1815                1820

Ala Val Asn Tyr Tyr Asn Ser Gly Leu Asn Ile Thr Asp Val Ile Gly
1825                1830                1835                1840

Gln Arg Glu Leu Lys Ile Phe Pro Ser Glu Val Ser Leu Val Gly Lys
            1845                1850                1855

Lys Leu Gly Asn Val Thr Gln Ile Leu Asn Arg Val Lys Val Leu Phe
        1860                1865                1870

Asn Gly Asn Pro Asn Ser Thr Trp Ile Gly Asn Met Glu Cys Glu Ser
        1875                1880                1885

Leu Ile Trp Ser Glu Leu Asn Asp Lys Ser Ile Gly Leu Val His Cys
        1890                1895                1900

Asp Met Glu Gly Ala Ile Gly Lys Ser Glu Glu Thr Val Leu His Glu
1905                1910                1915                1920

His Tyr Ser Val Ile Arg Ile Thr Tyr Leu Ile Gly Asp Asp Asp Val
            1925                1930                1935

Val Leu Val Ser Lys Ile Ile Pro Thr Ile Thr Pro Asn Trp Ser Arg
        1940                1945                1950

Ile Leu Tyr Leu Tyr Lys Leu Tyr Trp Lys Asp Val Ser Ile Ile Ser
        1955                1960                1965

Leu Lys Thr Ser Asn Pro Ala Ser Thr Glu Leu Tyr Leu Ile Ser Lys
        1970                1975                1980

Asp Ala Tyr Cys Thr Ile Met Glu Pro Ser Glu Ile Val Leu Ser Lys
1985                1990                1995                2000

Leu Lys Arg Leu Ser Leu Leu Glu Glu Asn Asn Leu Leu Lys Trp Ile
            2005                2010                2015

Ile Leu Ser Lys Lys Arg Asn Asn Glu Trp Leu His His Glu Ile Lys
            2020                2025                2030

Glu Gly Glu Arg Asp Tyr Gly Ile Met Arg Pro Tyr His Met Ala Leu
        2035                2040                2045

Gln Ile Phe Gly Phe Gln Ile Asn Leu Asn His Leu Ala Lys Glu Phe
        2050                2055                2060

Leu Ser Thr Pro Asp Leu Thr Asn Ile Asn Asn Ile Ile Gln Ser Phe
2065                2070                2075                2080

Gln Arg Thr Ile Lys Asp Val Leu Phe Glu Trp Ile Asn Ile Thr His
            2085                2090                2095

Asp Asp Lys Arg His Lys Leu Gly Gly Arg Tyr Asn Ile Phe Pro Leu
            2100                2105                2110

Lys Asn Lys Gly Lys Leu Arg Leu Leu Ser Arg Arg Leu Val Leu Ser
        2115                2120                2125

Trp Ile Ser Leu Ser Leu Ser Thr Arg Leu Leu Thr Gly Arg Phe Pro
        2130                2135                2140

Asp Glu Lys Phe Glu His Arg Ala Gln Thr Gly Tyr Val Ser Leu Ala
2145                2150                2155                2160

Asp Thr Asp Leu Glu Ser Leu Lys Leu Leu Ser Lys Asn Ile Ile Lys
            2165                2170                2175

Asn Tyr Arg Glu Cys Ile Gly Ser Ile Ser Tyr Trp Phe Leu Thr Lys
            2180                2185                2190

Glu Val Lys Ile Leu Met Lys Leu Ile Gly Gly Ala Lys Leu Leu Gly
            2195                2200                2205

Ile Pro Arg Gln Tyr Lys Glu Pro Glu Asp Gln Leu Leu Glu Asn Tyr
        2210                2215                2220

Asn Gln His Asp Glu Phe Asp Ile Asp
```

-continued

```
2225                2230

<220> FEATURE:
<221> NAME/KEY: CDS
<222> LOCATION: (1)..(6702)

<210> SEQ ID NO 2
<211> LENGTH: 6702
<212> TYPE: DNA
<213> ORGANISM: Human parainfluenza virus 3

<400> SEQUENCE: 2 atg gac act gaa tct aac aat ggc act gta tct gac ata ctc tat cct        48
   Met Asp Thr Glu Ser Asn Asn Gly Thr Val Ser Asp Ile Leu Tyr Pro
    1               5                  10                  15 gag tgt cac ctt aac tct cct atc gtt aaa ggt aaa ata gca caa tta        96
   Glu Cys His Leu Asn Ser Pro Ile Val Lys Gly Lys Ile Ala Gln Leu
                20                  25                  30 cac act att atg agt cta cct cag cct tat gat atg gat gac gac tca       144
   His Thr Ile Met Ser Leu Pro Gln Pro Tyr Asp Met Asp Asp Asp Ser
            35                  40                  45 ata cta gtt atc act aga cag aaa ata aaa ctt aat aaa ttg gat aaa       192
   Ile Leu Val Ile Thr Arg Gln Lys Ile Lys Leu Asn Lys Leu Asp Lys
        50                  55                  60 aga caa cga tct att aga aga tta aaa tta ata tta act gaa aaa gtg       240
   Arg Gln Arg Ser Ile Arg Arg Leu Lys Leu Ile Leu Thr Glu Lys Val
   65                  70                  75                  80 aat gac tta gga aaa tac aca ttt atc aga tat cca gaa atg tca aaa       288
   Asn Asp Leu Gly Lys Tyr Thr Phe Ile Arg Tyr Pro Glu Met Ser Lys
                    85                  90                  95 gaa atg ttc aaa tta tat ata cct ggt att aac agt aaa gtg act gaa       336
   Glu Met Phe Lys Leu Tyr Ile Pro Gly Ile Asn Ser Lys Val Thr Glu
                100                 105                 110 tta tta ctt aaa gca gat aga aca tat agt caa atg act gat gga tta       384
   Leu Leu Leu Lys Ala Asp Arg Thr Tyr Ser Gln Met Thr Asp Gly Leu
            115                 120                 125 aga gat cta tgg att aat gtg cta tca aaa tta gcc tca aaa aat gat       432
   Arg Asp Leu Trp Ile Asn Val Leu Ser Lys Leu Ala Ser Lys Asn Asp
        130                 135                 140 gga agc aat tat gat ctt aat gaa gaa att aat aat ata tcg aaa gtt       480
   Gly Ser Asn Tyr Asp Leu Asn Glu Glu Ile Asn Asn Ile Ser Lys Val
   145                 150                 155                 160 cac aca acc tat aaa tca gat aaa tgg tat aat cca ttc aaa aca tgg       528
   His Thr Thr Tyr Lys Ser Asp Lys Trp Tyr Asn Pro Phe Lys Thr Trp
                    165                 170                 175 ttt act atc aag tat gat atg aga aga tta caa aaa gct cga aat gag       576
   Phe Thr Ile Lys Tyr Asp Met Arg Arg Leu Gln Lys Ala Arg Asn Glu
                180                 185                 190 atc act ttt aat gtt ggg aag gat tat aac ttg tta gaa gac cag aag       624
   Ile Thr Phe Asn Val Gly Lys Asp Tyr Asn Leu Leu Glu Asp Gln Lys
            195                 200                 205 aat ttc tta ttg ata cat cca gaa ttg gtt ttg ata tta gat aaa caa       672
   Asn Phe Leu Leu Ile His Pro Glu Leu Val Leu Ile Leu Asp Lys Gln
        210                 215                 220 aac tat aat ggt tat cta att act cct gaa tta gta ttg atg tat tgt       720
   Asn Tyr Asn Gly Tyr Leu Ile Thr Pro Glu Leu Val Leu Met Tyr Cys
   225                 230                 235                 240 gac gta gtc gaa ggc cga tgg aat ata agt gca tgt gct aag tta gat       768
   Asp Val Val Glu Gly Arg Trp Asn Ile Ser Ala Cys Ala Lys Leu Asp
                    245                 250                 255 cca aaa tta caa tct atg tat cag aaa ggt aat aac ctg tgg gaa gtg       816
```

```
              Pro Lys Leu Gln Ser Met Tyr Gln Lys Gly Asn Asn Leu Trp Glu Val
                          260                 265                 270 ata gat aaa ttg ttt cca att atg gga gaa aag aca ttt gat gtg ata              864
Ile Asp Lys Leu Phe Pro Ile Met Gly Glu Lys Thr Phe Asp Val Ile
            275                 280                 285 tcg tta tta gaa cca ctt gca tta tcc tta att caa act cat gat cct              912
Ser Leu Leu Glu Pro Leu Ala Leu Ser Leu Ile Gln Thr His Asp Pro
290                 295                 300 gtt aaa caa cta aga gga gct ttt tta aat cat gtg tta tcc gag atg              960
Val Lys Gln Leu Arg Gly Ala Phe Leu Asn His Val Leu Ser Glu Met
305                 310                 315                 320 gaa tta ata ttt gaa tct aga gaa tcg att aag gaa ttt ctg agt gta             1008
Glu Leu Ile Phe Glu Ser Arg Glu Ser Ile Lys Glu Phe Leu Ser Val
                325                 330                 335 gat tac att gat aaa att tta gat ata ttt aat aag tct aca ata gat             1056
Asp Tyr Ile Asp Lys Ile Leu Asp Ile Phe Asn Lys Ser Thr Ile Asp
            340                 345                 350 gaa ata gca gag att ttc tct ttt ttt aga aca ttt ggg cat cct cca             1104
Glu Ile Ala Glu Ile Phe Ser Phe Phe Arg Thr Phe Gly His Pro Pro
355                 360                 365 tta gaa gct agt att gca gca gaa aag gtt aga aaa tat atg tat att             1152
Leu Glu Ala Ser Ile Ala Ala Glu Lys Val Arg Lys Tyr Met Tyr Ile
370                 375                 380 gga aaa caa tta aaa ttt gac act att aat aaa tgt cat gct atc ttc             1200
Gly Lys Gln Leu Lys Phe Asp Thr Ile Asn Lys Cys His Ala Ile Phe
385                 390                 395                 400 tgt aca ata ata att aac gga tat aga gag agg cat ggt gga cag tgg             1248
Cys Thr Ile Ile Ile Asn Gly Tyr Arg Glu Arg His Gly Gly Gln Trp
                405                 410                 415 cct cct gtg aca tta cct gat cat gca cac gaa ttc atc ata aat gct             1296
Pro Pro Val Thr Leu Pro Asp His Ala His Glu Phe Ile Ile Asn Ala
            420                 425                 430 tac ggt tca aac tct gcg ata tca tat gaa aat gct gtt gat tat tac             1344
Tyr Gly Ser Asn Ser Ala Ile Ser Tyr Glu Asn Ala Val Asp Tyr Tyr
435                 440                 445 cag agc ttt ata gga ata aaa ttc aat aaa ttc ata gag cct cag tta             1392
Gln Ser Phe Ile Gly Ile Lys Phe Asn Lys Phe Ile Glu Pro Gln Leu
450                 455                 460 gat gag gat ttg aca att tat atg aaa gat aaa gca tta tct cca aaa             1440
Asp Glu Asp Leu Thr Ile Tyr Met Lys Asp Lys Ala Leu Ser Pro Lys
465                 470                 475                 480 aaa tca aat tgg gac aca gtt tat cct gca tct aat tta ctg tac cgt             1488
Lys Ser Asn Trp Asp Thr Val Tyr Pro Ala Ser Asn Leu Leu Tyr Arg
                485                 490                 495 act aac gca tcc aac gaa tca cga aga tta gtt gaa gta ttt ata gca             1536
Thr Asn Ala Ser Asn Glu Ser Arg Arg Leu Val Glu Val Phe Ile Ala
            500                 505                 510 gat agt aaa ttt gat cct cat cag ata ttg gat tat gta gaa tct ggg             1584
Asp Ser Lys Phe Asp Pro His Gln Ile Leu Asp Tyr Val Glu Ser Gly
515                 520                 525 gac tgg tta gat gat cca gaa ttt aat att tct tat agt ctt aaa gaa             1632
Asp Trp Leu Asp Asp Pro Glu Phe Asn Ile Ser Tyr Ser Leu Lys Glu
530                 535                 540 aaa gag atc aaa cag gaa ggt aga ctc ttt gca aaa atg aca tac aaa             1680
Lys Glu Ile Lys Gln Glu Gly Arg Leu Phe Ala Lys Met Thr Tyr Lys
545                 550                 555                 560 atg aga gct aca caa gtt tta tca gag aca cta ctt gca aat aac ata             1728
Met Arg Ala Thr Gln Val Leu Ser Glu Thr Leu Leu Ala Asn Asn Ile
                565                 570                 575
```

```
gga aaa ttc ttt caa gaa aat ggg atg gtg aag gga gag att gaa tta    1776
Gly Lys Phe Phe Gln Glu Asn Gly Met Val Lys Gly Glu Ile Glu Leu
            580                 585                 590 ctt aag aga tta aca acc ata tca ata tca gga gtt cca cgg tat aat    1824
Leu Lys Arg Leu Thr Thr Ile Ser Ile Ser Gly Val Pro Arg Tyr Asn
595                 600                 605 gaa gtg tac aat aat tct aaa agc cat aca gat gac ctt aaa acc tac    1872
Glu Val Tyr Asn Asn Ser Lys Ser His Thr Asp Asp Leu Lys Thr Tyr
    610                 615                 620 aat aaa ata agt aat ctt aat ttg tct tct aat cag aaa tca aag aaa    1920
Asn Lys Ile Ser Asn Leu Asn Leu Ser Ser Asn Gln Lys Ser Lys Lys
625                 630                 635                 640 ttt gaa ttc aag tca acg gat atc tac aat gat gga tac gag act gtg    1968
Phe Glu Phe Lys Ser Thr Asp Ile Tyr Asn Asp Gly Tyr Glu Thr Val
                645                 650                 655 agc tgt ttc cta aca aca gat ctc aaa aaa tac tgt ctt aat tgg aga    2016
Ser Cys Phe Leu Thr Thr Asp Leu Lys Lys Tyr Cys Leu Asn Trp Arg
            660                 665                 670 tat gaa tca aca gct cta ttt gga gaa act tgc aac caa ata ttt gga    2064
Tyr Glu Ser Thr Ala Leu Phe Gly Glu Thr Cys Asn Gln Ile Phe Gly
        675                 680                 685 tta aat aaa ttg ttt aat tgg tta cac cct cgt ctt gaa gga agt aca    2112
Leu Asn Lys Leu Phe Asn Trp Leu His Pro Arg Leu Glu Gly Ser Thr
690                 695                 700 atc tat gta ggt gat cct tac tgt cct cca tca gat aaa gaa cat ata    2160
Ile Tyr Val Gly Asp Pro Tyr Cys Pro Pro Ser Asp Lys Glu His Ile
705                 710                 715                 720 tca tta gag gat cac cct gat tct ggt ttt tac gtt cat aac cca aga    2208
Ser Leu Glu Asp His Pro Asp Ser Gly Phe Tyr Val His Asn Pro Arg
                725                 730                 735 ggg ggt ata gaa gga ttt tgt caa aaa tta tgg aca ctc ata tct ata    2256
Gly Gly Ile Glu Gly Phe Cys Gln Lys Leu Trp Thr Leu Ile Ser Ile
            740                 745                 750 agt gca ata cat cta gca gct gtt aga ata ggc gtg agg gtg act gca    2304
Ser Ala Ile His Leu Ala Ala Val Arg Ile Gly Val Arg Val Thr Ala
        755                 760                 765 atg gtt caa gga gac aat caa gct ata gct gta acc aca aga gta ccc    2352
Met Val Gln Gly Asp Asn Gln Ala Ile Ala Val Thr Thr Arg Val Pro
770                 775                 780 aac aat tat gac tac aga gtt aag aag gag ata gtt tat aaa gat gta    2400
Asn Asn Tyr Asp Tyr Arg Val Lys Lys Glu Ile Val Tyr Lys Asp Val
785                 790                 795                 800 gtg aga ttt ttt gat tca tta aga gaa gtg atg gat gat cta ggt cat    2448
Val Arg Phe Phe Asp Ser Leu Arg Glu Val Met Asp Asp Leu Gly His
                805                 810                 815 gaa ctt aaa tta aat gaa acg att ata agt agc aag atg ttc ata tat    2496
Glu Leu Lys Leu Asn Glu Thr Ile Ile Ser Ser Lys Met Phe Ile Tyr
            820                 825                 830 agc aaa aga atc tat tat gat ggg aga att ctt cct caa gct cta aaa    2544
Ser Lys Arg Ile Tyr Tyr Asp Gly Arg Ile Leu Pro Gln Ala Leu Lys
        835                 840                 845 gca tta tct aga tgt gtc ttc tgg tca gag aca gta ata gac gaa aca    2592
Ala Leu Ser Arg Cys Val Phe Trp Ser Glu Thr Val Ile Asp Glu Thr
850                 855                 860 aga tca gca tct tca aat ttg gca aca tca ttt gca aaa gca att gag    2640
Arg Ser Ala Ser Ser Asn Leu Ala Thr Ser Phe Ala Lys Ala Ile Glu
865                 870                 875                 880 aat ggt tat tca cct gtt cta gga tat gca tgc tca att ttt aag aac    2688
Asn Gly Tyr Ser Pro Val Leu Gly Tyr Ala Cys Ser Ile Phe Lys Asn
                885                 890                 895
```

```
att caa caa cta tat att gcc ctt ggg atg aat atc aat cca act ata    2736
Ile Gln Gln Leu Tyr Ile Ala Leu Gly Met Asn Ile Asn Pro Thr Ile
            900                 905                 910 aca cag aat atc aga gat cag tat ttt agg aat cca aat tgg atg caa    2784
Thr Gln Asn Ile Arg Asp Gln Tyr Phe Arg Asn Pro Asn Trp Met Gln
                915                 920                 925 tat gcc tct tta ata cct gct agt gtt ggg gga ttc aat tac atg gcc    2832
Tyr Ala Ser Leu Ile Pro Ala Ser Val Gly Gly Phe Asn Tyr Met Ala
        930                 935                 940 atg tca aga tgt ttt gta agg aat att ggt gat cca tca gtt gcc gca    2880
Met Ser Arg Cys Phe Val Arg Asn Ile Gly Asp Pro Ser Val Ala Ala
945                 950                 955                 960 ttg gct gat att aaa aga ttt att aag gcg aat cta tta gac cga agt    2928
Leu Ala Asp Ile Lys Arg Phe Ile Lys Ala Asn Leu Leu Asp Arg Ser
                965                 970                 975 gtt ctt tat agg att atg aat caa gaa cca ggt gag tca tct ttt ttg    2976
Val Leu Tyr Arg Ile Met Asn Gln Glu Pro Gly Glu Ser Ser Phe Leu
        980                 985                 990 gac tgg gct tca gat cca tat tca tgc aat tta cca caa tct caa aat    3024
Asp Trp Ala Ser Asp Pro Tyr Ser Cys Asn Leu Pro Gln Ser Gln Asn
            995                 1000                1005 ata acc acc atg ata aaa aat ata aca gca agg aat gta tta caa gat    3072
Ile Thr Thr Met Ile Lys Asn Ile Thr Ala Arg Asn Val Leu Gln Asp
        1010                1015                1020 tca cca aat cca tta tta tct gga tta ttc aca aat aca atg ata gaa    3120
Ser Pro Asn Pro Leu Leu Ser Gly Leu Phe Thr Asn Thr Met Ile Glu
1025                1030                1035                1040 gaa gat gaa gaa tta gct gag ttc ctg atg gac agg aag gta att ctc    3168
Glu Asp Glu Glu Leu Ala Glu Phe Leu Met Asp Arg Lys Val Ile Leu
                1045                1050                1055 cct aga gtt gca cat gat att cta gat aat tct ctc aca gga att aga    3216
Pro Arg Val Ala His Asp Ile Leu Asp Asn Ser Leu Thr Gly Ile Arg
        1060                1065                1070 aat gcc ata gct gga atg tta gat acg aca aaa tca cta att cgg gtt    3264
Asn Ala Ile Ala Gly Met Leu Asp Thr Thr Lys Ser Leu Ile Arg Val
            1075                1080                1085 ggc ata aat aga gga gga ctg aca tat agt ttg ttg agg aaa atc agt    3312
Gly Ile Asn Arg Gly Gly Leu Thr Tyr Ser Leu Leu Arg Lys Ile Ser
        1090                1095                1100 aat tac gat cta gta caa tat gaa aca cta agt agg act ttg cga cta    3360
Asn Tyr Asp Leu Val Gln Tyr Glu Thr Leu Ser Arg Thr Leu Arg Leu
1105                1110                1115                1120 att gta agt gat aaa atc aag tat gaa gat atg tgt tcg gta gac ctt    3408
Ile Val Ser Asp Lys Ile Lys Tyr Glu Asp Met Cys Ser Val Asp Leu
                1125                1130                1135 gcc ata gca ttg cga caa aag atg tgg att cat tta tca gga gga agg    3456
Ala Ile Ala Leu Arg Gln Lys Met Trp Ile His Leu Ser Gly Gly Arg
        1140                1145                1150 atg ata agt gga ctt gaa acg cct gac cca tta gaa tta cta tct ggg    3504
Met Ile Ser Gly Leu Glu Thr Pro Asp Pro Leu Glu Leu Leu Ser Gly
            1155                1160                1165 gta gta ata aca gga tca gaa cat tgt aaa ata tgt tat tct tca gat    3552
Val Val Ile Thr Gly Ser Glu His Cys Lys Ile Cys Tyr Ser Ser Asp
        1170                1175                1180 ggc aca aac cca tat act tgg atg tat tta ccc ggt aat atc aaa ata    3600
Gly Thr Asn Pro Tyr Thr Trp Met Tyr Leu Pro Gly Asn Ile Lys Ile
1185                1190                1195                1200 gga tca gca gaa aca ggt ata tcg tca tta aga gtt cct tat ttt gga    3648
Gly Ser Ala Glu Thr Gly Ile Ser Ser Leu Arg Val Pro Tyr Phe Gly
```

-continued

```
           1205                1210                1215
tca gtc act gat gaa aga tct gaa gca caa tta gga tat atc aag aat      3696
Ser Val Thr Asp Glu Arg Ser Glu Ala Gln Leu Gly Tyr Ile Lys Asn
            1220                1225                1230 ctt agt aaa cct gca aaa gcc gca ata aga ata gca atg ata tat aca      3744
Leu Ser Lys Pro Ala Lys Ala Ala Ile Arg Ile Ala Met Ile Tyr Thr
            1235                1240                1245 tgg gca ttt ggt aat gat gag ata tct tgg atg gaa gcc tca cag ata      3792
Trp Ala Phe Gly Asn Asp Glu Ile Ser Trp Met Glu Ala Ser Gln Ile
        1250                1255                1260 gca caa aca cgt gca aat ttt aca cta gat agt ctc aaa att tta aca      3840
Ala Gln Thr Arg Ala Asn Phe Thr Leu Asp Ser Leu Lys Ile Leu Thr
1265                1270                1275                1280 ccg gta gct aca tca aca aat tta tca cac aga tta aag gat act gca      3888
Pro Val Ala Thr Ser Thr Asn Leu Ser His Arg Leu Lys Asp Thr Ala
                1285                1290                1295 act cag atg aaa ttc tcc agt aca tca ttg atc aga gtc agc aga ttc      3936
Thr Gln Met Lys Phe Ser Ser Thr Ser Leu Ile Arg Val Ser Arg Phe
            1300                1305                1310 ata aca atg tcc aat gat aac atg tct atc aaa gaa gct aat gaa acc      3984
Ile Thr Met Ser Asn Asp Asn Met Ser Ile Lys Glu Ala Asn Glu Thr
        1315                1320                1325 aaa gat act aat ctt att tat caa caa ata atg tta aca gga tta agt      4032
Lys Asp Thr Asn Leu Ile Tyr Gln Gln Ile Met Leu Thr Gly Leu Ser
    1330                1335                1340 gtt ttc gaa tat tta ttt aga tta aaa gaa acc aca gga cac aac cct      4080
Val Phe Glu Tyr Leu Phe Arg Leu Lys Glu Thr Thr Gly His Asn Pro
1345                1350                1355                1360 ata gtt atg cat ctg cac ata gaa gat gag tgt tgt att aaa gaa agt      4128
Ile Val Met His Leu His Ile Glu Asp Glu Cys Cys Ile Lys Glu Ser
                1365                1370                1375 ttt aat gat gaa cat att aat cca gag tct aca tta gaa tta att cga      4176
Phe Asn Asp Glu His Ile Asn Pro Glu Ser Thr Leu Glu Leu Ile Arg
            1380                1385                1390 tat cct gaa agt aat gaa ttt att tat gat aaa gac cca ctc aaa gat      4224
Tyr Pro Glu Ser Asn Glu Phe Ile Tyr Asp Lys Asp Pro Leu Lys Asp
        1395                1400                1405 gtg gac tta tca aaa ctt atg gtt att aaa gac cat tct tac aca att      4272
Val Asp Leu Ser Lys Leu Met Val Ile Lys Asp His Ser Tyr Thr Ile
    1410                1415                1420 gat atg aat tat tgg gat gat act gac atc ata cat gca att tca ata      4320
Asp Met Asn Tyr Trp Asp Asp Thr Asp Ile Ile His Ala Ile Ser Ile
1425                1430                1435                1440 tgt act gca att aca ata gca gat act atg tca caa tta gat cga gat      4368
Cys Thr Ala Ile Thr Ile Ala Asp Thr Met Ser Gln Leu Asp Arg Asp
                1445                1450                1455 aat tta aaa gag ata ata gtt att gca aat gat gat gat att aat agc      4416
Asn Leu Lys Glu Ile Ile Val Ile Ala Asn Asp Asp Asp Ile Asn Ser
            1460                1465                1470 tta atc act gaa ttt ttg act ctt gac ata ctt gta ttt ctc aag aca      4464
Leu Ile Thr Glu Phe Leu Thr Leu Asp Ile Leu Val Phe Leu Lys Thr
        1475                1480                1485 ttt ggt gga tta tta gta aat caa ttt gca tac act ctt tat agt cta      4512
Phe Gly Gly Leu Leu Val Asn Gln Phe Ala Tyr Thr Leu Tyr Ser Leu
    1490                1495                1500 aaa ata gaa ggt agg gat ctc att tgg gat tat ata atg aga aca ctg      4560
Lys Ile Glu Gly Arg Asp Leu Ile Trp Asp Tyr Ile Met Arg Thr Leu
1505                1510                1515                1520 aga gat act tcc cat tca ata tta aaa gta tta tct aat gca tta tct      4608
```

-continued

```
Arg Asp Thr Ser His Ser Ile Leu Lys Val Leu Ser Asn Ala Leu Ser
        1525                1530                1535 cat cct aaa gta ttc aag agg ttc tgg gat tgt gga gtt tta aac cct      4656
His Pro Lys Val Phe Lys Arg Phe Trp Asp Cys Gly Val Leu Asn Pro
        1540                1545                1550 att tat ggt cct aat act gct agt caa gac cag ata aaa ctt gcc cta      4704
Ile Tyr Gly Pro Asn Thr Ala Ser Gln Asp Gln Ile Lys Leu Ala Leu
        1555                1560                1565 tct ata tgt gaa tat tca cta gat cta ttt atg aga gaa tgg ttg aat      4752
Ser Ile Cys Glu Tyr Ser Leu Asp Leu Phe Met Arg Glu Trp Leu Asn
        1570                1575                1580 ggt gta tca ctt gaa ata tac att tgt gac agc gat atg gaa gtt gca      4800
Gly Val Ser Leu Glu Ile Tyr Ile Cys Asp Ser Asp Met Glu Val Ala
1585                1590                1595                1600 aat gat agg aaa caa gcc ttt att tct aga cac ctt tca ttt gtt tgt      4848
Asn Asp Arg Lys Gln Ala Phe Ile Ser Arg His Leu Ser Phe Val Cys
        1605                1610                1615 tgt tta gca gaa att gca tct ttc gga cct aac ctg tta aac tta aca      4896
Cys Leu Ala Glu Ile Ala Ser Phe Gly Pro Asn Leu Leu Asn Leu Thr
        1620                1625                1630 tac ttg gag aga ctt gat cta ttg aaa caa tat ctt gaa tta aat att      4944
Tyr Leu Glu Arg Leu Asp Leu Leu Lys Gln Tyr Leu Glu Leu Asn Ile
        1635                1640                1645 aaa gaa gac cct act ctt aaa tat gta caa ata tct gga tta tta att      4992
Lys Glu Asp Pro Thr Leu Lys Tyr Val Gln Ile Ser Gly Leu Leu Ile
        1650                1655                1660 aaa tcg ttc cca tca act gta aca tac gta aga aag act gca atc aaa      5040
Lys Ser Phe Pro Ser Thr Val Thr Tyr Val Arg Lys Thr Ala Ile Lys
1665                1670                1675                1680 tat cta agg att cgc ggt att agt cca cct gag gta att gat gat tgg      5088
Tyr Leu Arg Ile Arg Gly Ile Ser Pro Pro Glu Val Ile Asp Asp Trp
        1685                1690                1695 gat ccg gta gaa gat gaa aat atg ctg gat aac att gtc aaa act ata      5136
Asp Pro Val Glu Asp Glu Asn Met Leu Asp Asn Ile Val Lys Thr Ile
        1700                1705                1710 aat gat aac tgt aat aaa gat aat aaa ggg aat aaa att aac aat ttc      5184
Asn Asp Asn Cys Asn Lys Asp Asn Lys Gly Asn Lys Ile Asn Asn Phe
        1715                1720                1725 tgg gga cta gca ctt aag aac tat caa gtc ctt aaa atc aga tct ata      5232
Trp Gly Leu Ala Leu Lys Asn Tyr Gln Val Leu Lys Ile Arg Ser Ile
        1730                1735                1740 aca agt gat tct gat gat aat gat aga cta gat gct aat aca agt ggt      5280
Thr Ser Asp Ser Asp Asp Asn Asp Arg Leu Asp Ala Asn Thr Ser Gly
1745                1750                1755                1760 ttg aca ctt cct caa gga ggg aat tat cta tcg cat caa ttg aga tta      5328
Leu Thr Leu Pro Gln Gly Gly Asn Tyr Leu Ser His Gln Leu Arg Leu
        1765                1770                1775 ttc gga atc aac agc act agt tgt ctg aaa gct ctt gag tta tca caa      5376
Phe Gly Ile Asn Ser Thr Ser Cys Leu Lys Ala Leu Glu Leu Ser Gln
        1780                1785                1790 att tta atg aag gaa gtc aat aaa gac aag gac agg ctc ttc ctg gga      5424
Ile Leu Met Lys Glu Val Asn Lys Asp Lys Asp Arg Leu Phe Leu Gly
        1795                1800                1805 gaa gga gca gga gct atg cta gca tgt tat gat gcc aca tta gga cct      5472
Glu Gly Ala Gly Ala Met Leu Ala Cys Tyr Asp Ala Thr Leu Gly Pro
        1810                1815                1820 gca gtt aat tat tat aat tca ggt ttg aat ata aca gat gta att ggt      5520
Ala Val Asn Tyr Tyr Asn Ser Gly Leu Asn Ile Thr Asp Val Ile Gly
1825                1830                1835                1840
```

-continued

```
caa cga gaa ttg aaa ata ttt cct tca gag gta tca tta gta ggt aaa       5568
Gln Arg Glu Leu Lys Ile Phe Pro Ser Glu Val Ser Leu Val Gly Lys
            1845                1850                1855 aaa tta gga aat gtg aca cag att ctt aac agg gta aaa gta ctg ttc       5616
Lys Leu Gly Asn Val Thr Gln Ile Leu Asn Arg Val Lys Val Leu Phe
            1860                1865                1870 aat ggg aat cct aat tca aca tgg ata gga aat atg gaa tgt gag agc       5664
Asn Gly Asn Pro Asn Ser Thr Trp Ile Gly Asn Met Glu Cys Glu Ser
            1875                1880                1885 tta ata tgg agt gaa tta aat gat aag tcc att gga tta gta cat tgt       5712
Leu Ile Trp Ser Glu Leu Asn Asp Lys Ser Ile Gly Leu Val His Cys
            1890                1895                1900 gat atg gaa gga gct atc ggt aaa tca gaa gaa act gtt cta cat gaa       5760
Asp Met Glu Gly Ala Ile Gly Lys Ser Glu Glu Thr Val Leu His Glu
1905                1910                1915                1920 cat tat agt gtt ata aga att aca tac ttg att ggg gat gat gat gtt       5808
His Tyr Ser Val Ile Arg Ile Thr Tyr Leu Ile Gly Asp Asp Asp Val
            1925                1930                1935 gtt tta gtt tcc aaa att ata cct aca atc act ccg aat tgg tct aga       5856
Val Leu Val Ser Lys Ile Ile Pro Thr Ile Thr Pro Asn Trp Ser Arg
            1940                1945                1950 ata ctt tat cta tat aaa tta tat tgg aaa gat gta agt ata ata tca       5904
Ile Leu Tyr Leu Tyr Lys Leu Tyr Trp Lys Asp Val Ser Ile Ile Ser
            1955                1960                1965 ctc aaa act tct aat cct gca tca aca gaa tta tat cta att tcg aaa       5952
Leu Lys Thr Ser Asn Pro Ala Ser Thr Glu Leu Tyr Leu Ile Ser Lys
            1970                1975                1980 gat gca tat tgt act ata atg gaa cct agt gaa att gtt tta tca aaa       6000
Asp Ala Tyr Cys Thr Ile Met Glu Pro Ser Glu Ile Val Leu Ser Lys
1985                1990                1995                2000 ctt aaa aga ttg tca ctc ttg gaa gaa aat aat cta tta aaa tgg atc       6048
Leu Lys Arg Leu Ser Leu Leu Glu Glu Asn Asn Leu Leu Lys Trp Ile
            2005                2010                2015 att tta tca aag aag agg aat aat gaa tgg tta cat cat gaa atc aaa       6096
Ile Leu Ser Lys Lys Arg Asn Asn Glu Trp Leu His His Glu Ile Lys
            2020                2025                2030 gaa gga gaa aga gat tat gga atc atg aga cca tat cat atg gca cta       6144
Glu Gly Glu Arg Asp Tyr Gly Ile Met Arg Pro Tyr His Met Ala Leu
            2035                2040                2045 caa atc ttt gga ttt caa atc aat tta aat cat ctg gcg aaa gaa ttt       6192
Gln Ile Phe Gly Phe Gln Ile Asn Leu Asn His Leu Ala Lys Glu Phe
            2050                2055                2060 tta tca acc cca gat ctg act aat atc aac aat ata atc caa agt ttt       6240
Leu Ser Thr Pro Asp Leu Thr Asn Ile Asn Asn Ile Ile Gln Ser Phe
2065                2070                2075                2080 cag cga aca ata aag gat gtt tta ttt gaa tgg att aat ata act cat       6288
Gln Arg Thr Ile Lys Asp Val Leu Phe Glu Trp Ile Asn Ile Thr His
            2085                2090                2095 gat gat aag aga cat aaa tta ggc gga aga tat aac ata ttc cca ctg       6336
Asp Asp Lys Arg His Lys Leu Gly Gly Arg Tyr Asn Ile Phe Pro Leu
            2100                2105                2110 aaa aat aag gga aag tta aga ctg cta tcg aga aga cta gta tta agt       6384
Lys Asn Lys Gly Lys Leu Arg Leu Leu Ser Arg Arg Leu Val Leu Ser
            2115                2120                2125 tgg att tca tta tca tta tcg act cga tta ctt aca ggt cgc ttt cct       6432
Trp Ile Ser Leu Ser Leu Ser Thr Arg Leu Leu Thr Gly Arg Phe Pro
            2130                2135                2140 gat gaa aaa ttt gaa cat aga gca cag act gga tat gta tca tta gct       6480
Asp Glu Lys Phe Glu His Arg Ala Gln Thr Gly Tyr Val Ser Leu Ala
2145                2150                2155                2160
```

```
gat act gat tta gaa tca tta aag tta ttg tcg aaa aac atc att aag      6528
Asp Thr Asp Leu Glu Ser Leu Lys Leu Leu Ser Lys Asn Ile Ile Lys
            2165                2170                2175 aat tac aga gag tgt ata gga tca ata tca tat tgg ttt cta acc aaa      6576
Asn Tyr Arg Glu Cys Ile Gly Ser Ile Ser Tyr Trp Phe Leu Thr Lys
            2180                2185                2190 gaa gtt aaa ata ctt atg aaa ttg att ggt ggt gct aaa tta tta gga      6624
Glu Val Lys Ile Leu Met Lys Leu Ile Gly Gly Ala Lys Leu Leu Gly
        2195                2200                2205 att ccc aga caa tat aaa gaa ccc gaa gac cag tta tta gaa aac tac      6672
Ile Pro Arg Gln Tyr Lys Glu Pro Glu Asp Gln Leu Leu Glu Asn Tyr
        2210                2215                2220 aat caa cat gat gaa ttt gat atc gat taa                              6702
Asn Gln His Asp Glu Phe Asp Ile Asp
2225                2230

<210> SEQ ID NO 3
<211> LENGTH: 572
<212> TYPE: PRT
<213> ORGANISM: Human parainfluenza virus 3

<400> SEQUENCE: 3

Met Glu Tyr Trp Lys His Thr Asn His Gly Lys Asp Ala Gly Asn Glu
 1               5                  10                  15

Leu Glu Thr Ser Met Ala Thr His Gly Asn Lys Leu Thr Asn Lys Ile
            20                  25                  30

Ile Tyr Ile Leu Trp Thr Ile Ile Leu Val Leu Leu Ser Ile Val Phe
        35                  40                  45

Ile Ile Val Leu Ile Asn Ser Ile Lys Ser Glu Lys Ala His Glu Ser
    50                  55                  60

Leu Leu Gln Asp Ile Asn Asn Glu Phe Met Glu Ile Thr Glu Lys Ile
65                  70                  75                  80

Gln Met Ala Ser Asp Asn Thr Asn Asp Leu Ile Gln Ser Gly Val Asn
                85                  90                  95

Thr Arg Leu Leu Thr Ile Gln Ser His Val Gln Asn Tyr Ile Pro Ile
            100                 105                 110

Ser Leu Thr Gln Gln Met Ser Asp Leu Arg Lys Phe Ile Ser Glu Ile
        115                 120                 125

Thr Ile Arg Asn Asp Asn Gln Glu Val Leu Pro Gln Arg Ile Thr His
    130                 135                 140

Asp Val Gly Ile Lys Pro Leu Asn Pro Asp Asp Phe Trp Arg Cys Thr
145                 150                 155                 160

Ser Gly Leu Pro Ser Leu Met Lys Thr Pro Lys Ile Arg Leu Met Pro
                165                 170                 175

Gly Pro Gly Leu Leu Ala Met Pro Thr Thr Val Asp Gly Cys Val Arg
            180                 185                 190

Thr Pro Ser Leu Val Ile Asn Asp Leu Ile Tyr Ala Tyr Thr Ser Asn
        195                 200                 205

Leu Ile Thr Arg Gly Cys Gln Asp Ile Gly Lys Ser Tyr Gln Val Leu
    210                 215                 220

Gln Ile Gly Ile Ile Thr Val Asn Ser Asp Leu Val Pro Asp Leu Asn
225                 230                 235                 240

Pro Arg Ile Ser His Thr Phe Asn Ile Asn Asp Asn Arg Lys Ser Cys
                245                 250                 255

Ser Leu Ala Leu Leu Asn Thr Asp Val Tyr Gln Leu Cys Ser Thr Pro
            260                 265                 270
```

```
Lys Val Asp Glu Arg Ser Asp Tyr Ala Ser Ser Gly Ile Glu Asp Ile
    275                 280                 285

Val Leu Asp Ile Val Asn Tyr Asp Gly Ser Ile Ser Thr Thr Arg Phe
    290                 295                 300

Lys Asn Asn Asn Ile Ser Phe Asp Gln Pro Tyr Ala Ala Leu Tyr Pro
305                 310                 315                 320

Ser Val Gly Pro Gly Ile Tyr Tyr Lys Gly Lys Ile Ile Phe Leu Gly
                325                 330                 335

Tyr Gly Gly Leu Glu His Pro Ile Asn Glu Asn Val Ile Cys Asn Thr
                340                 345                 350

Thr Gly Cys Pro Gly Lys Thr Gln Arg Asp Cys Asn Gln Ala Ser His
            355                 360                 365

Ser Pro Trp Phe Ser Asp Arg Arg Met Val Asn Ser Ile Ile Val Val
    370                 375                 380

Asp Lys Gly Leu Asn Ser Ile Pro Lys Leu Lys Val Trp Thr Ile Ser
385                 390                 395                 400

Met Arg Gln Asn Tyr Trp Gly Ser Glu Gly Arg Leu Leu Leu Leu Gly
                405                 410                 415

Asn Lys Ile Tyr Ile Tyr Thr Arg Ser Thr Ser Trp His Ser Lys Leu
                420                 425                 430

Gln Leu Gly Ile Ile Asp Ile Thr Asp Tyr Ser Asp Ile Arg Ile Lys
            435                 440                 445

Trp Thr Trp His Asn Val Leu Ser Arg Pro Gly Asn Asn Glu Cys Pro
    450                 455                 460

Trp Gly His Ser Cys Pro Asp Gly Cys Ile Thr Gly Val Tyr Thr Asp
465                 470                 475                 480

Ala Tyr Pro Leu Asn Pro Thr Gly Ser Ile Val Ser Ser Val Ile Leu
                485                 490                 495

Asp Ser Gln Lys Ser Arg Val Asn Pro Val Ile Thr Tyr Ser Thr Ala
                500                 505                 510

Thr Glu Arg Val Asn Glu Leu Ala Ile Leu Asn Arg Thr Leu Ser Ala
            515                 520                 525

Gly Tyr Thr Thr Thr Ser Cys Ile Thr His Tyr Asn Lys Gly Tyr Cys
    530                 535                 540

Phe His Ile Val Glu Ile Asn His Lys Ser Leu Asn Thr Phe Gln Pro
545                 550                 555                 560

Met Leu Phe Lys Thr Glu Ile Pro Lys Ser Cys Ser
                565                 570

<220> FEATURE:
<221> NAME/KEY: CDS
<222> LOCATION: (1)..(1719)

<210> SEQ ID NO 4
<211> LENGTH: 1719
<212> TYPE: DNA
<213> ORGANISM: Human parainfluenza virus 3

<400> SEQUENCE: 4 atg gaa tac tgg aag cat acc aat cac gga aag gat gct ggc aat gag      48
Met Glu Tyr Trp Lys His Thr Asn His Gly Lys Asp Ala Gly Asn Glu
  1               5                  10                  15 ctg gag acg tct atg gct act cat ggc aac aag ctc act aat aag ata      96
Leu Glu Thr Ser Met Ala Thr His Gly Asn Lys Leu Thr Asn Lys Ile
             20                  25                  30 ata tac ata tta tgg aca ata atc ctg gtg tta tta tca ata gtc ttc     144
```

```
                Ile Tyr Ile Leu Trp Thr Ile Ile Leu Val Leu Leu Ser Ile Val Phe
                             35                  40                  45 atc ata gtg cta att aat tcc atc aaa agt gaa aag gcc cac gaa tca              192
Ile Ile Val Leu Ile Asn Ser Ile Lys Ser Glu Lys Ala His Glu Ser
 50                  55                  60 ttg ctg caa gac ata aat aat gag ttt atg gaa att aca gaa aag atc              240
Leu Leu Gln Asp Ile Asn Asn Glu Phe Met Glu Ile Thr Glu Lys Ile
 65                  70                  75                  80 caa atg gca tcg gat aat acc aat gat cta ata cag tca gga gtg aat              288
Gln Met Ala Ser Asp Asn Thr Asn Asp Leu Ile Gln Ser Gly Val Asn
                 85                  90                  95 aca agg ctt ctt aca att cag agt cat gtc cag aat tac ata cca ata              336
Thr Arg Leu Leu Thr Ile Gln Ser His Val Gln Asn Tyr Ile Pro Ile
            100                 105                 110 tca ttg aca caa cag atg tca gat ctt agg aaa ttc att agt gaa att              384
Ser Leu Thr Gln Gln Met Ser Asp Leu Arg Lys Phe Ile Ser Glu Ile
        115                 120                 125 aca att aga aat gat aat caa gaa gtg ctg cca caa aga ata aca cat              432
Thr Ile Arg Asn Asp Asn Gln Glu Val Leu Pro Gln Arg Ile Thr His
130                 135                 140 gat gta ggt ata aaa cct tta aat cca gat gat ttt tgg aga tgc acg              480
Asp Val Gly Ile Lys Pro Leu Asn Pro Asp Asp Phe Trp Arg Cys Thr
145                 150                 155                 160 tct ggt ctt cca tct tta atg aaa act cca aaa ata agg tta atg cca              528
Ser Gly Leu Pro Ser Leu Met Lys Thr Pro Lys Ile Arg Leu Met Pro
                165                 170                 175 ggg ccg gga tta tta gct atg cca acg act gtt gat ggc tgt gtt aga              576
Gly Pro Gly Leu Leu Ala Met Pro Thr Thr Val Asp Gly Cys Val Arg
            180                 185                 190 act ccg tct tta gtt ata aat gat ctg att tat gct tat acc tca aat              624
Thr Pro Ser Leu Val Ile Asn Asp Leu Ile Tyr Ala Tyr Thr Ser Asn
        195                 200                 205 cta att act cga ggt tgt cag gat ata gga aaa tca tat caa gtc tta              672
Leu Ile Thr Arg Gly Cys Gln Asp Ile Gly Lys Ser Tyr Gln Val Leu
210                 215                 220 cag ata ggg ata ata act gta aac tca gac ttg gta cct gac tta aat              720
Gln Ile Gly Ile Ile Thr Val Asn Ser Asp Leu Val Pro Asp Leu Asn
225                 230                 235                 240 cct agg atc tct cat acc ttt aac ata aat gac aat agg aag tca tgt              768
Pro Arg Ile Ser His Thr Phe Asn Ile Asn Asp Asn Arg Lys Ser Cys
                245                 250                 255 tct cta gca ctc cta aat aca gat gta tat caa ctg tgt tca act ccc              816
Ser Leu Ala Leu Leu Asn Thr Asp Val Tyr Gln Leu Cys Ser Thr Pro
            260                 265                 270 aaa gtt gat gaa aga tca gat tat gca tca tca ggc ata gaa gat att              864
Lys Val Asp Glu Arg Ser Asp Tyr Ala Ser Ser Gly Ile Glu Asp Ile
        275                 280                 285 gta ctt gat att gtc aat tat gat ggt tca atc tca aca aca aga ttt              912
Val Leu Asp Ile Val Asn Tyr Asp Gly Ser Ile Ser Thr Thr Arg Phe
290                 295                 300 aag aat aat aac ata agc ttt gat caa cca tat gct gca cta tac cca              960
Lys Asn Asn Asn Ile Ser Phe Asp Gln Pro Tyr Ala Ala Leu Tyr Pro
305                 310                 315                 320 tct gtt gga cca ggg ata tac tac aaa ggc aaa ata ata ttt ctc ggg             1008
Ser Val Gly Pro Gly Ile Tyr Tyr Lys Gly Lys Ile Ile Phe Leu Gly
                325                 330                 335 tat gga ggt ctt gaa cat cca ata aat gag aat gta atc tgc aac aca             1056
Tyr Gly Gly Leu Glu His Pro Ile Asn Glu Asn Val Ile Cys Asn Thr
            340                 345                 350
```

```
act ggg tgc ccc ggg aaa aca cag aga gac tgt aat caa gcg tct cat    1104
Thr Gly Cys Pro Gly Lys Thr Gln Arg Asp Cys Asn Gln Ala Ser His
        355                 360                 365 agt cca tgg ttt tca gat agg agg atg gtc aac tcc atc att gtt gtt    1152
Ser Pro Trp Phe Ser Asp Arg Arg Met Val Asn Ser Ile Ile Val Val
370                 375                 380 gac aaa ggc tta aac tca att cca aaa ttg aaa gta tgg acg ata tct    1200
Asp Lys Gly Leu Asn Ser Ile Pro Lys Leu Lys Val Trp Thr Ile Ser
385                 390                 395                 400 atg cga caa aat tac tgg ggg tca gaa gga agg tta ctt cta cta ggt    1248
Met Arg Gln Asn Tyr Trp Gly Ser Glu Gly Arg Leu Leu Leu Leu Gly
                405                 410                 415 aac aag atc tat ata tat aca aga tct aca agt tgg cat agc aag tta    1296
Asn Lys Ile Tyr Ile Tyr Thr Arg Ser Thr Ser Trp His Ser Lys Leu
            420                 425                 430 caa tta gga ata att gat att act gat tac agt gat ata agg ata aaa    1344
Gln Leu Gly Ile Ile Asp Ile Thr Asp Tyr Ser Asp Ile Arg Ile Lys
        435                 440                 445 tgg aca tgg cat aat gtg cta tca aga cca gga aac aat gaa tgt cca    1392
Trp Thr Trp His Asn Val Leu Ser Arg Pro Gly Asn Asn Glu Cys Pro
450                 455                 460 tgg gga cat tca tgt cca gat gga tgt ata aca gga gta tat act gat    1440
Trp Gly His Ser Cys Pro Asp Gly Cys Ile Thr Gly Val Tyr Thr Asp
465                 470                 475                 480 gca tat cca ctc aat ccc aca ggg agc att gtg tca tct gtc ata tta    1488
Ala Tyr Pro Leu Asn Pro Thr Gly Ser Ile Val Ser Ser Val Ile Leu
                485                 490                 495 gac tca caa aaa tcg aga gtg aac cca gtc ata act tac tca aca gca    1536
Asp Ser Gln Lys Ser Arg Val Asn Pro Val Ile Thr Tyr Ser Thr Ala
            500                 505                 510 acc gaa aga gta aac gag ctg gcc atc cta aac aga aca ctc tca gct    1584
Thr Glu Arg Val Asn Glu Leu Ala Ile Leu Asn Arg Thr Leu Ser Ala
        515                 520                 525 gga tat aca aca aca agc tgc att aca cac tat aac aaa gga tat tgt    1632
Gly Tyr Thr Thr Thr Ser Cys Ile Thr His Tyr Asn Lys Gly Tyr Cys
530                 535                 540 ttt cat ata gta gaa ata aat cat aaa agc tta aac aca ttt caa ccc    1680
Phe His Ile Val Glu Ile Asn His Lys Ser Leu Asn Thr Phe Gln Pro
545                 550                 555                 560 atg ttg ttc aaa aca gag att cca aaa agc tgc agt taa                1719
Met Leu Phe Lys Thr Glu Ile Pro Lys Ser Cys Ser
                565                 570
```

<210> SEQ ID NO 5
<211> LENGTH: 20
<212> TYPE: DNA
<213> ORGANISM: Human parainfluenza virus 3

<400> SEQUENCE: 5
ccaacaacaa ctcccagatc                                              20

<210> SEQ ID NO 6
<211> LENGTH: 20
<212> TYPE: DNA
<213> ORGANISM: Human parainfluenza virus 3

<400> SEQUENCE: 6
tgcctccata agtgggtcaa                                              20

<210> SEQ ID NO 7

-continued

```
<211> LENGTH: 24
<212> TYPE: DNA
<213> ORGANISM: Human parainfluenza virus 3

<400> SEQUENCE: 7
gcatggagtc ctgtggcatc cacg                                           24

<210> SEQ ID NO 8
<211> LENGTH: 24
<212> TYPE: DNA
<213> ORGANISM: Human parainfluenza virus 3

<400> SEQUENCE: 8
ctagaagcat ttgcggtgga cgat                                           24
```